US010686139B2

(12) United States Patent
Nakano et al.

(10) Patent No.: US 10,686,139 B2
(45) Date of Patent: Jun. 16, 2020

(54) NITROGEN-CONTAINING COMPOUND AND ORGANIC ELECTROLUMINESCENCE DEVICE INCLUDING THE SAME

(71) Applicants: SAMSUNG DISPLAY CO., LTD., Yongin-si (KR); KYUSHU UNIVERSITY, NATIONAL UNIVERSITY CORPORATION, Fukuoka-shi, Fukuoka (JP)

(72) Inventors: Hiromi Nakano, Yokohama (JP); Shuri Sato, Yokohama (JP); Yoshimasa Fujita, Yokohama (JP); Nobutaka Akashi, Yokohama (JP); Takuma Yasuda, Fukuoka (JP); Inseob Park, Fukuoka (JP)

(73) Assignees: Samsung Display Co., Ltd., Yongin-si (KR); Kyushu University, National University Corporation, Fukuoka-shi (JP)

( * ) Notice: Subject to any disclaimer, the term of this patent is extended or adjusted under 35 U.S.C. 154(b) by 424 days.

(21) Appl. No.: 15/378,084

(22) Filed: Dec. 14, 2016

(65) Prior Publication Data

US 2017/0346017 A1 Nov. 30, 2017

(30) Foreign Application Priority Data

May 26, 2016 (KR) ........................ 10-2016-0065045

(51) Int. Cl.
*C07D 401/10* (2006.01)
*H01L 51/00* (2006.01)
(Continued)

(52) U.S. Cl.
CPC ........ *H01L 51/0067* (2013.01); *C07D 401/10* (2013.01); *C07D 401/14* (2013.01);
(Continued)

(58) Field of Classification Search
None
See application file for complete search history.

(56) References Cited

U.S. PATENT DOCUMENTS 8,609,257 B2 12/2013 Ise et al.
8,847,218 B2 * 9/2014 Nishimura .............. C09B 57/00 257/40

(Continued)

FOREIGN PATENT DOCUMENTS

JP 2006156445 A * 6/2006 ............ H01L 51/50
JP 2011-49511 A 3/2011

(Continued)

OTHER PUBLICATIONS

Machine translation of JP-2006156445, translation generated Feb. 2019, 28 pages (Year: 2019).*

(Continued)

*Primary Examiner* — Robert S Loewe
(74) *Attorney, Agent, or Firm* — Lewis Roca Rothgerber Christie LLP

(57) ABSTRACT

A nitrogen-containing compound and an organic electroluminescence device including the same, the nitrogen-containing compound being represented by the following Formula 1:

[Formula 1]

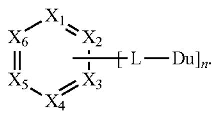

18 Claims, 1 Drawing Sheet

10

(51) Int. Cl.

| | |
|---|---|
| ***C07D 401/14*** | (2006.01) |
| ***C07D 403/14*** | (2006.01) |
| ***C07D 491/107*** | (2006.01) |
| ***C09K 11/06*** | (2006.01) |
| *H01L 51/50* | (2006.01) |

(52) U.S. Cl.

CPC ....... *C07D 403/14* (2013.01); *C07D 491/107* (2013.01); *C09K 11/06* (2013.01); *H01L 51/0071* (2013.01); *H01L 51/0072* (2013.01); *C09K 2211/1007* (2013.01); *C09K 2211/1044* (2013.01); *H01L 51/5016* (2013.01); *H01L 51/5056* (2013.01); *H01L 51/5072* (2013.01)

(56) References Cited

U.S. PATENT DOCUMENTS

| | | | | |
|---|---|---|---|---|
| 9,159,941 | B2 | 10/2015 | Ogiwara | |
| 9,963,429 | B2 | 5/2018 | Mizuki et al. | |
| 10,032,991 | B2 | 7/2018 | Ikeda et al. | |
| 2005/0186446 | A1* | 8/2005 | Shitagaki | C07D 241/42<br>428/690 |
| 2013/0020558 | A1* | 1/2013 | Ogiwara | H01L 51/0067<br>257/40 |
| 2013/0292659 | A1* | 11/2013 | Kim | C07D 209/82<br>257/40 |
| 2014/0034916 | A1* | 2/2014 | Kim | H01L 51/0072<br>257/40 |
| 2015/0126736 | A1* | 5/2015 | Cho | C07D 401/14<br>544/212 |
| 2016/0028025 | A1* | 1/2016 | Ogiwara | H01L 51/5004<br>257/40 |
| 2016/0093812 | A1 | 3/2016 | Stoessel et al. | |
| 2016/0093813 | A1 | 3/2016 | Stoessel et al. | |
| 2016/0168162 | A1* | 6/2016 | Chae | C07D 491/147<br>257/40 |
| 2016/0172600 | A1* | 6/2016 | MacDonald | C07D 409/14 |
| 2016/0190477 | A1 | 6/2016 | Kawakami et al. | |
| 2016/0372683 | A1* | 12/2016 | Tanimoto | H01L 51/0067 |
| 2017/0244049 | A1* | 8/2017 | Aspuru-Guzik | C09K 11/06 |

FOREIGN PATENT DOCUMENTS

| | | | | | |
|---|---|---|---|---|---|
| JP | 2016-130231 | A | | 7/2016 | |
| KR | 20110102055 | A | * | 9/2011 | H01L 51/50 |
| KR | 2011110508 | | * | 10/2011 | C09B 57/00 |
| KR | 10-2013-0142967 | A | | 12/2013 | |
| KR | 10-2015-0070860 | A | | 6/2015 | |
| KR | 10-2015-0143353 | A | | 12/2015 | |
| KR | 10-2015-0143552 | A | | 12/2015 | |
| KR | 10-1769764 | B1 | | 8/2017 | |
| WO | 2012048266 | A1 | | 4/2012 | |
| WO | WO 2012/077902 | A2 | | 6/2012 | |
| WO | 2012099219 | A1 | | 7/2012 | |
| WO | WO 2013/081088 | A1 | | 6/2013 | |
| WO | WO 2013/172255 | A1 | | 11/2013 | |
| WO | WO 2014/058124 | A1 | | 4/2014 | |
| WO | WO 2014/148493 | A1 | | 9/2014 | |
| WO | WO 2014/196585 | A1 | | 12/2014 | |
| WO | 2015020217 | A1 | | 2/2015 | |
| WO | WO 2015/016200 | A1 | | 2/2015 | |
| WO | WO 2015/022835 | A1 | | 2/2015 | |
| WO | WO-2015016200 | A1 | * | 2/2015 | H01L 51/50 |
| WO | 2015033894 | A1 | | 3/2015 | |
| WO | 2015093551 | A1 | | 6/2015 | |
| WO | WO-2015121241 | A1 | * | 8/2015 | C09K 11/06 |
| WO | 2015175678 | A1 | | 11/2015 | |

OTHER PUBLICATIONS

Komatsu et al. "Light-blue thermally activated delayed fluorescent emitters realizing a high external quantum efficiency of 25% and unprecedented low drive voltages in OLEDs" J. Mater. Chem. C. Apr. 2016, 2274. (Year: 2016).*

Sun et al. "Thermally Activated Delayed Fluorescence from Azasiline Based Intramolecular Charge-Transfer Emitter (DTPDDA) and a Highly Efficient Blue Light Emitting Diode" Chem. Mater. 2015, 27, 6675-6681. (Year: 2015).*

* cited by examiner

NITROGEN-CONTAINING COMPOUND AND ORGANIC ELECTROLUMINESCENCE DEVICE INCLUDING THE SAME

CROSS-REFERENCE TO RELATED APPLICATION

Korean Patent Application No. 10-2016-0065045, filed on May 26, 2016, in the Korean Intellectual Property Office, and entitled: "Nitrogen-Containing Compound and Organic Electroluminescence Device Including the Same," is incorporated by reference herein in its entirety.

BACKGROUND

1. Field

Embodiments relate to a nitrogen-containing compound and an organic electroluminescence device including the same.

2. Description of the Related Art

The development of an organic electroluminescence display as an image display is being actively conducted. The organic electroluminescence display is different from a liquid crystal display and is a self-luminescent display accomplishing display via the recombination of holes and electrons (injected from a first electrode and a second electrode) in an emission layer and the light emission from a luminescent material including an organic compound in the emission layer.

An organic electroluminescence device may include, e.g., a first electrode, a hole transport layer disposed on the first electrode, an emission layer disposed on the hole transport layer, an electron transport layer disposed on the emission layer, and a second electrode disposed on the electron transport layer. Holes are injected from the first electrode, and the injected holes move via the hole transport layer and are injected to the emission layer. Meanwhile, electrons are injected from the second electrode, and the injected electrons move via the electron transport layer and are injected to the emission layer. The holes and the electrons injected to the emission layer recombine to produce excitons in the emission layer. The organic electroluminescence device may emit light using light generated by the excitons.

SUMMARY

Embodiments are directed to a nitrogen-containing compound and an organic electroluminescence device including the same.

The embodiments may be realized by providing a nitrogen-containing compound represented by the following Formula 1:

[Formula 1]

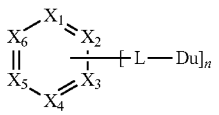

wherein, in Formula 1, $X_1$ to $X_6$ are each independently $CR_1$ or N, provided that one or two of $X_1$ to $X_6$ are N, each $R_1$ is independently a bond to L, a hydrogen atom, a deuterium atom, a halogen atom, a substituted or unsubstituted alkyl group having 1 to 30 carbon atoms, a substituted or unsubstituted aryl group having 6 to 30 ring carbon atoms, or a substituted or unsubstituted heteroaryl group having 2 to 30 ring carbon atoms, L is a substituted or unsubstituted arylene group having 6 to 30 ring carbon atoms, n is 1 or 2, and Du is a group represented by the following Formula 2,

[Formula 2]

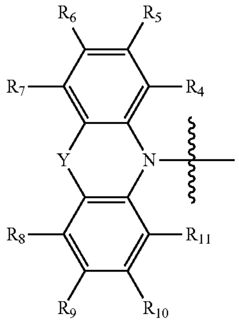

wherein, in Formula 2, Y is a direct linkage, O, S, $CR_2R_3$, Si, Ge, P, or P═O, $R_2$ to $R_{11}$ are each independently a hydrogen atom, a deuterium atom, a substituted or unsubstituted alkyl group having 1 to 30 carbon atoms, a substituted or unsubstituted aryl group having 6 to 30 ring carbon atoms, or a substituted or unsubstituted heteroaryl group of 2 to 30 ring carbon atoms, adjacent ones of $R_2$ to $R_{11}$ are separate or are combined to form a ring, and

represents a bonding site with L of Formula 1.

L may be a substituted or unsubstituted phenylene group.

The nitrogen-containing compound represented by Formula 1 may be represented by the following Formula 3:

[Formula 3]

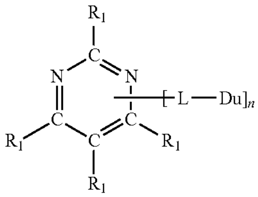

wherein, in Formula 3, L, Du, $R_1$, and n are defined the same as those of Formula 1.

The nitrogen-containing compound represented by Formula 1 may be represented by the following Formula 4:

[Formula 4]

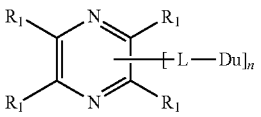

wherein, in Formula 4, L, Du, $R_1$, and n are defined the same as those of Formula 1.

The nitrogen-containing compound represented by Formula 1 may be represented by the following Formula 5:

[Formula 5]

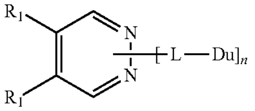

wherein, in Formula 5, L, Du, $R_1$, and n are defined the same as those of Formula 1.

Y may be the direct linkage or $CR_2R_3$.

The nitrogen-containing compound represented by the above Formula 1 may be represented by the following Formula 6:

[Formula 6]

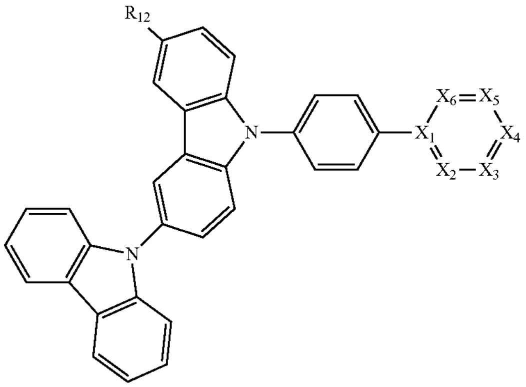

wherein, in Formula 6, $R_{12}$ is a hydrogen atom or a substituted or unsubstituted carbazole group, and $X_1$ to $X_6$ are defined the same as those of Formula 1.

The group represented by Formula 2 may be represented by one of the following Formulae 7 to 16, in which

is defined the same as that of Formula 2:

[Formula 7]

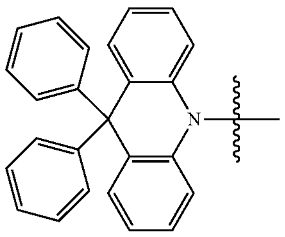

[Formula 8]

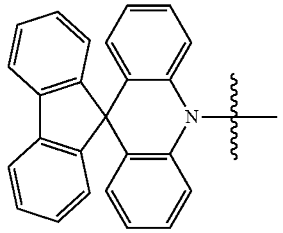

-continued

[Formula 9]

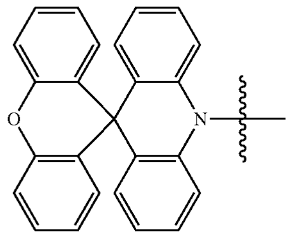

[Formula 10]

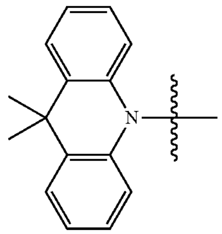

[Formula 11]

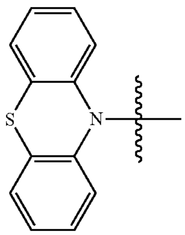

[Formula 12]

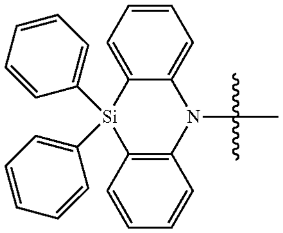

[Formula 13]

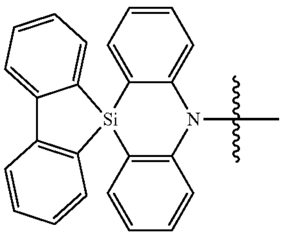

[Formula 14]

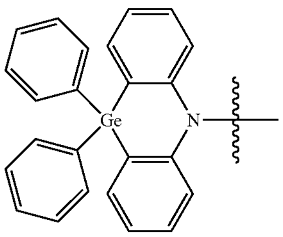

-continued
[Formula 15]
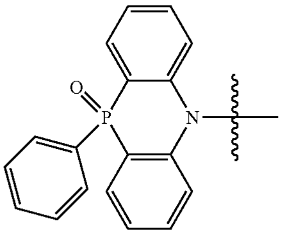
-continued
[Formula 16]
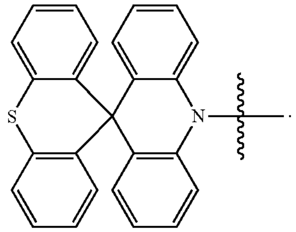
The nitrogen-containing compound represented by Formula 1 may be one of the following Compounds 1 to 95:
1
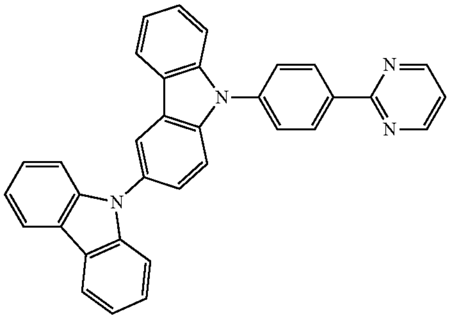
2
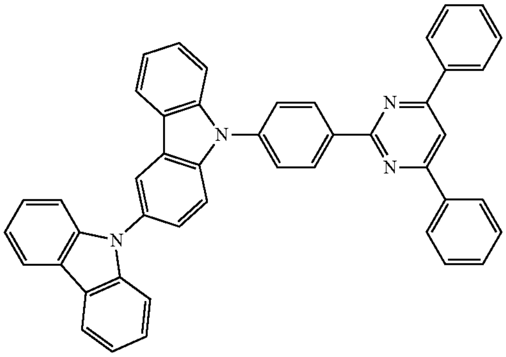
3
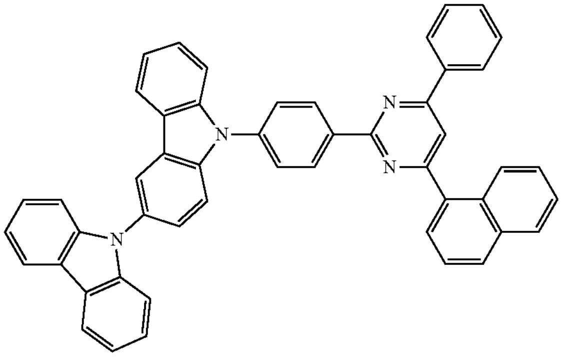
4
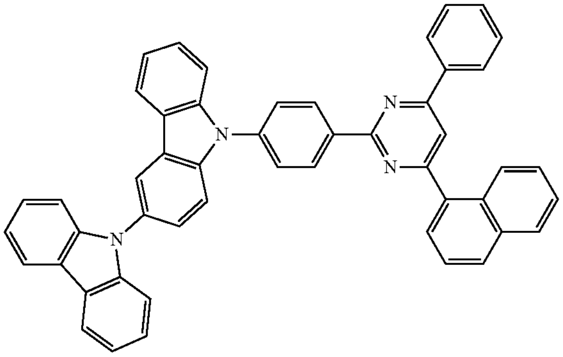
5
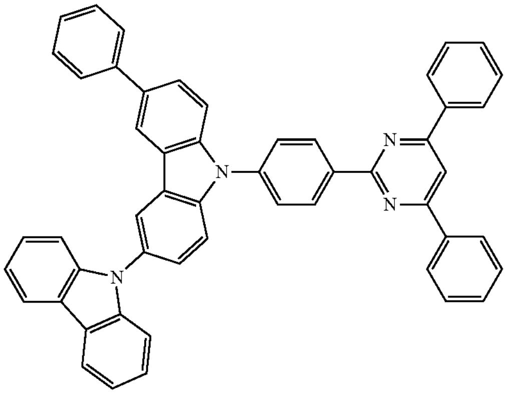
6
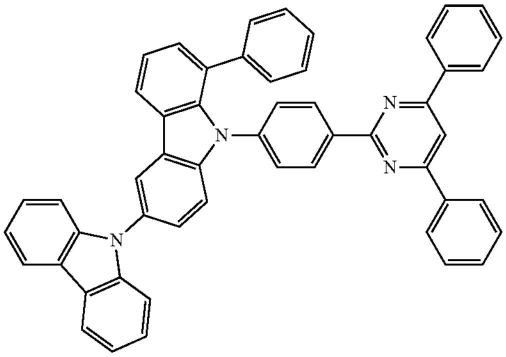

-continued
7
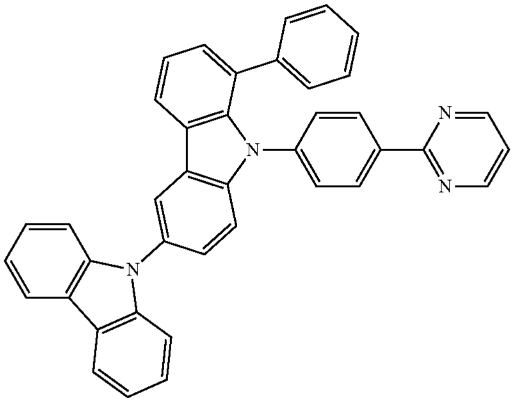
8
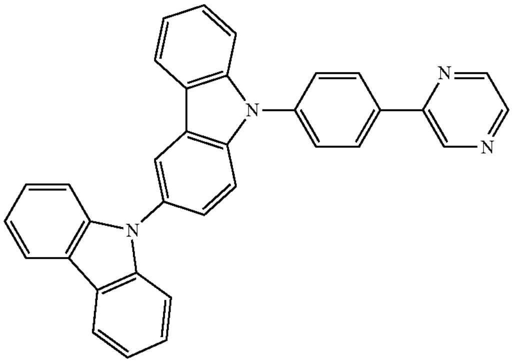
9
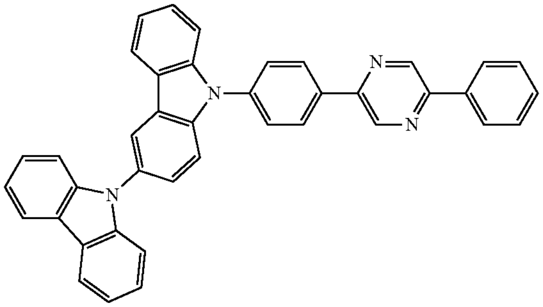
10
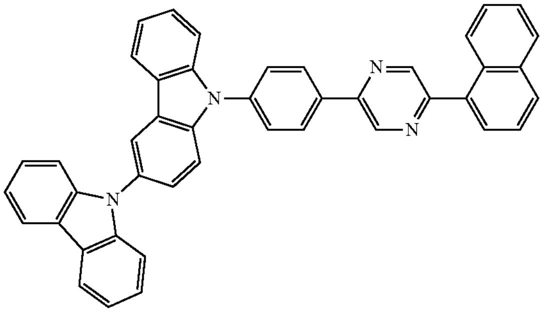
11
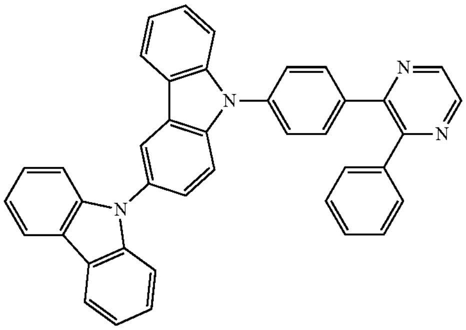
12
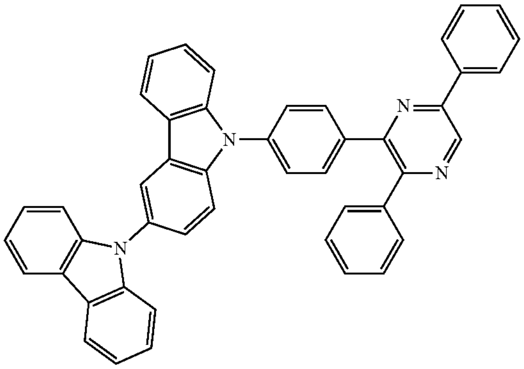
13
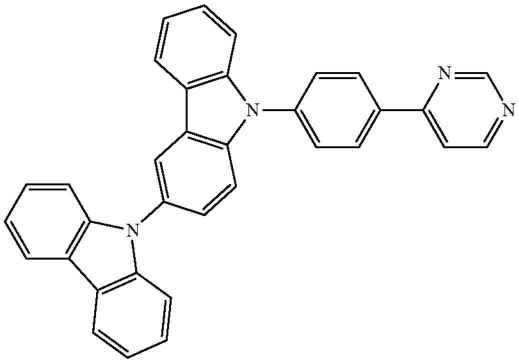
14
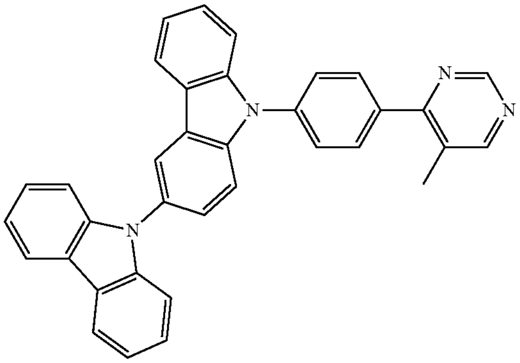

-continued
15
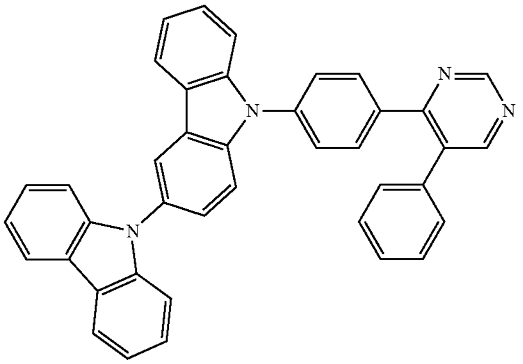
16
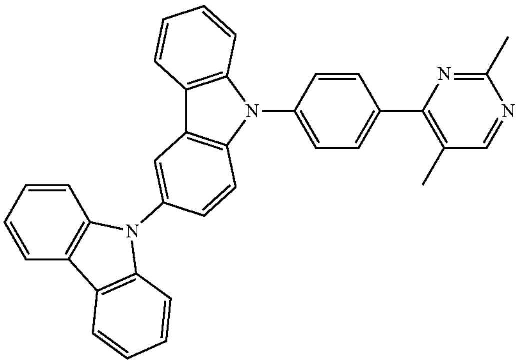
17
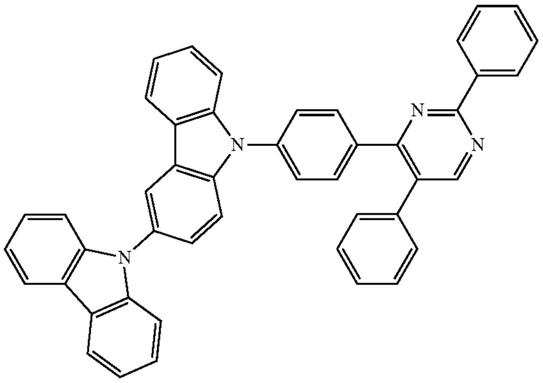
18
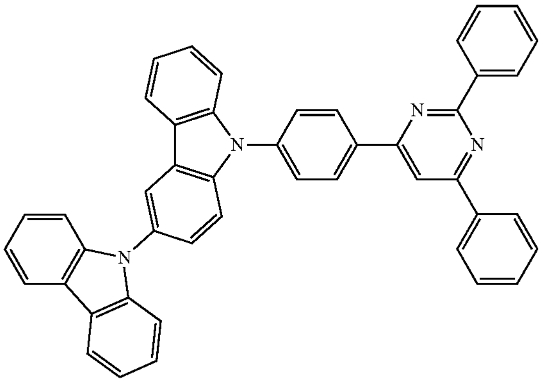
19
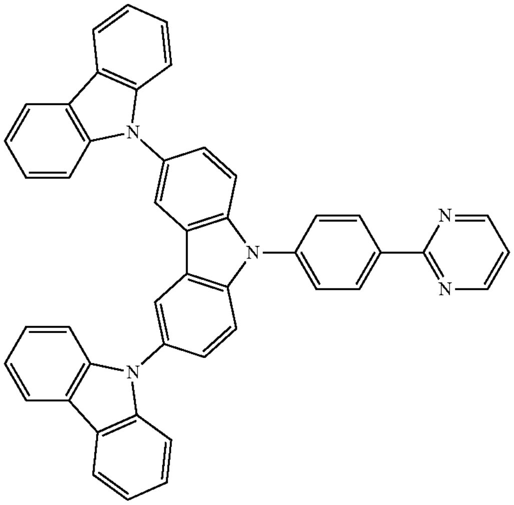
20
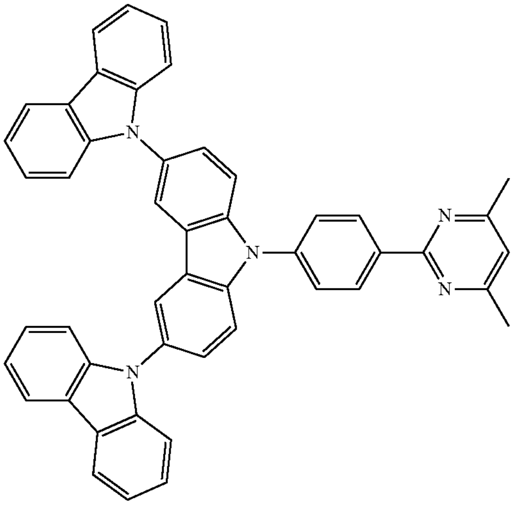

-continued
21
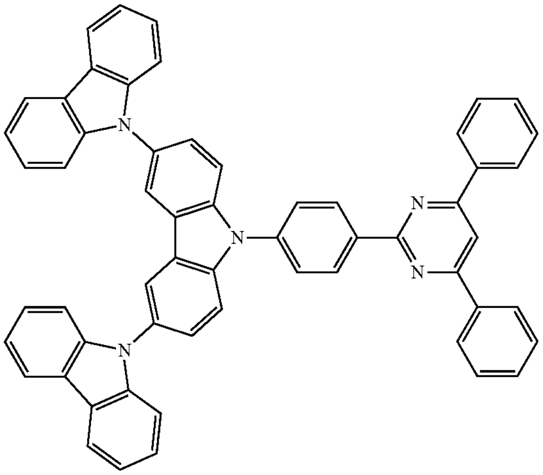
22
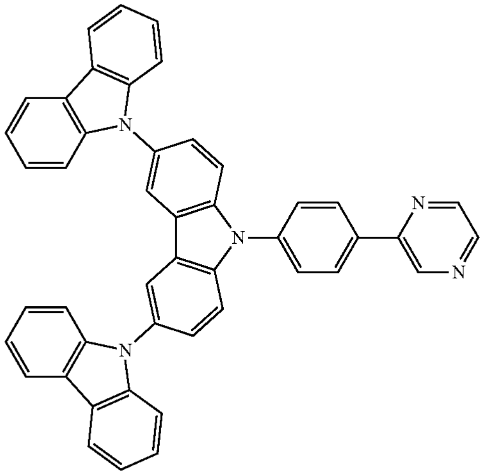
23
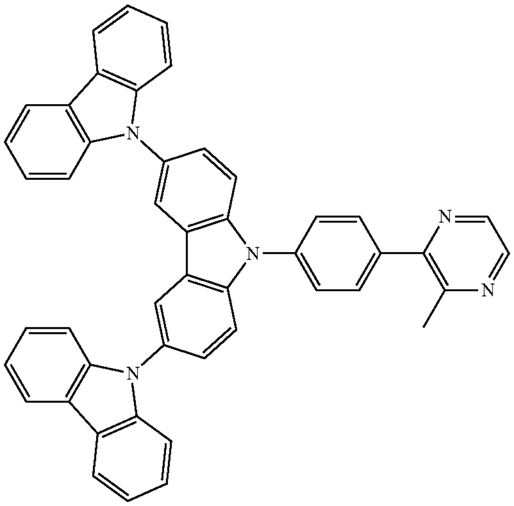
24
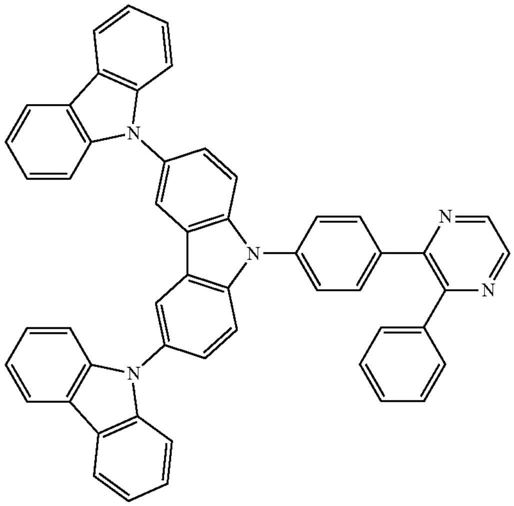
25
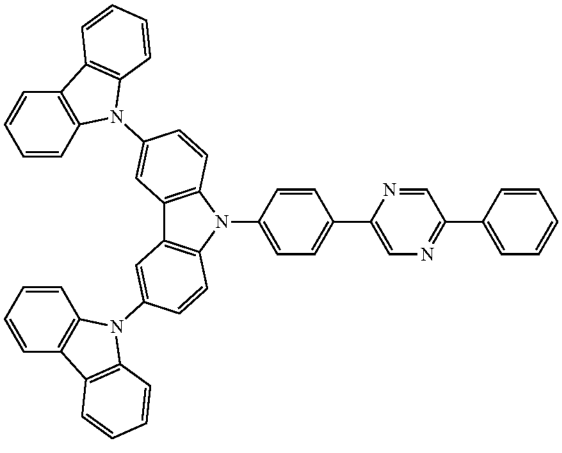
26
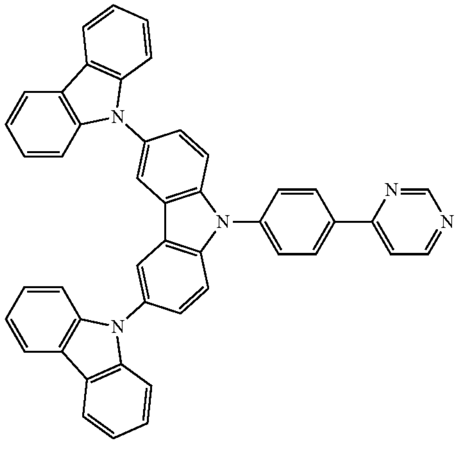

-continued
27
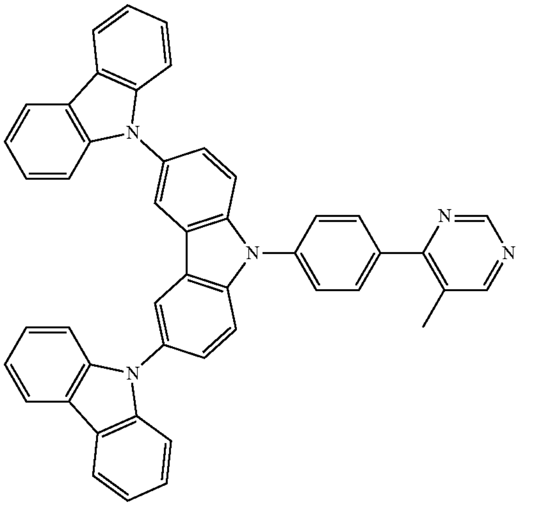
28
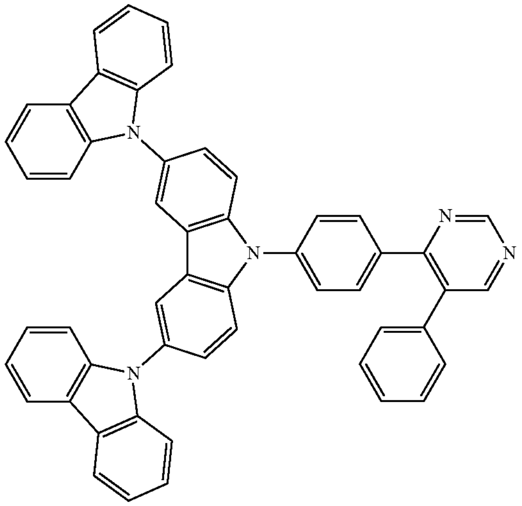
29
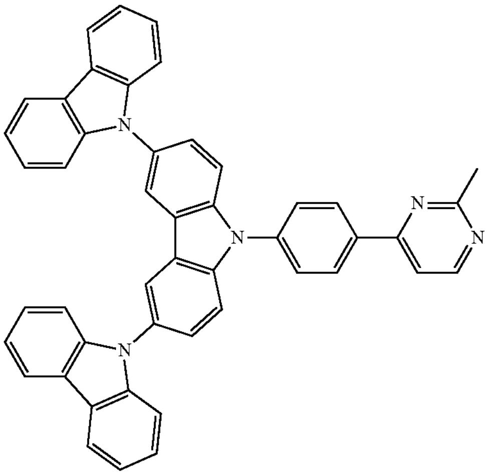
30
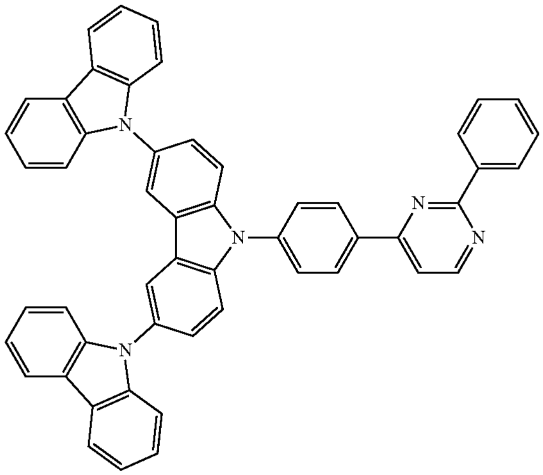
31
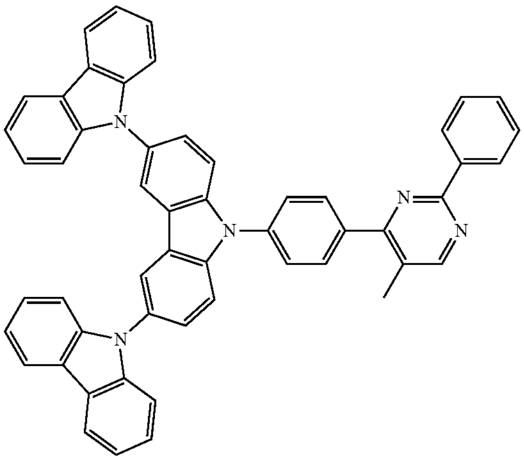
32
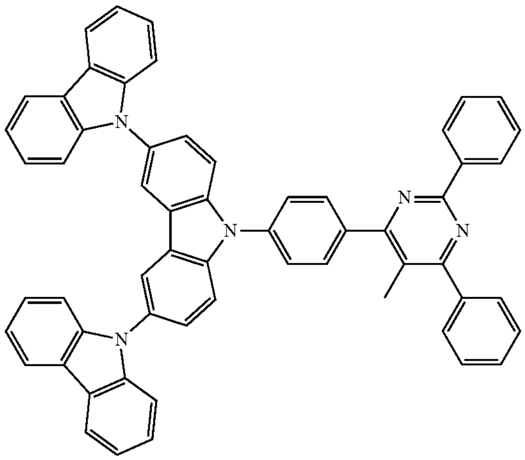

-continued
33
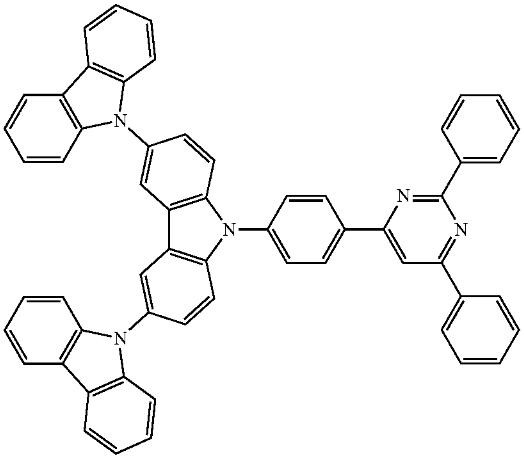
34
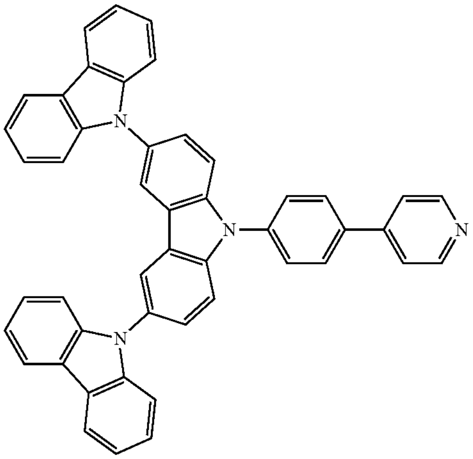
35
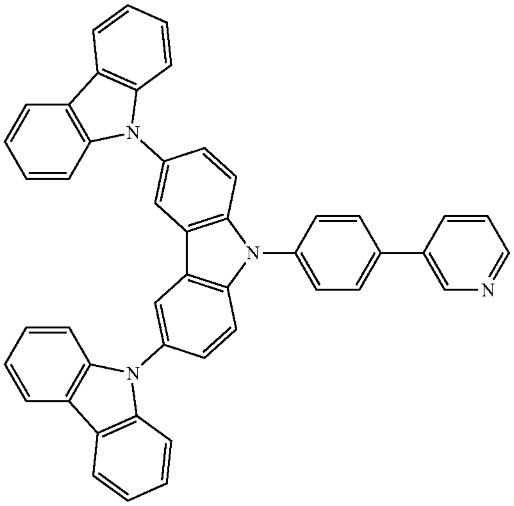
36
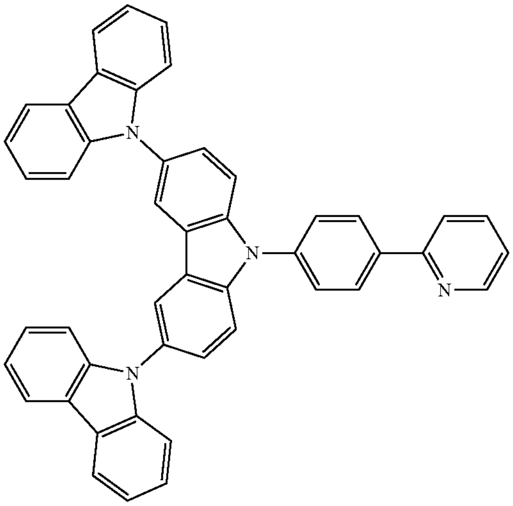
37
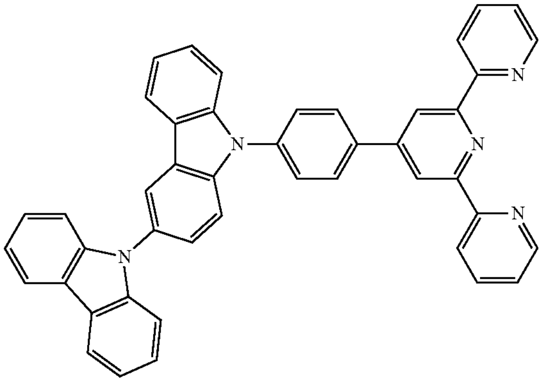
38
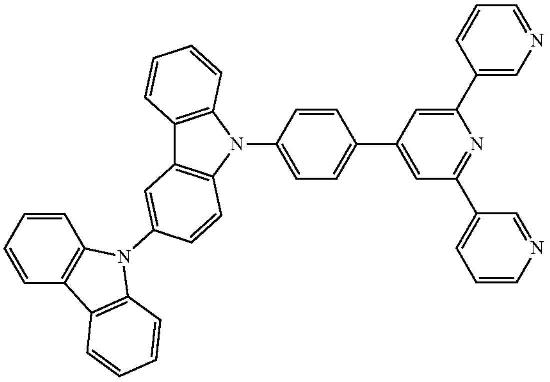

-continued
39
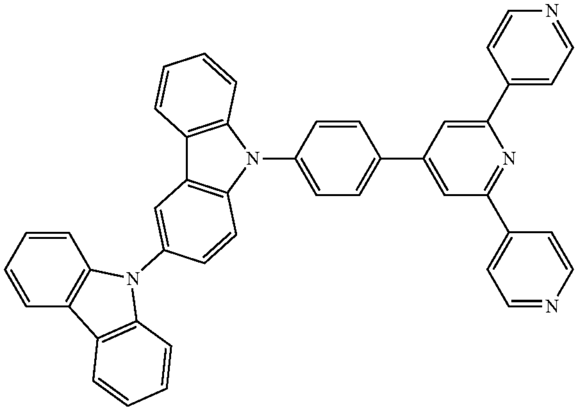
40
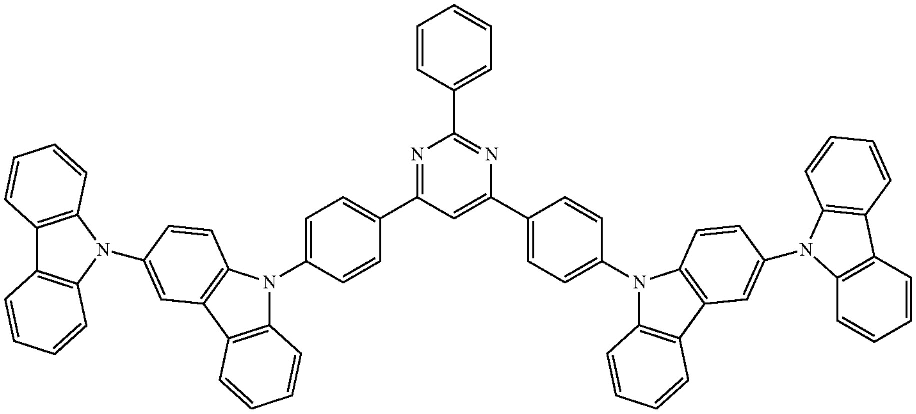
41
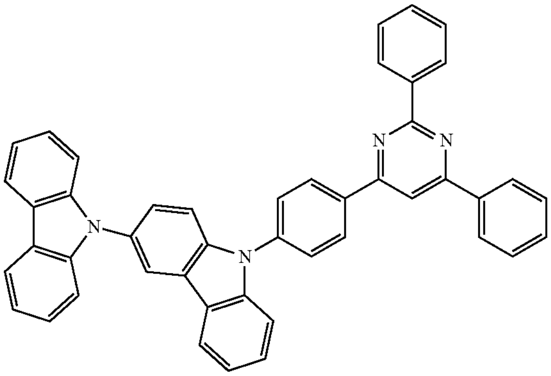
42
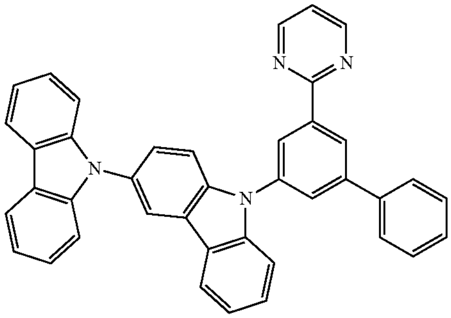
43
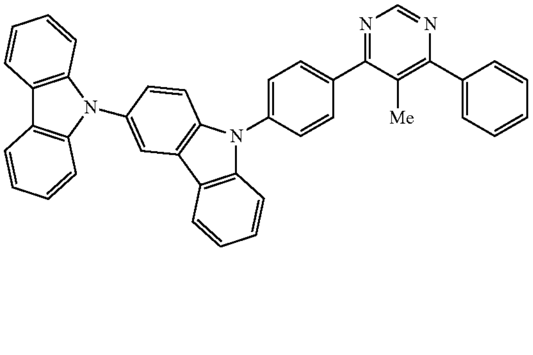
44
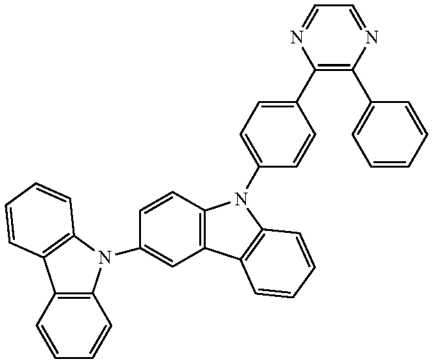

-continued
45
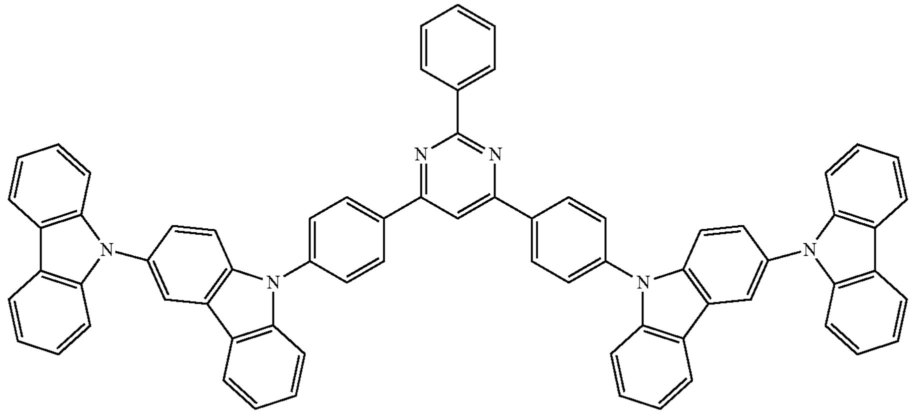
46
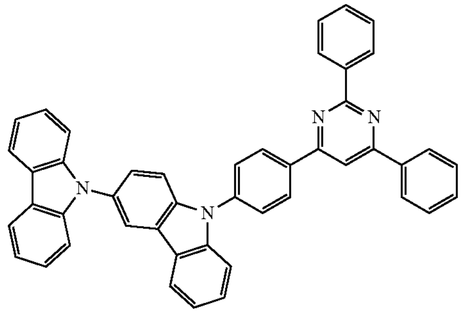
47
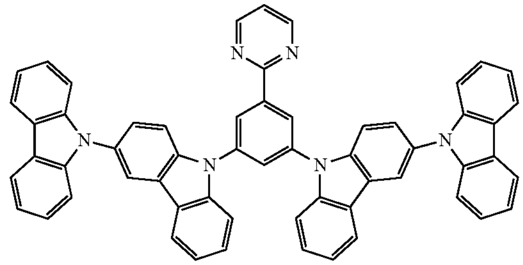
48
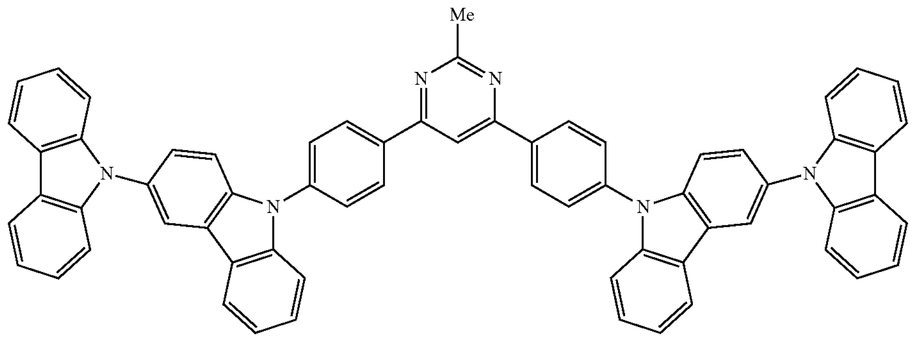
49
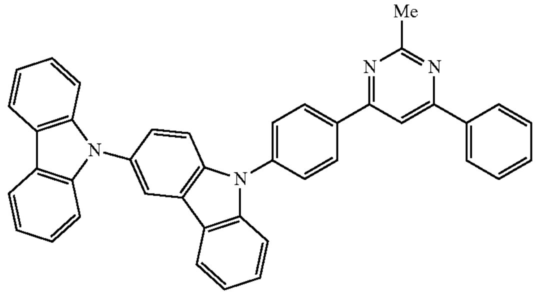

-continued
50
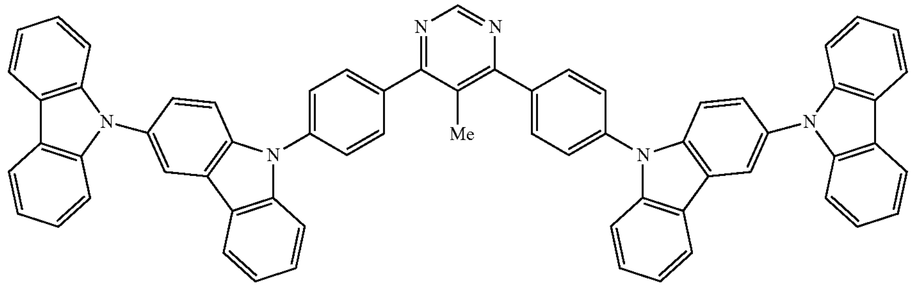
51
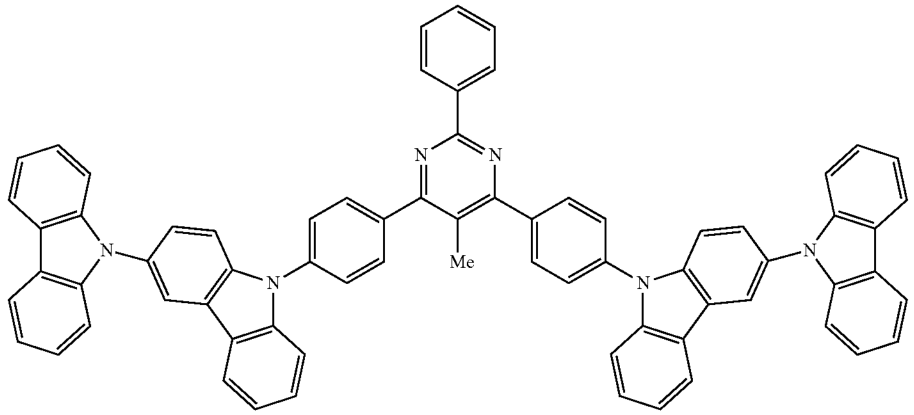
52
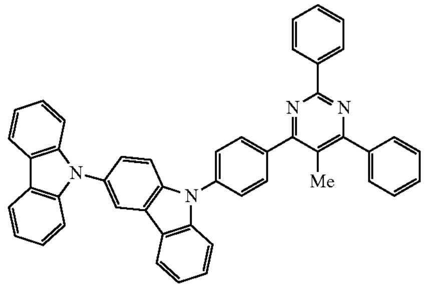
53
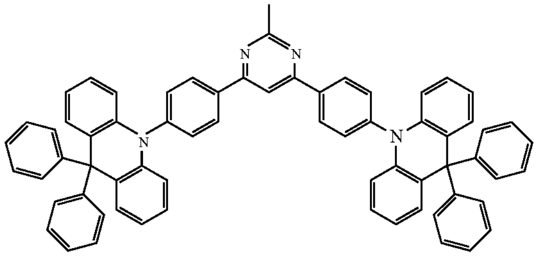
54
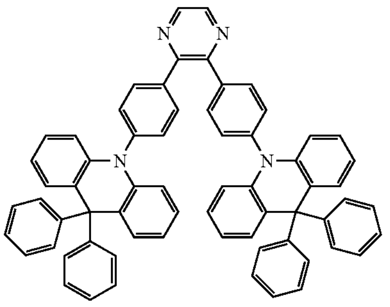
55
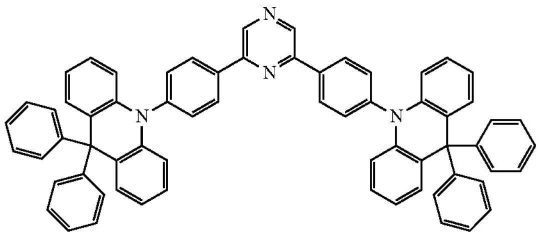
56
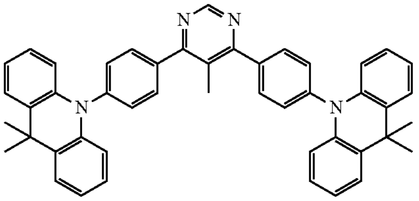
57
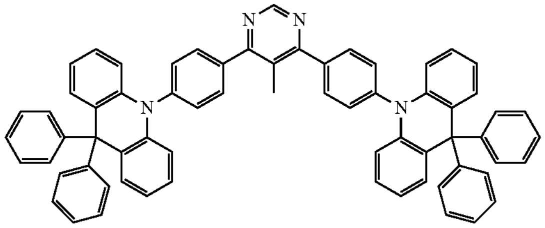

-continued
58
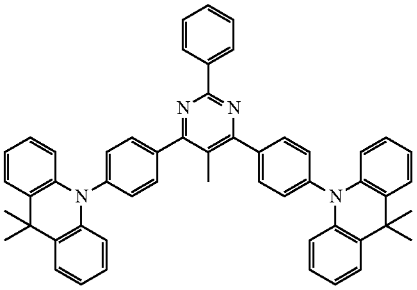
59
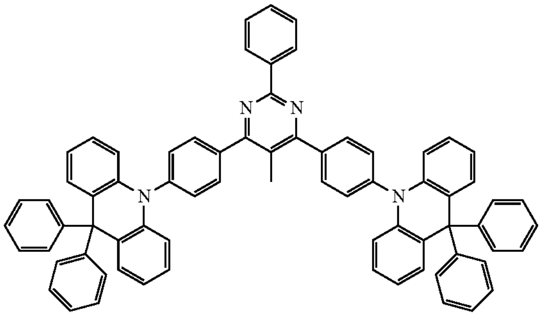
60
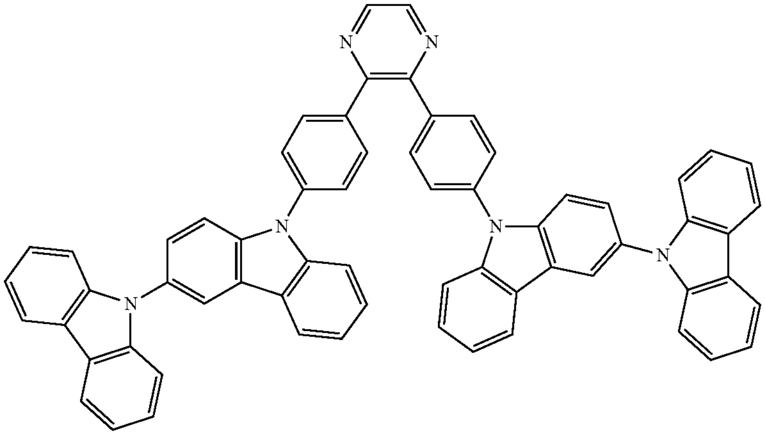
61
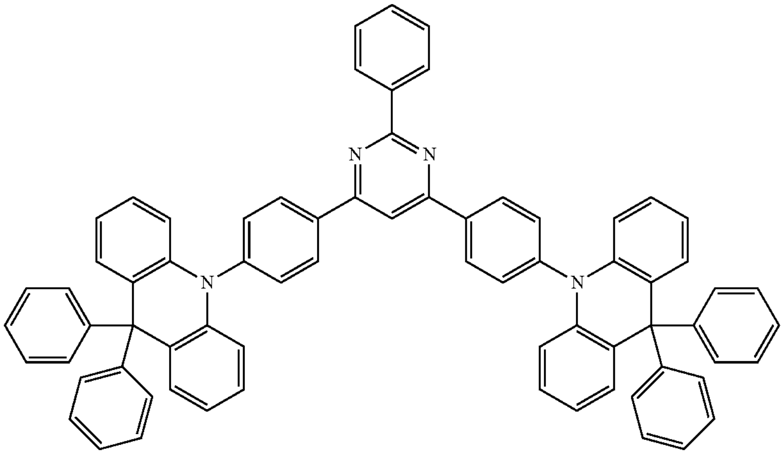

-continued
62
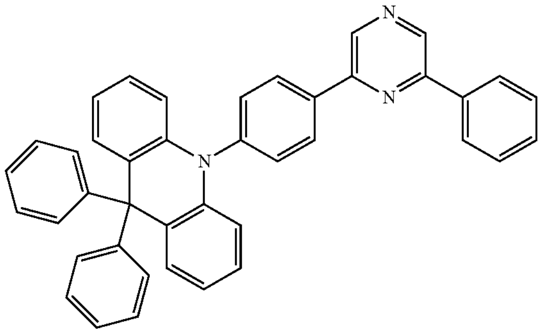
63
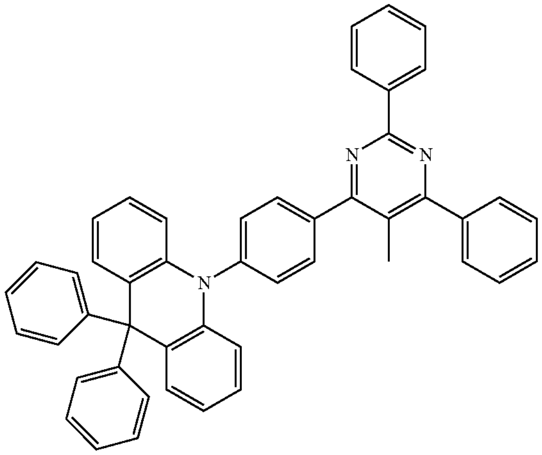
64
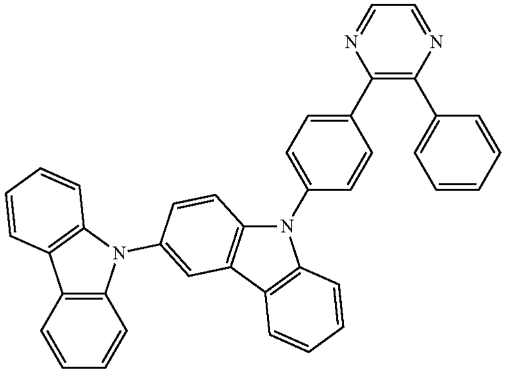
65
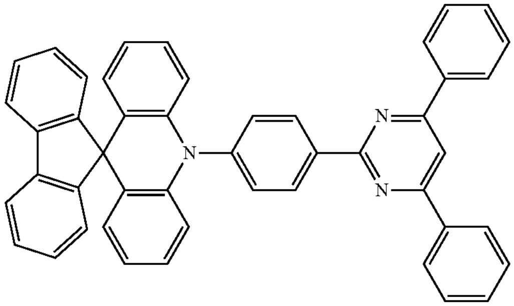
66
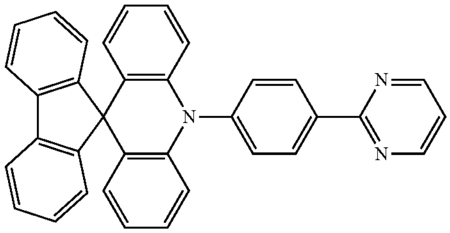
67
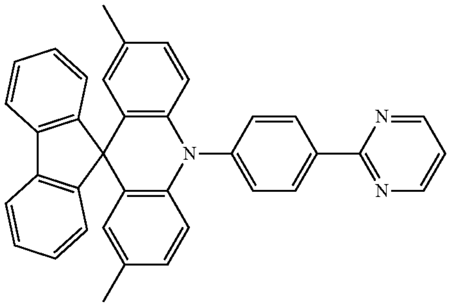
68
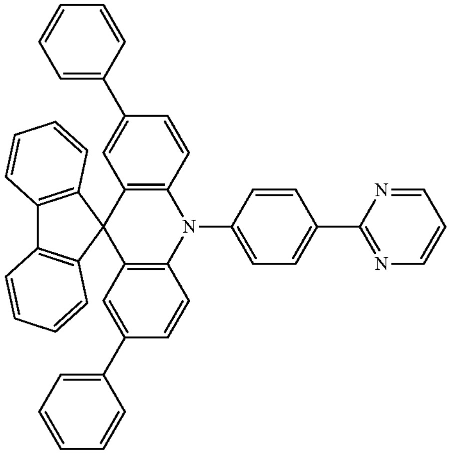
69
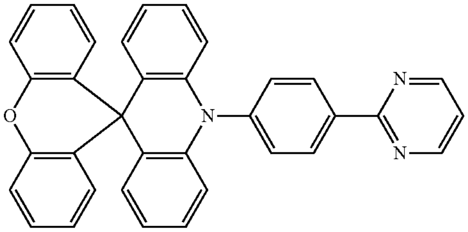

-continued
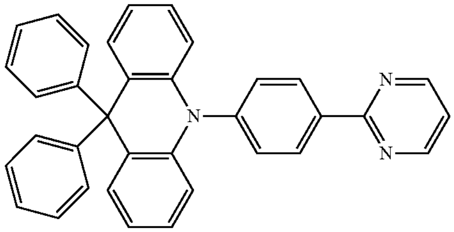
70
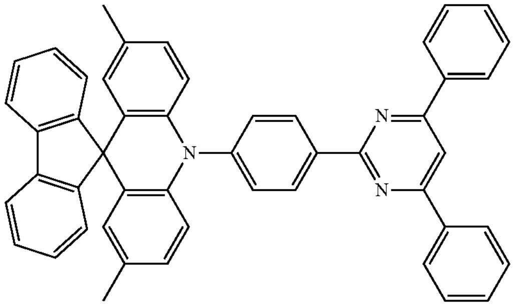
71
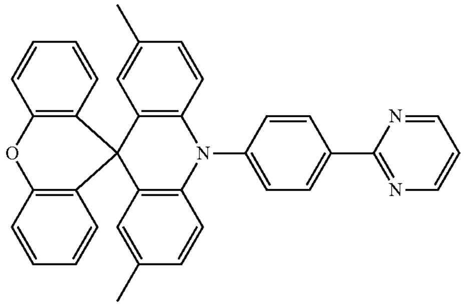
72
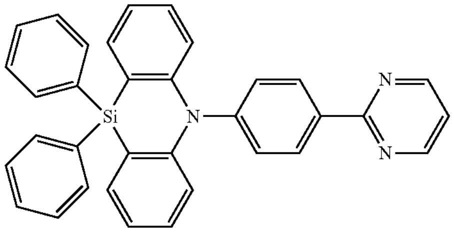
73
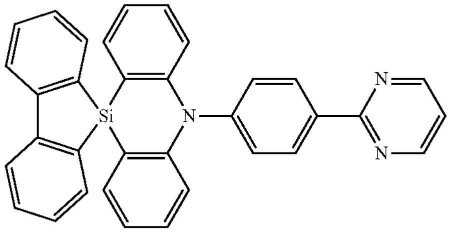
74
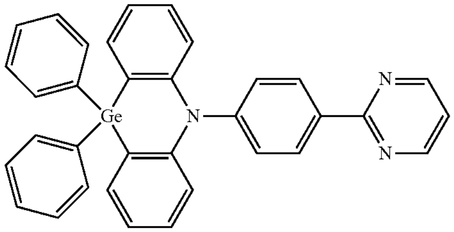
75
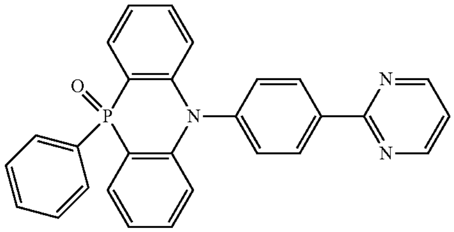
76
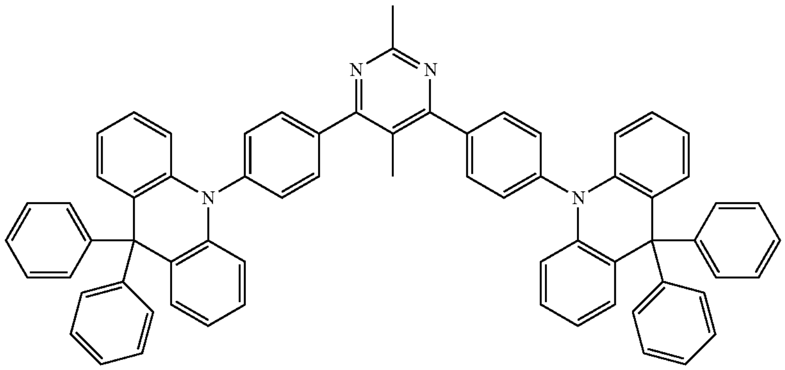
77

-continued
78
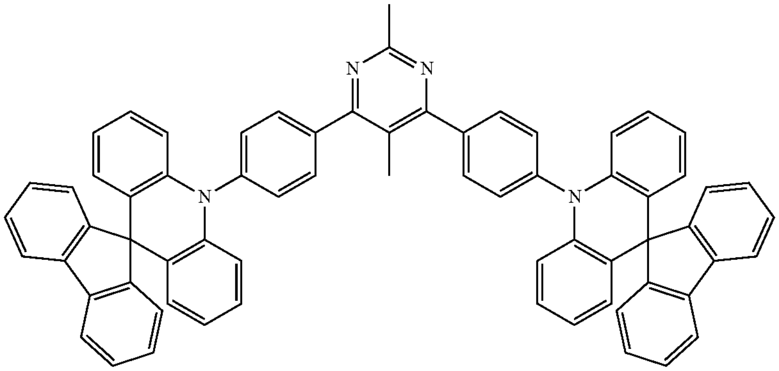
79
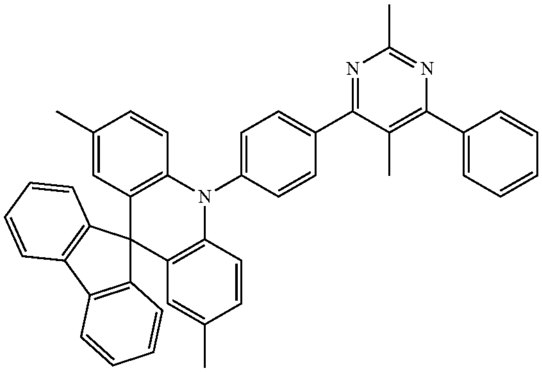
80
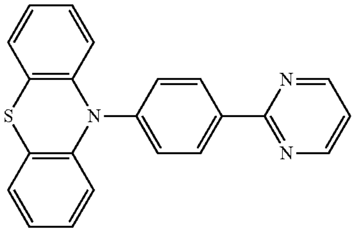
81
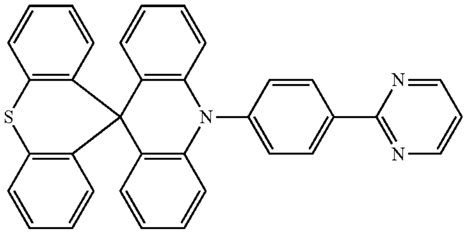
82
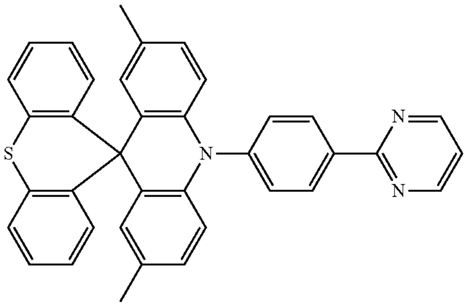
83
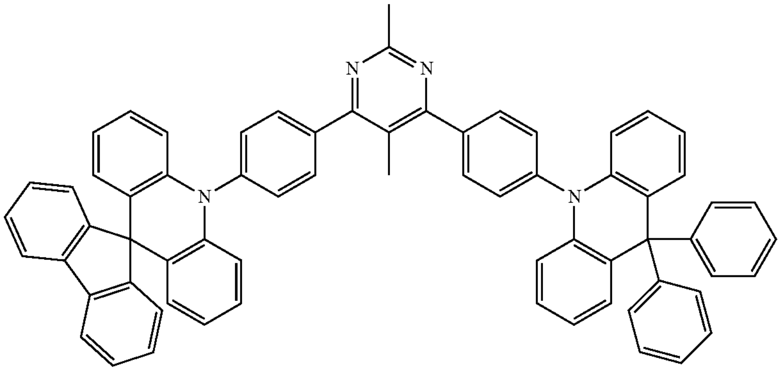

-continued
84
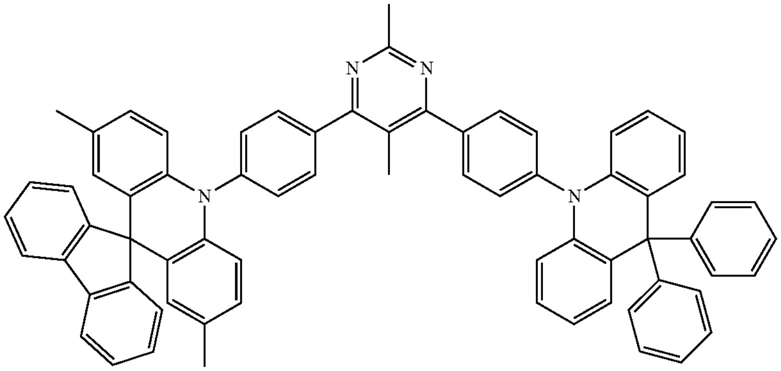
85
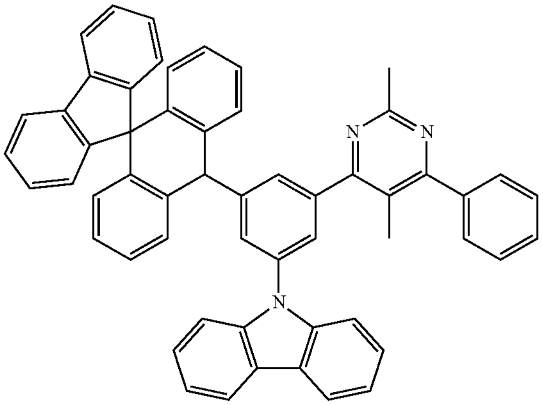
86
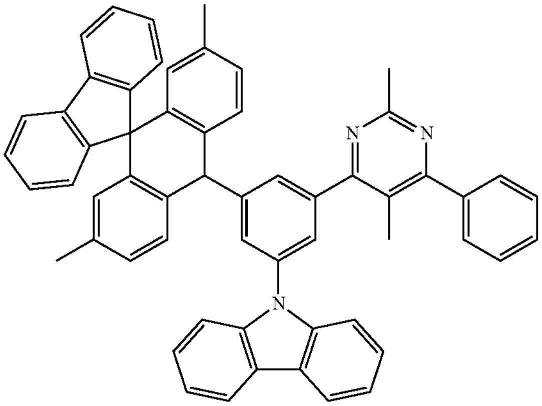
87
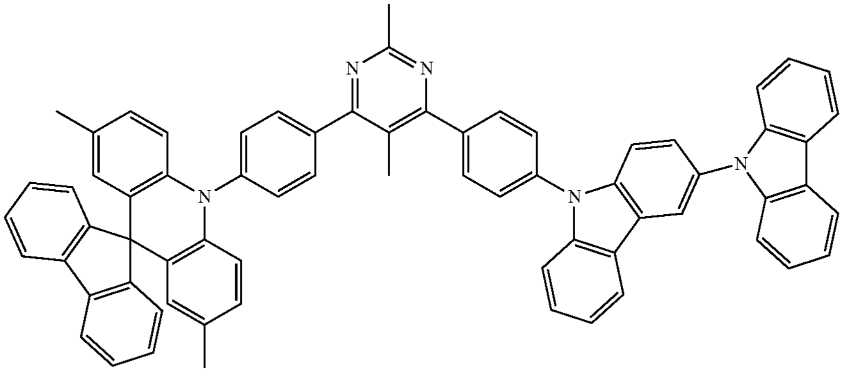
88
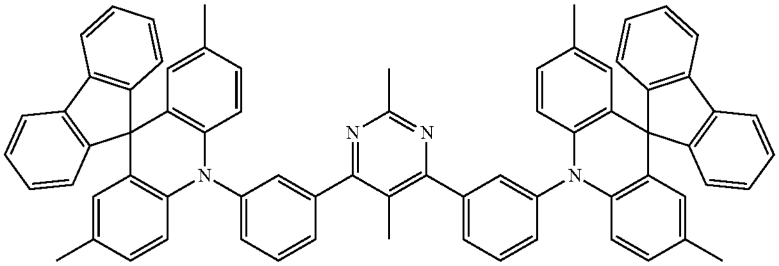

-continued
89
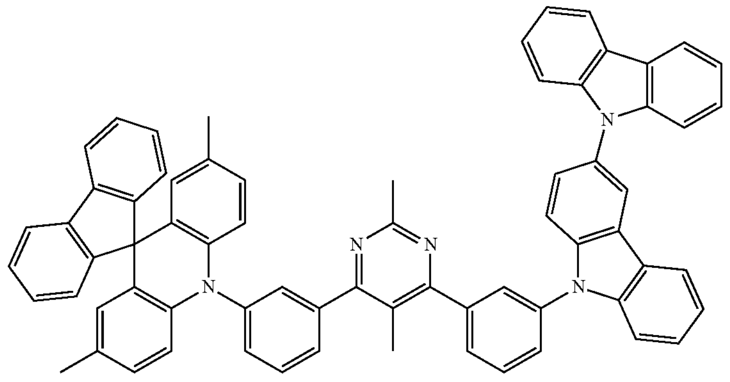
90
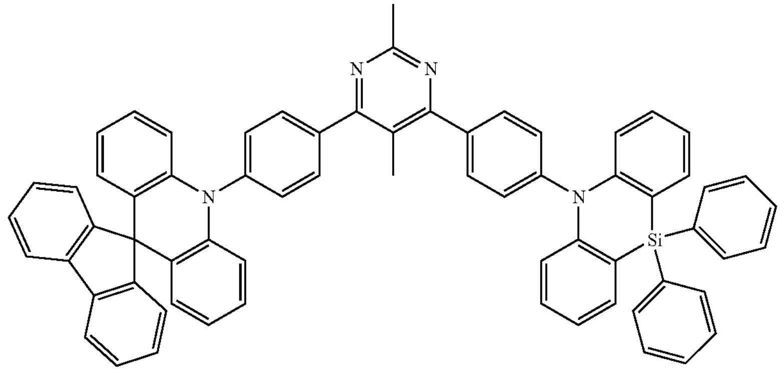
91
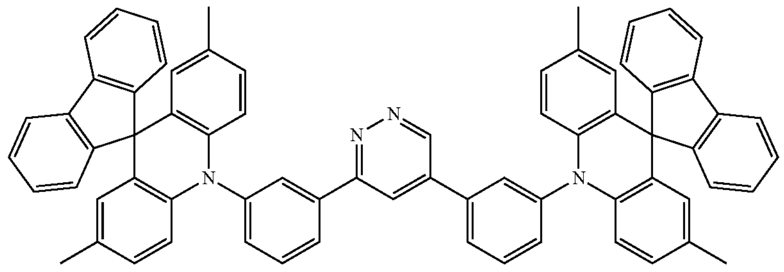
92
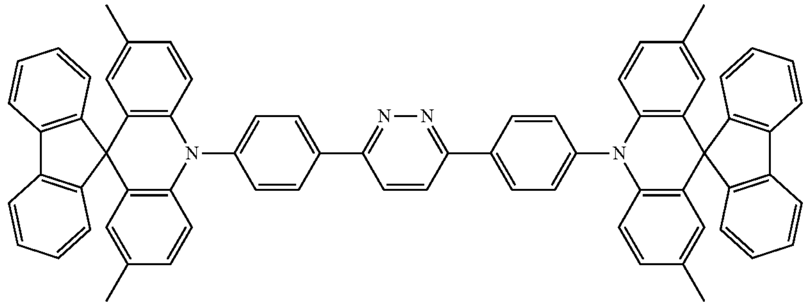

-continued

93

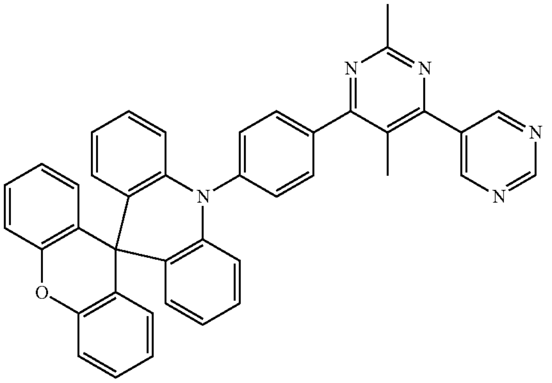

94

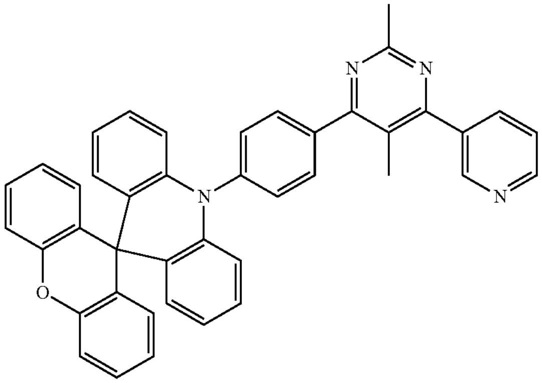

95

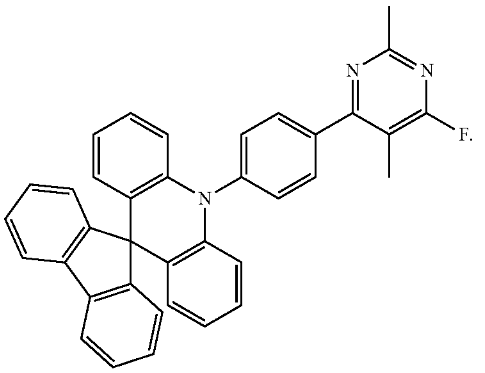

The embodiments may be realized by providing an organic electroluminescence device including a first electrode; a hole transport region on the first electrode; an emission layer on the hole transport region; an electron transport region on the emission layer; and a second electrode on the electron transport region, wherein the emission layer includes a nitrogen-containing compound represented by the following Formula 1:

[Formula 1]

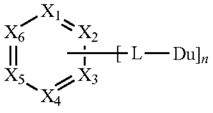

wherein, in Formula 1, $X_1$ to $X_6$ are each independently $CR_1$ or N provided that one or two of $X_1$ to $X_6$ are N, each $R_1$ is independently a bond to L, a hydrogen atom, a deuterium atom, a halogen atom, a substituted or unsubstituted alkyl group having 1 to 30 carbon atoms, a substituted or unsubstituted aryl group having 6 to 30 ring carbon atoms, or a substituted or unsubstituted heteroaryl group having 2 to 30 ring carbon atoms, L is a substituted or unsubstituted arylene group having 6 to 30 ring carbon atoms, n is 1 or 2, and Du is a group represented by the following Formula 2,

[Formula 2]

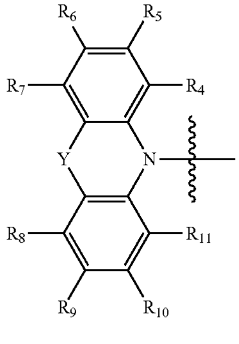

wherein, in Formula 2, Y is a direct linkage, O, S, $CR_2R_3$, Si, Ge, P, or P═O, $R_2$ to $R_{11}$ are each independently a hydrogen atom, a deuterium atom, a substituted or unsubstituted alkyl group having 1 to 30 carbon atoms, a substituted or unsubstituted aryl group having 6 to 30 ring carbon atoms, or a substituted or unsubstituted heteroaryl group of 2 to 30 ring carbon atoms, adjacent ones of $R_2$ to $R_{11}$ are separate or are combined to form a ring, and

represents a bonding site with L of Formula 1.

An absolute value of a difference between a singlet energy level and a triplet energy level of the nitrogen-containing compound represented by Formula 1 may be about 0.2 eV or less.

L may be a substituted or unsubstituted phenylene group.

The nitrogen-containing compound represented by Formula 1 may be represented by the following Formula 3:

[Formula 3]

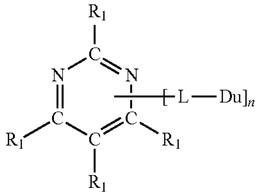

wherein, in Formula 3, L, Du, $R_1$, and n are defined the same as those of Formula 1.

The nitrogen-containing compound represented by Formula 1 may be represented by the following Formula 4:

[Formula 4]

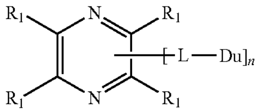

wherein, in Formula 4, L, Du, $R_1$, and n are defined the same as those of Formula 1.

The nitrogen-containing compound represented by Formula 1 may be represented by the following Formula 5:

[Formula 5]

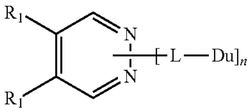

wherein, in Formula 5, L, Du, $R_1$, and n are defined the same as those of Formula 1.

Y may be the direct linkage or $CR_2R_3$.

The nitrogen-containing compound represented by the above Formula 1 may be represented by the following Formula 6:

[Formula 6]

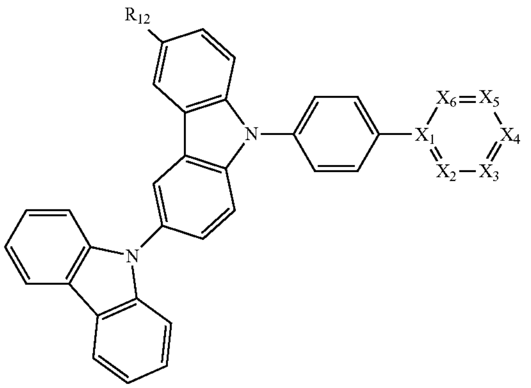

wherein, in Formula 6, $R_{12}$ is a hydrogen atom or a substituted or unsubstituted carbazole group, and $X_1$ to $X_6$ are defined the same as those of Formula 1.

The group represented by Formula 2 may be represented by one of the following Formulae 7 to 16, in which

is defined the same as that of Formula 2:

[Formula 7]

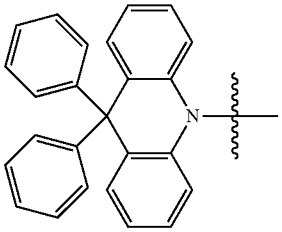

[Formula 8]

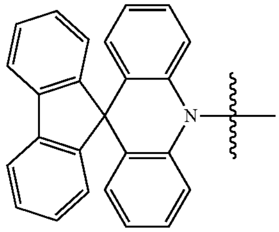

[Formula 9]

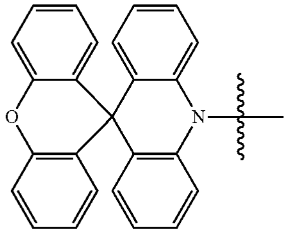

[Formula 10]

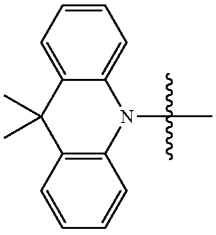

[Formula 11]

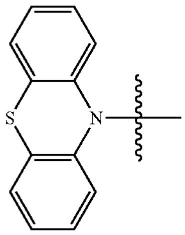

[Formula 12]

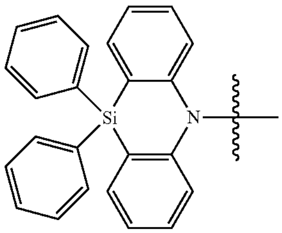

-continued
[Formula 13]
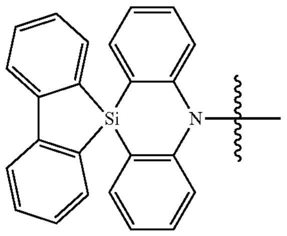
[Formula 14]
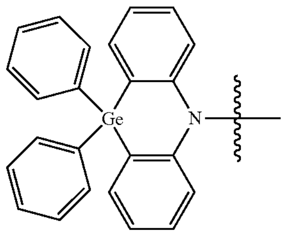
-continued
[Formula 15]
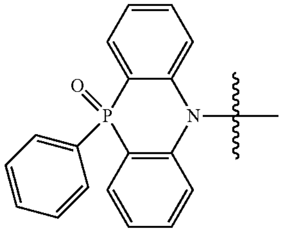
[Formula 16]
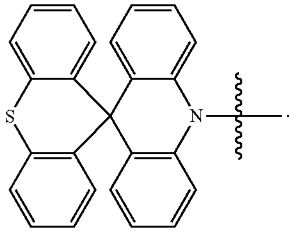
The nitrogen-containing compound represented by Formula 1 may be one of the following Compounds 1 to 95:
1
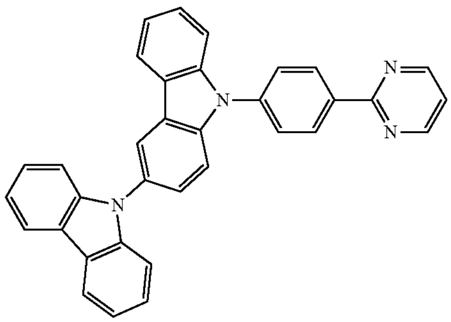
2
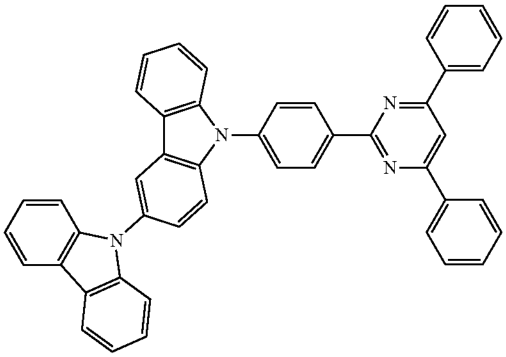
3
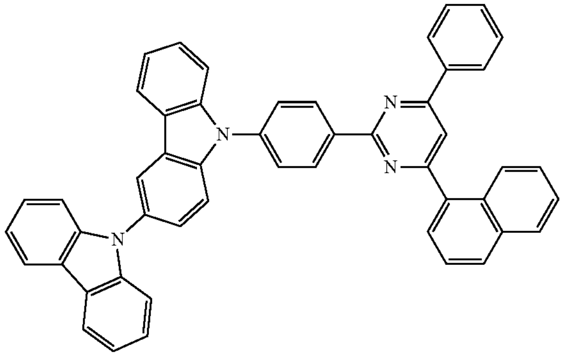
4
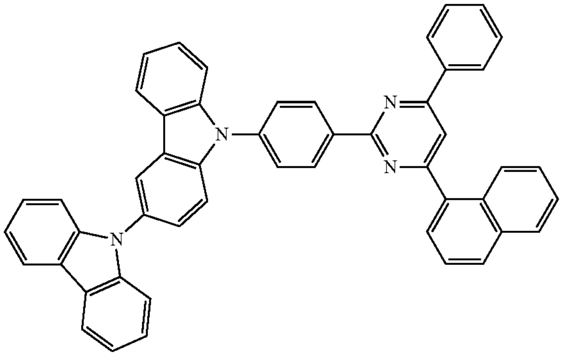
5
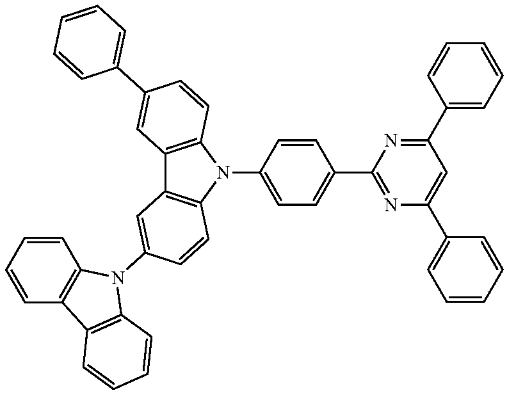
6
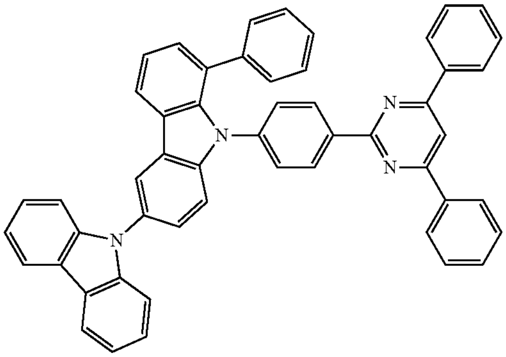

-continued
7
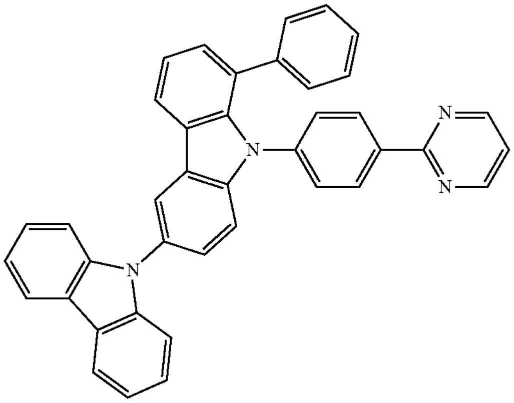
8
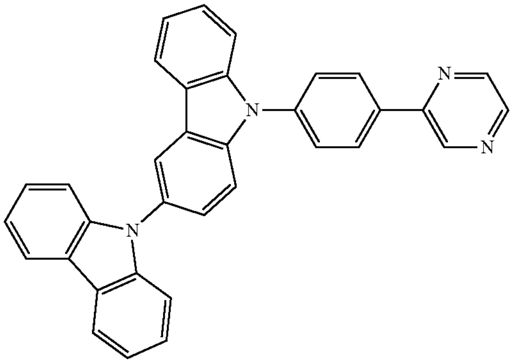
9
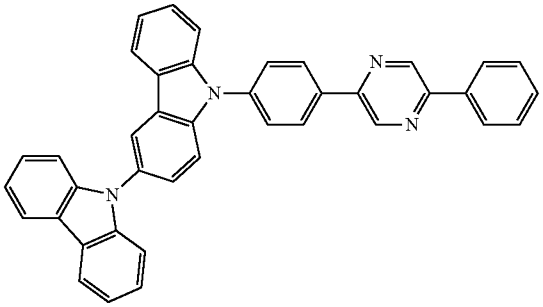
10
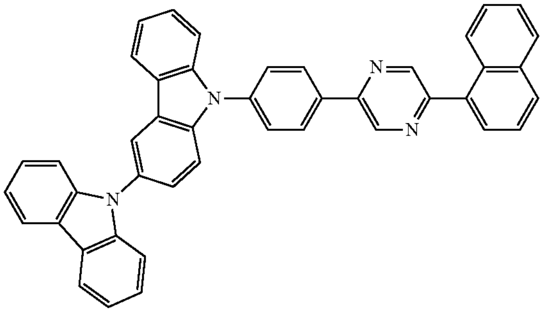
11
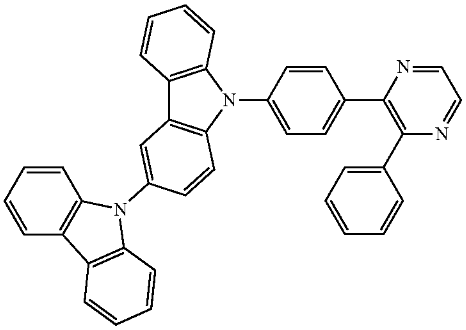
12
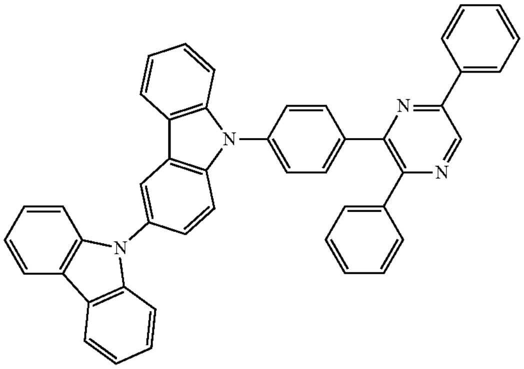
13
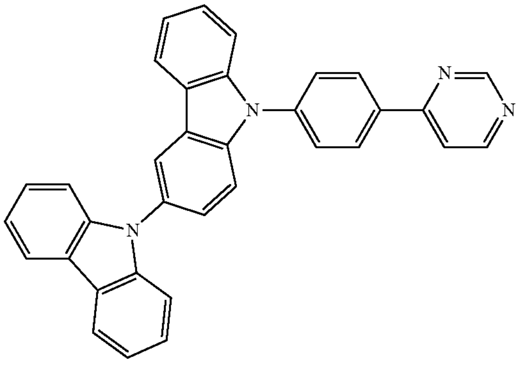
14
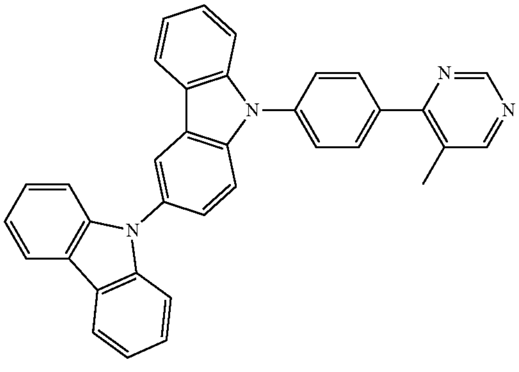

-continued
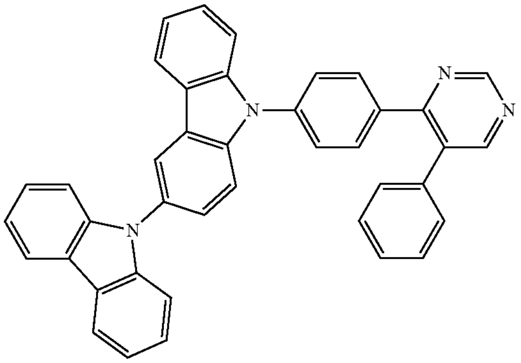
15
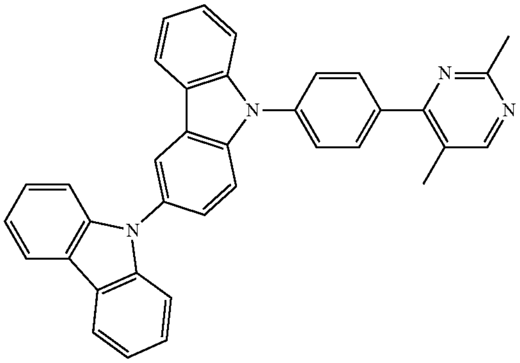
16
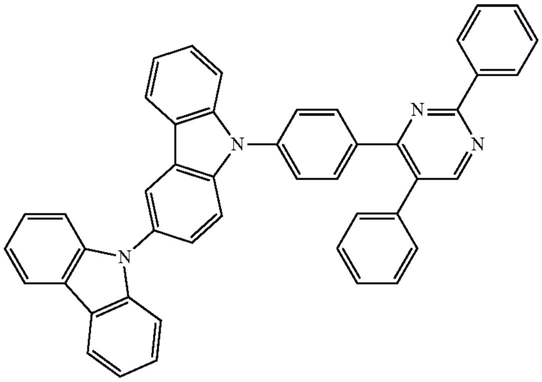
17
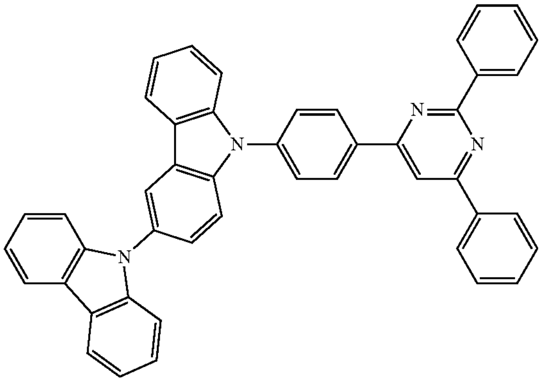
18
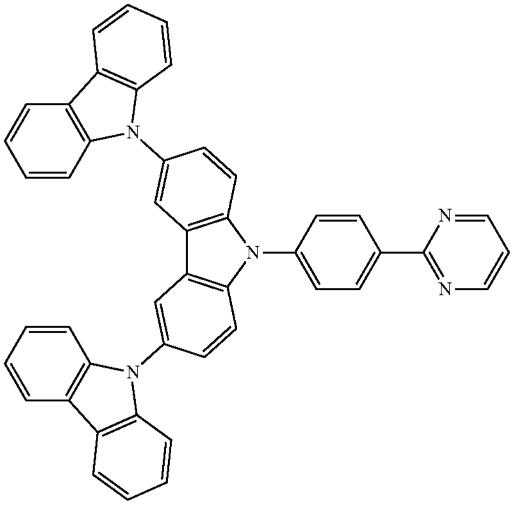
19
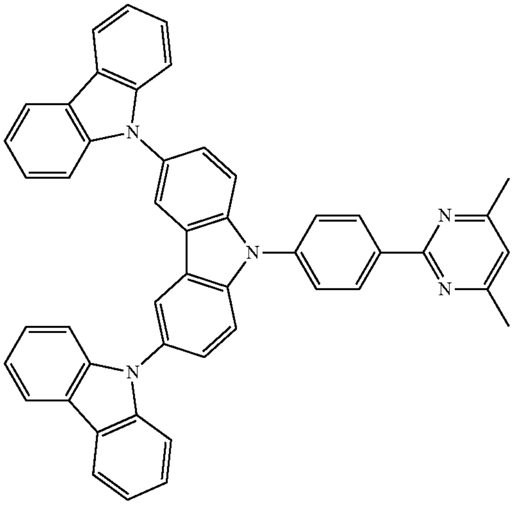
20

-continued
21
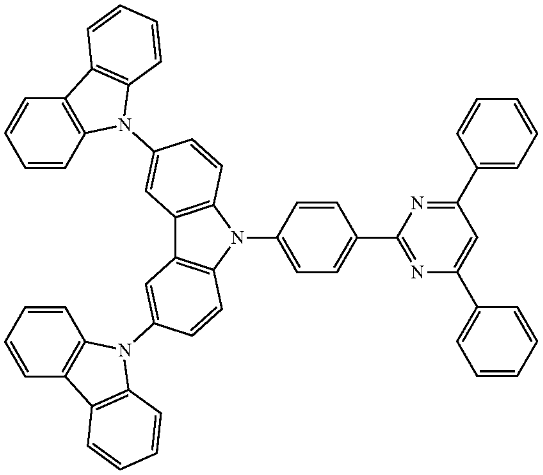
22
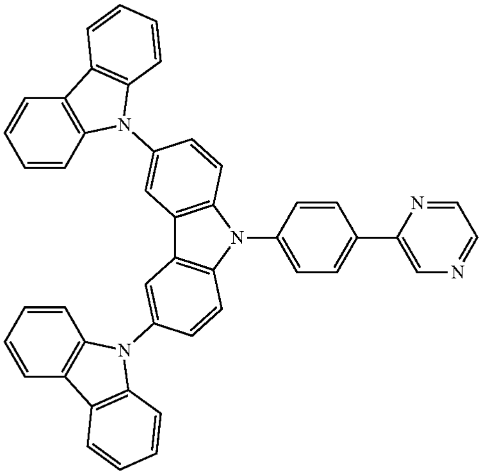
23
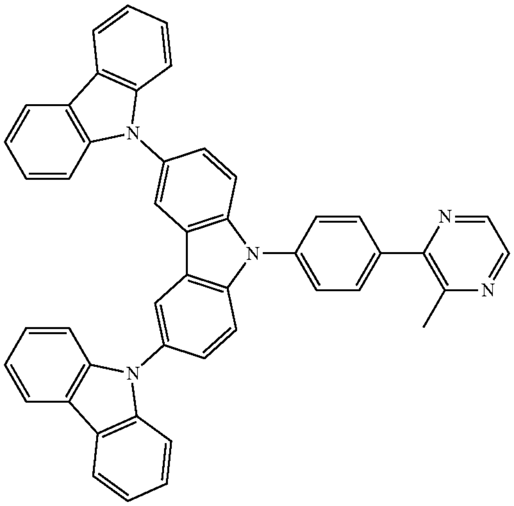
24
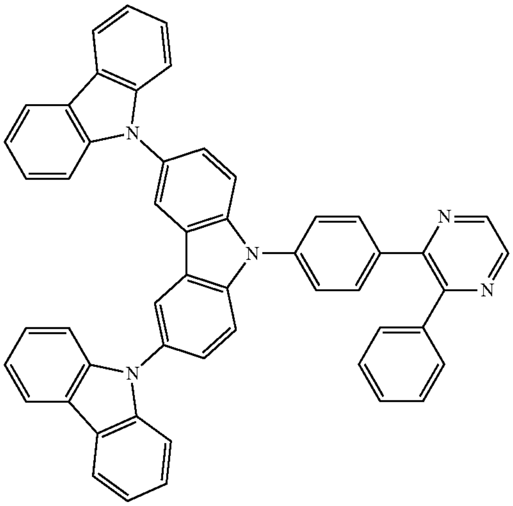
25
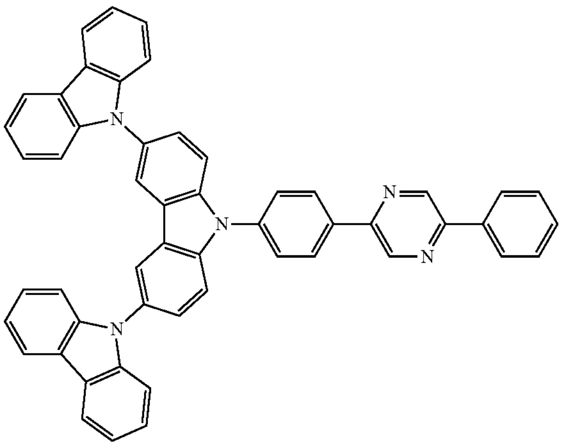
26
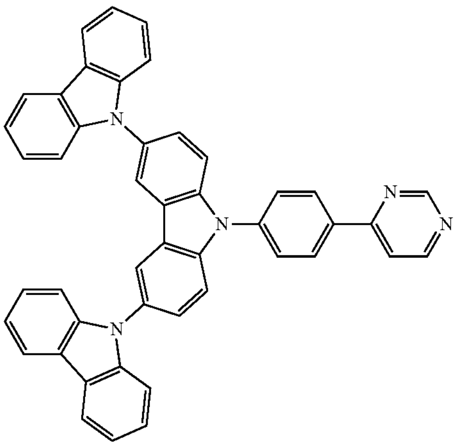

-continued
27
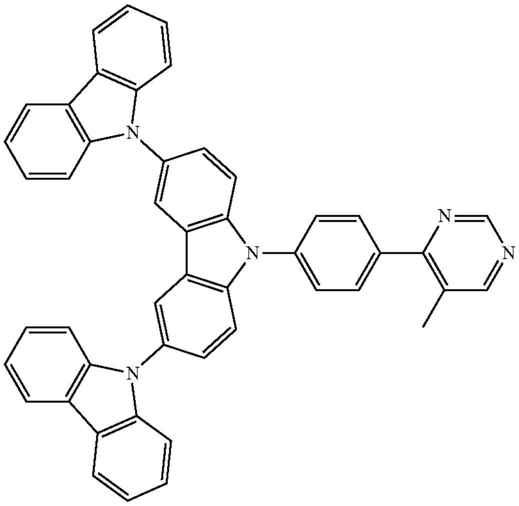
28
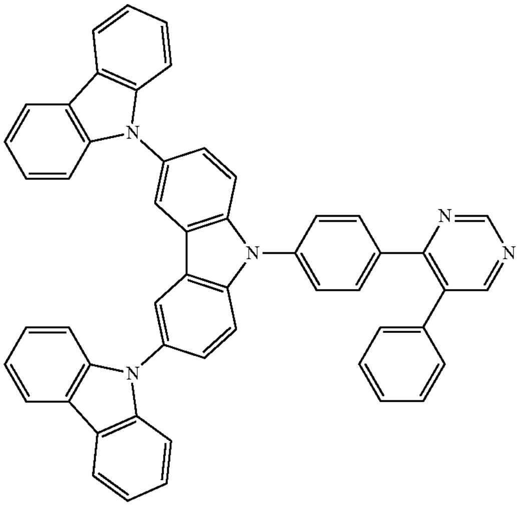
29
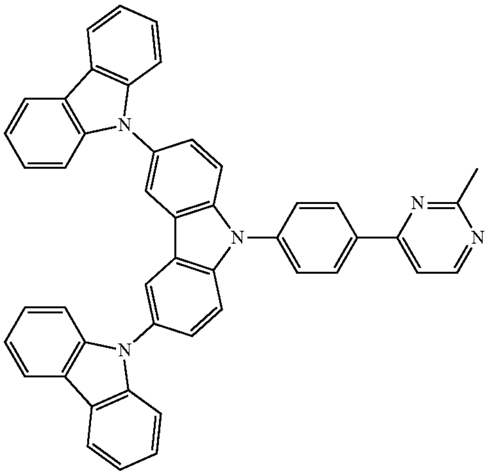
30
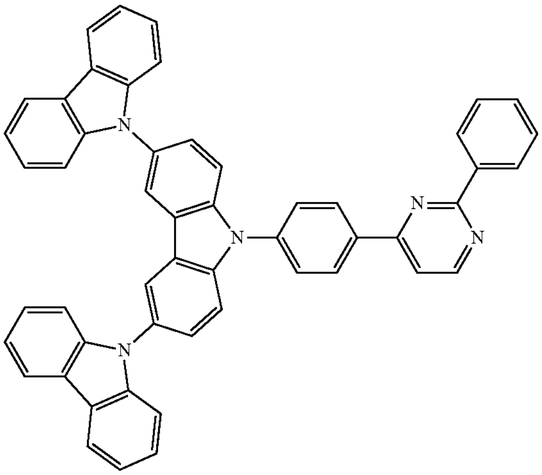
31
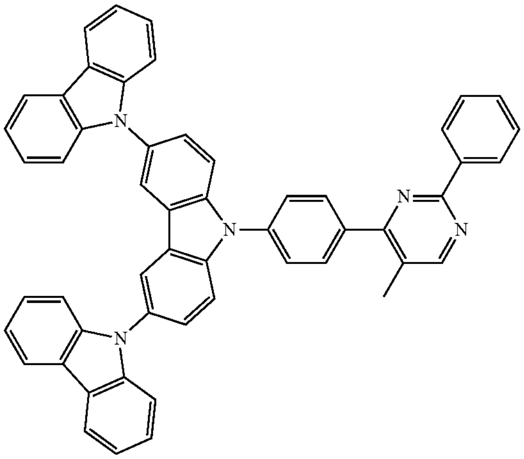
32
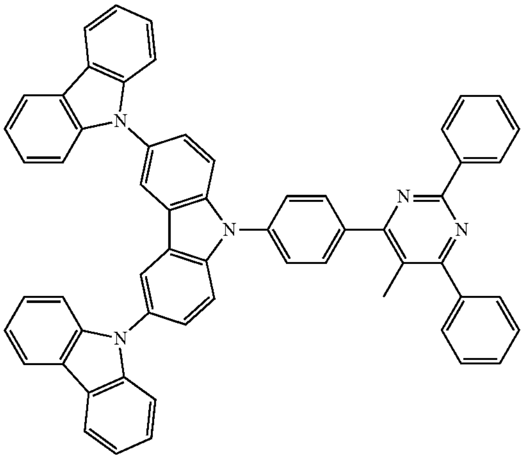

-continued
33
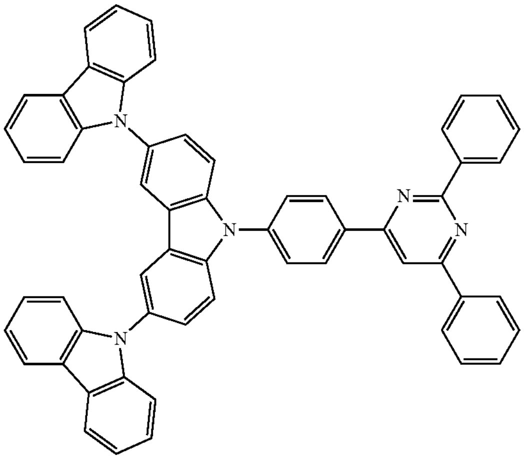
34
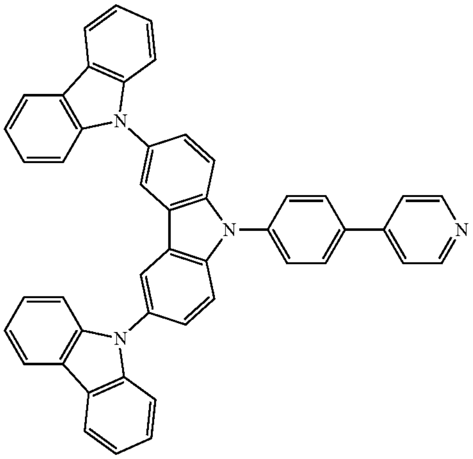
35
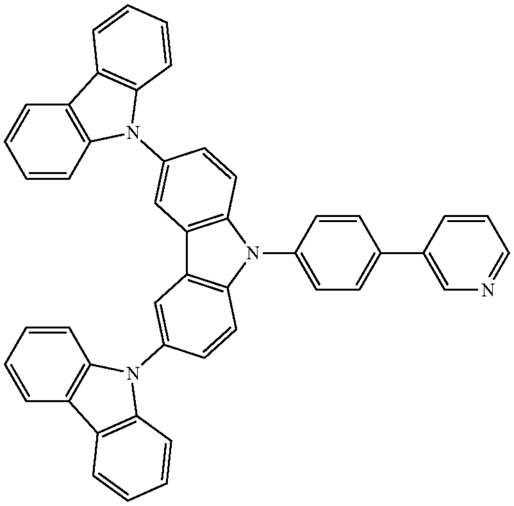
36
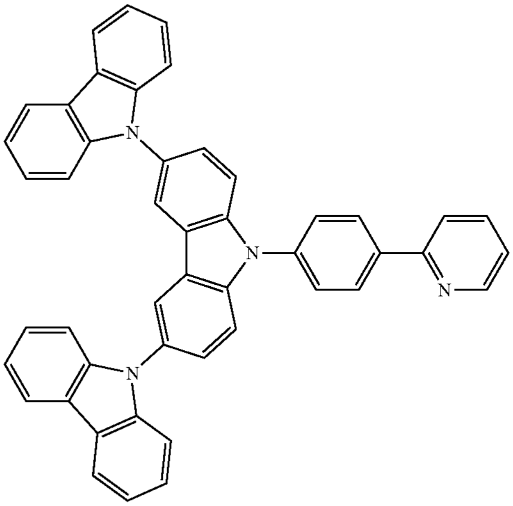
37
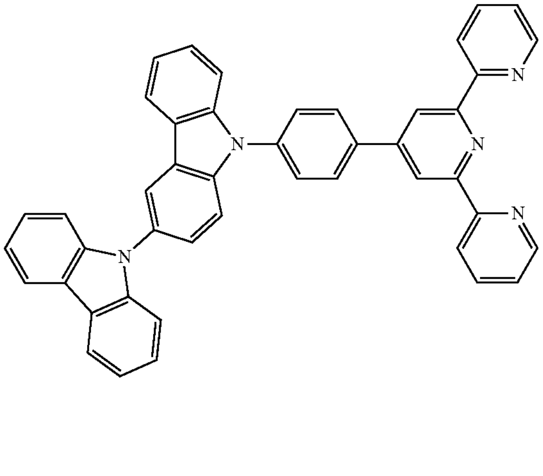
38
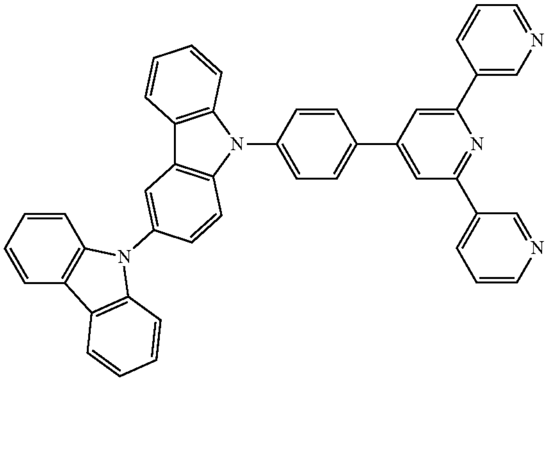

-continued
39
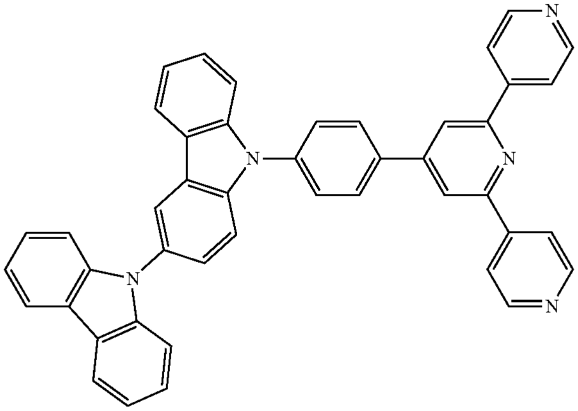
40
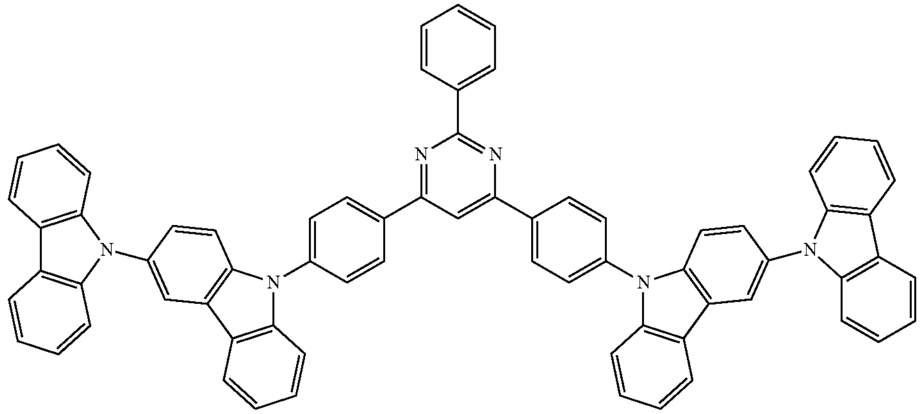
41
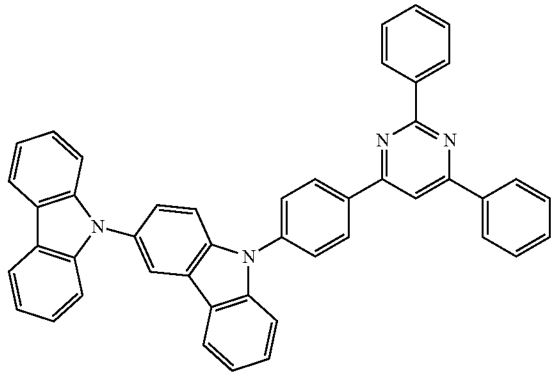
42
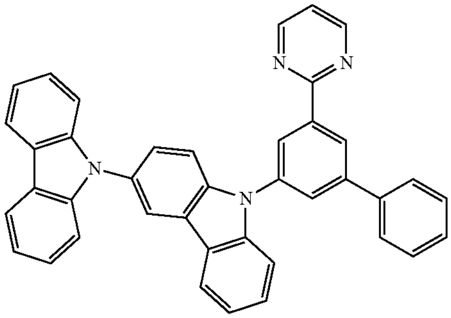
43
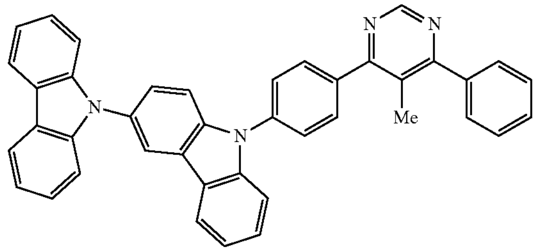
44
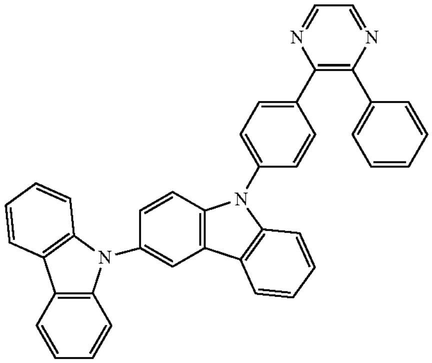

-continued
45
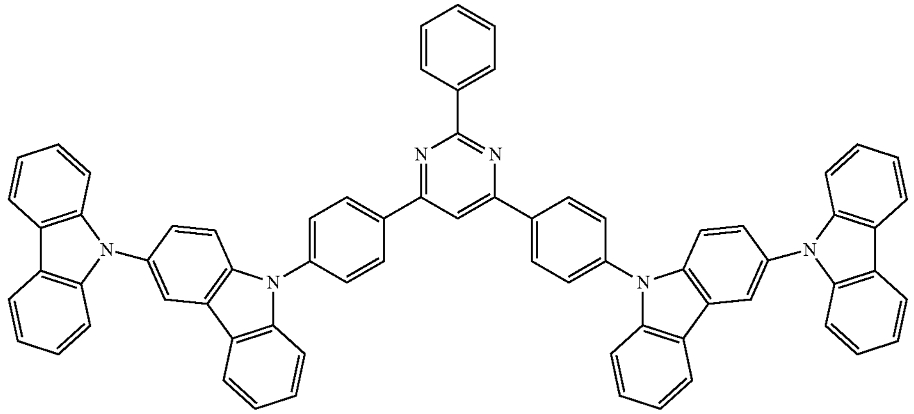
46
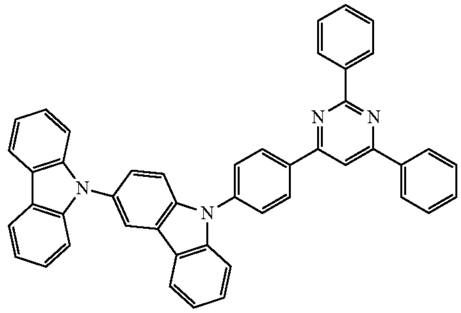
47
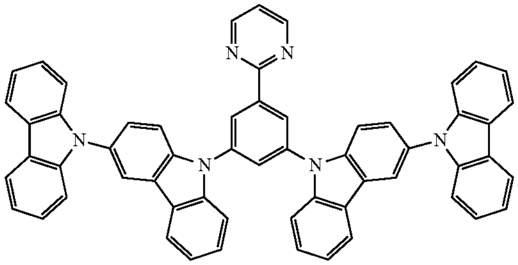
48
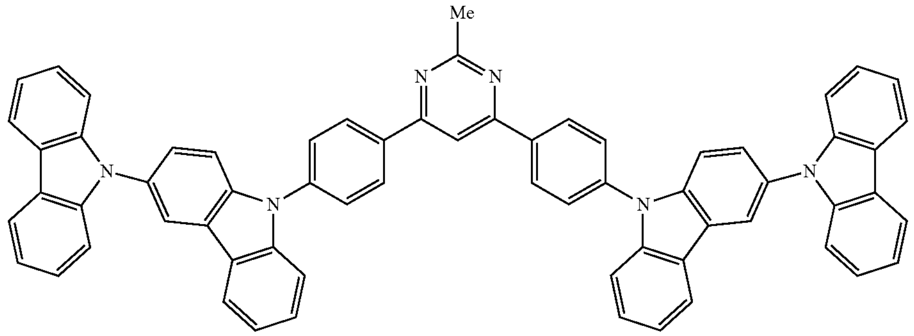
49
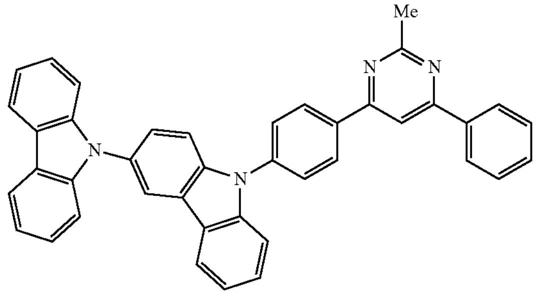

-continued
50
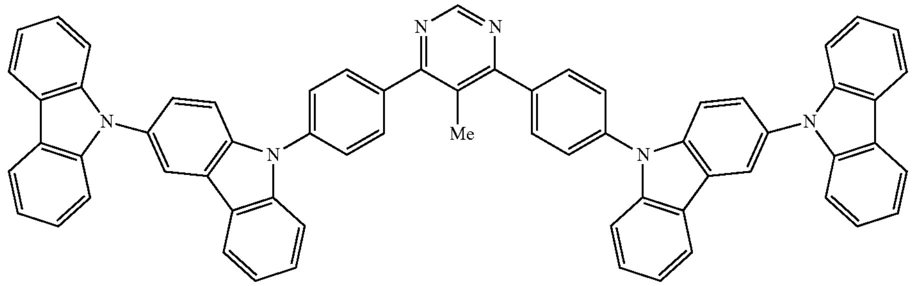
51
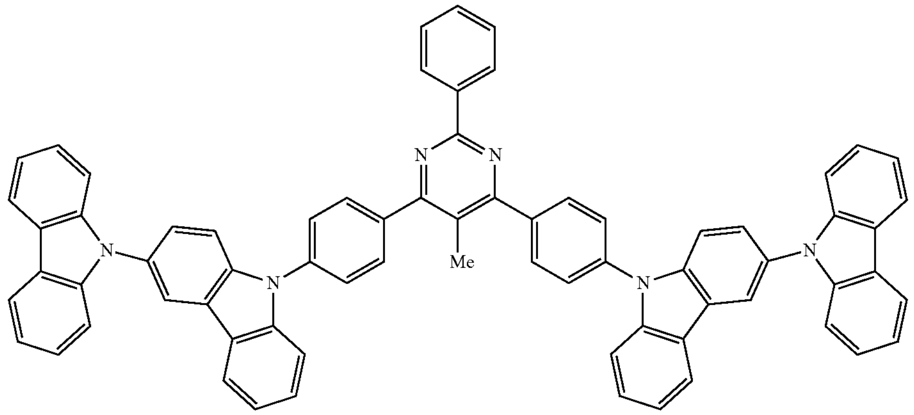
52
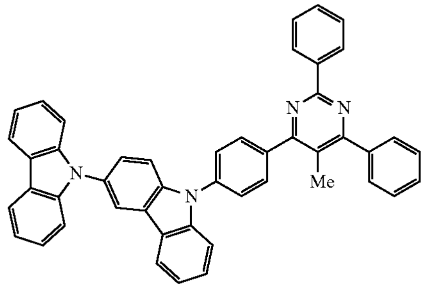
53
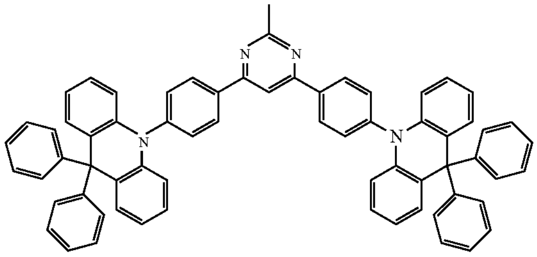
54
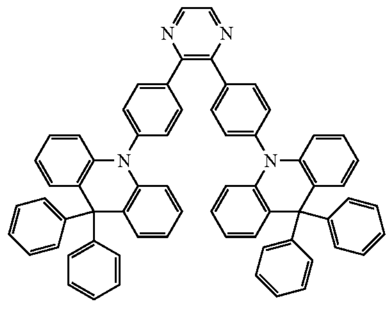
55
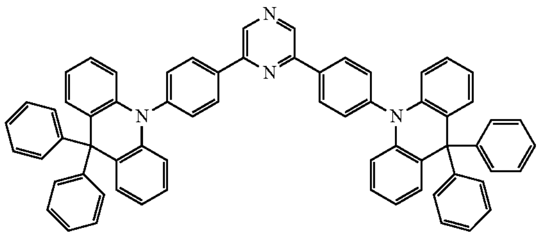
56
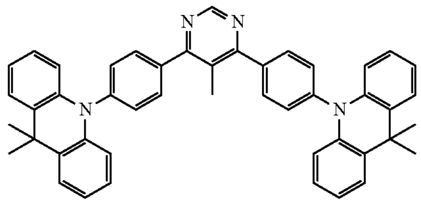
57
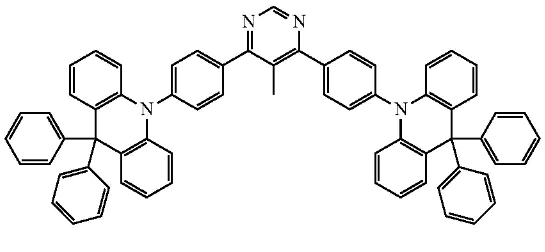

-continued
58
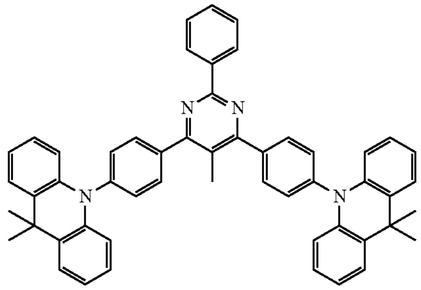
59
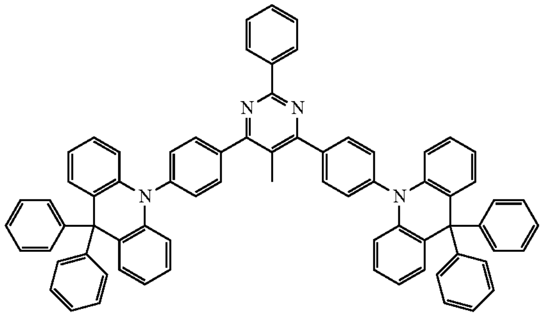
60
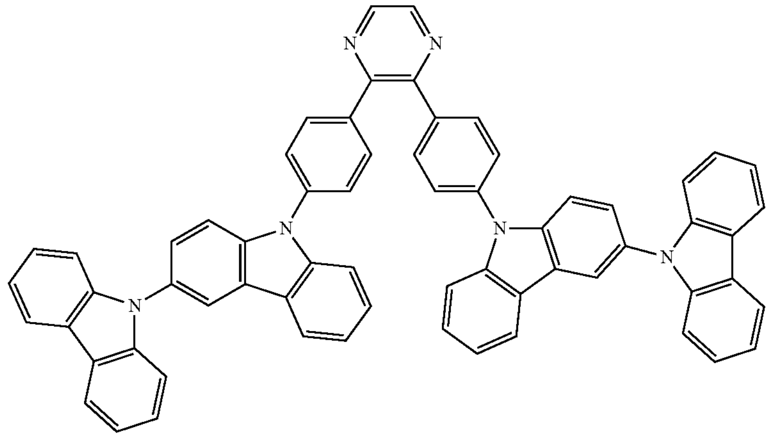
61
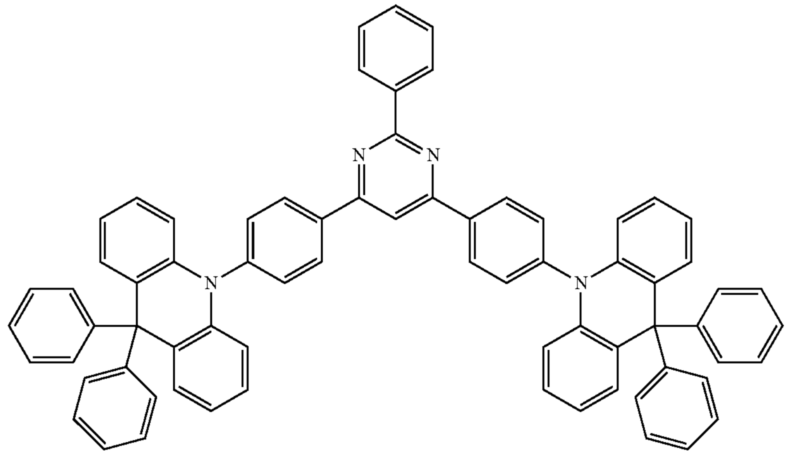
62
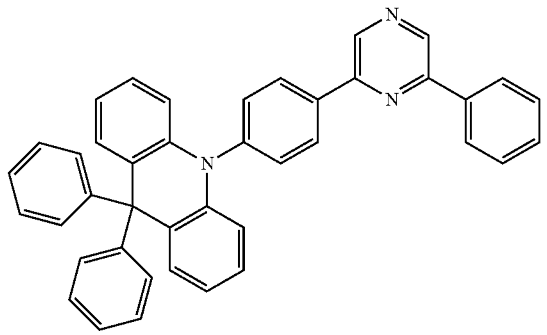
63
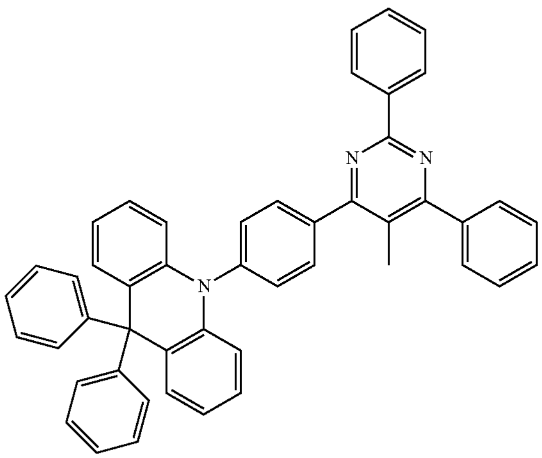

-continued
64
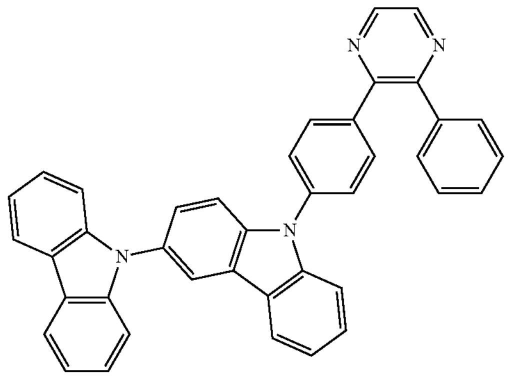
65
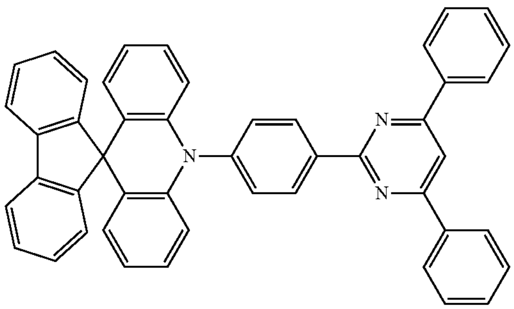
66
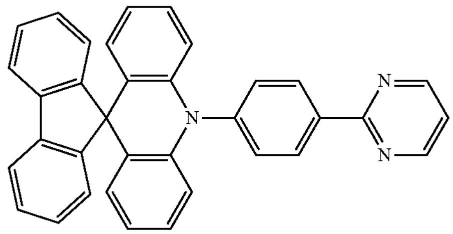
67
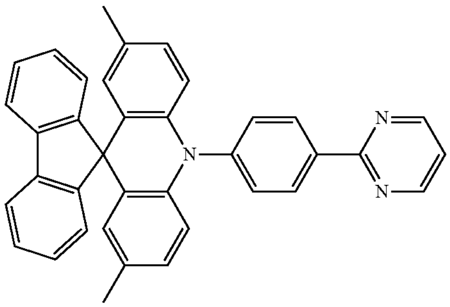
68
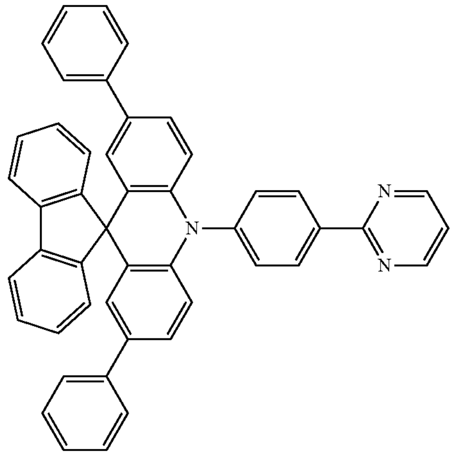
69
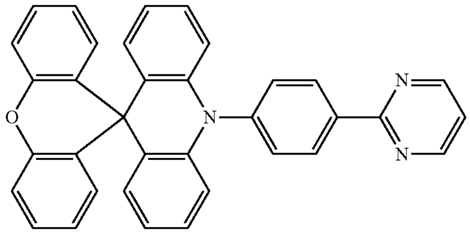
70
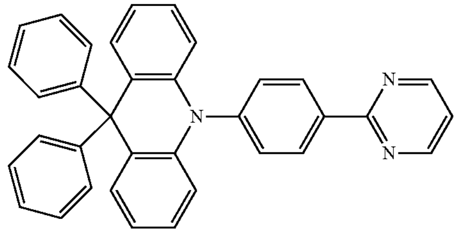
71
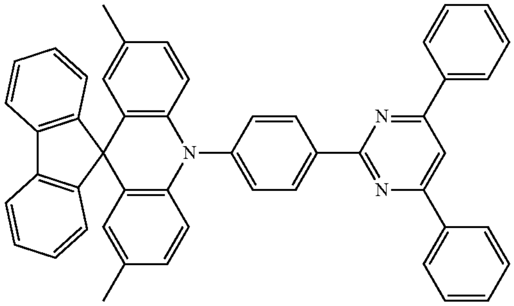

-continued
72
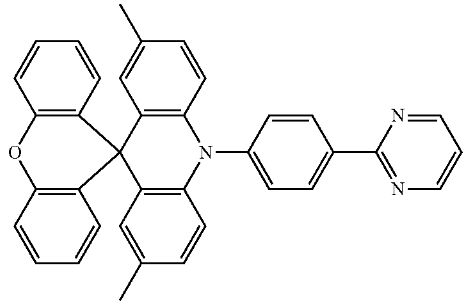
73
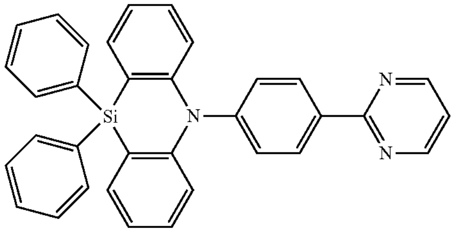
74
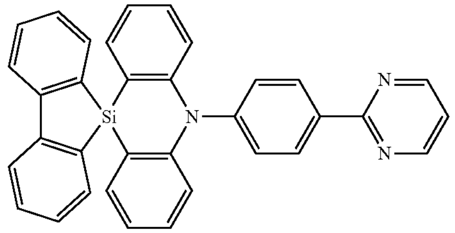
75
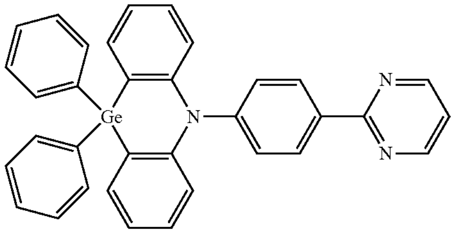
76
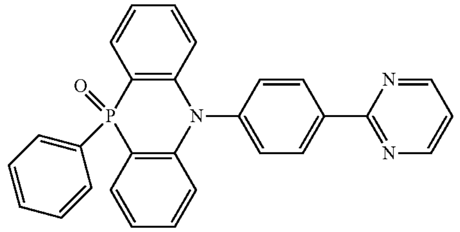
77
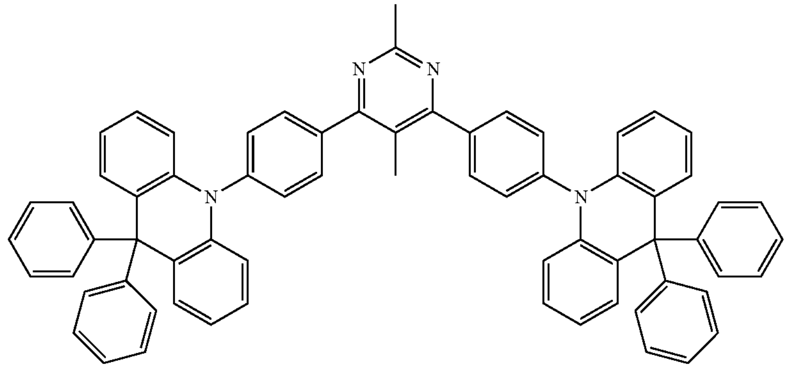
78
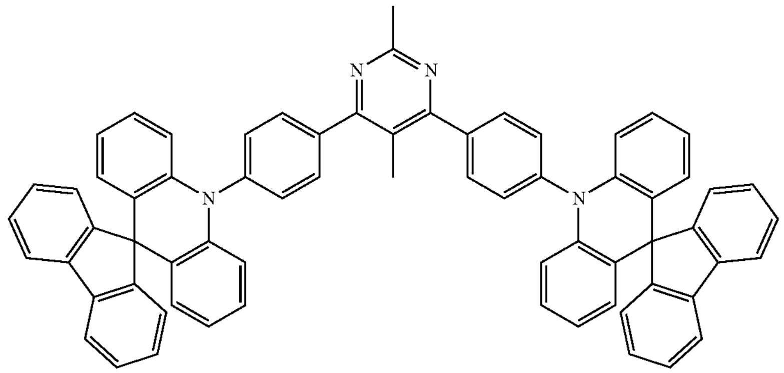

-continued
79
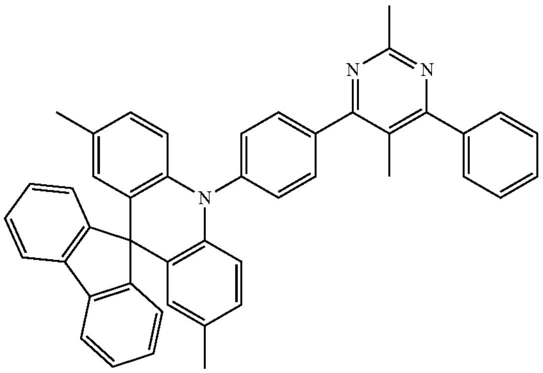
80
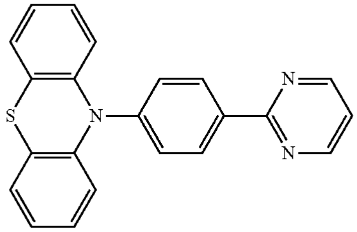
81
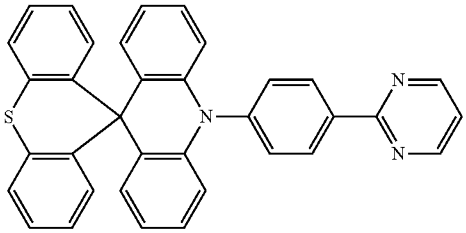
82
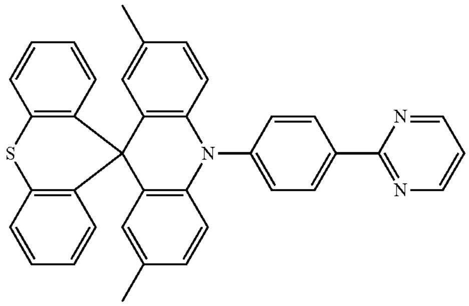
83
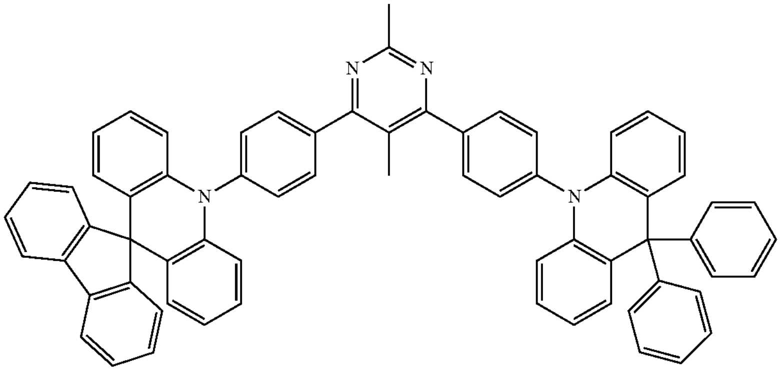
84
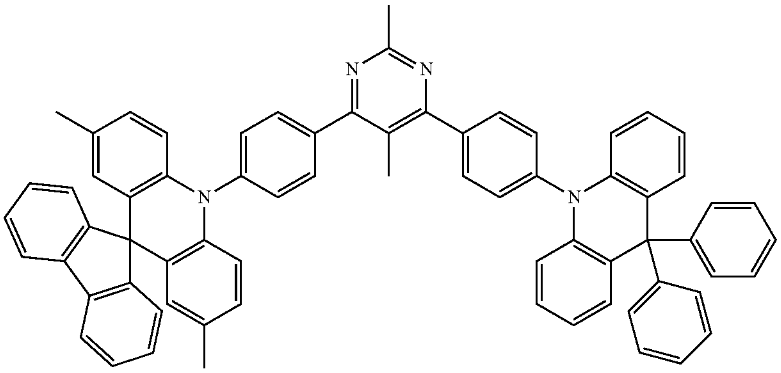

-continued
85
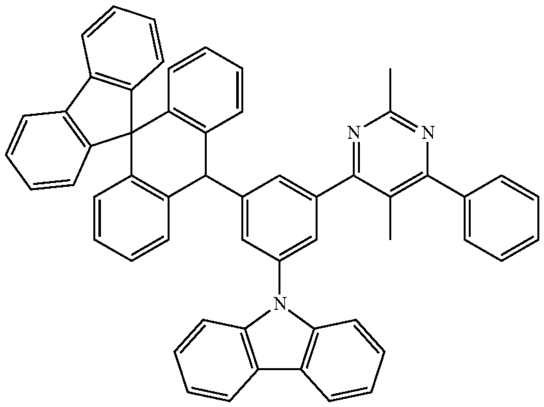
86
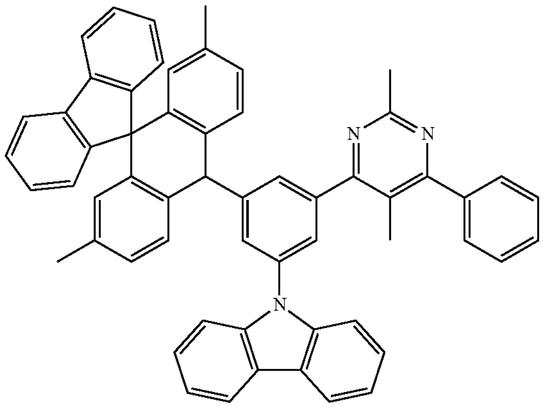
87
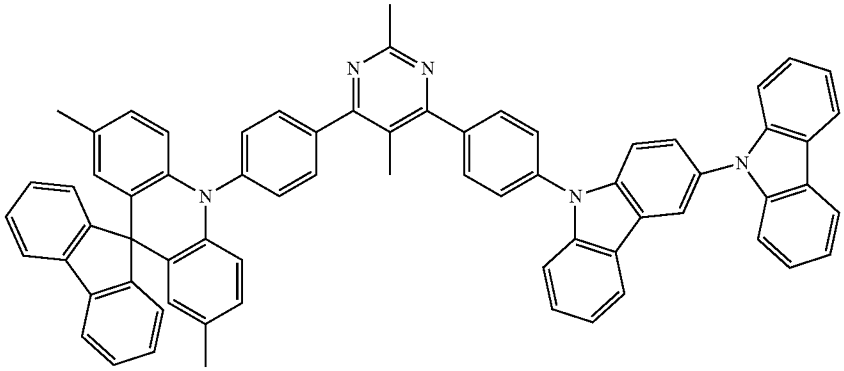
88
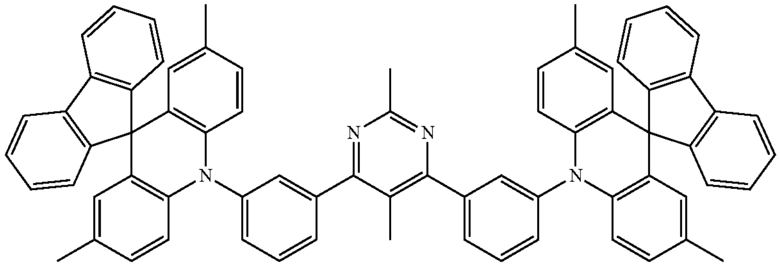
89
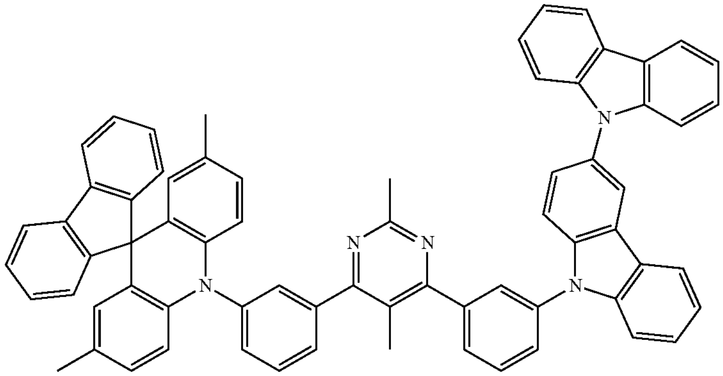

-continued
90
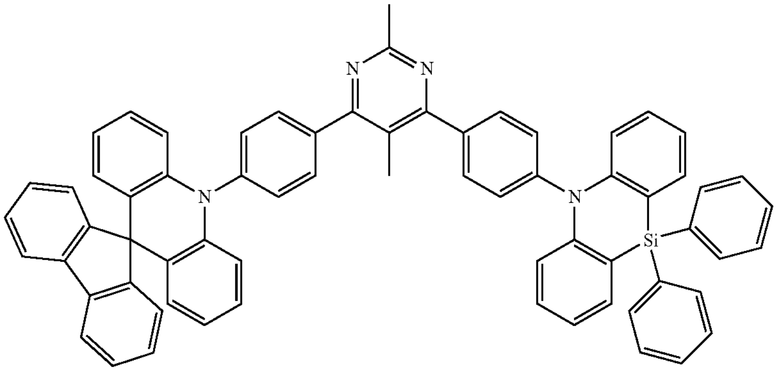
91
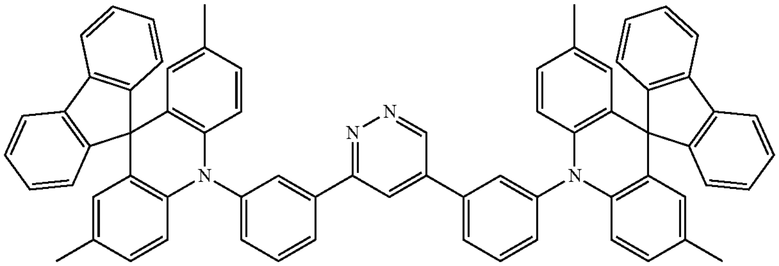
92
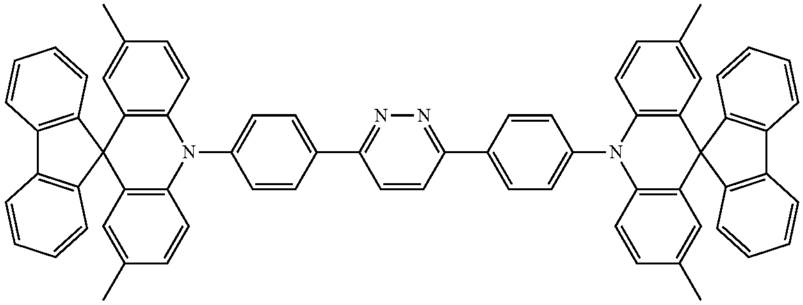
93
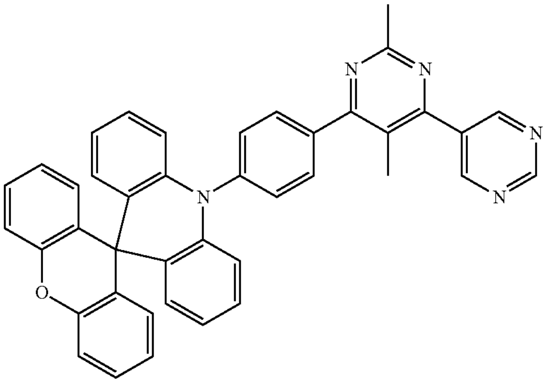
94
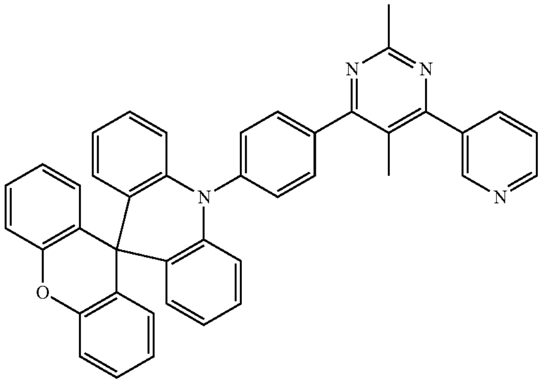

-continued

95

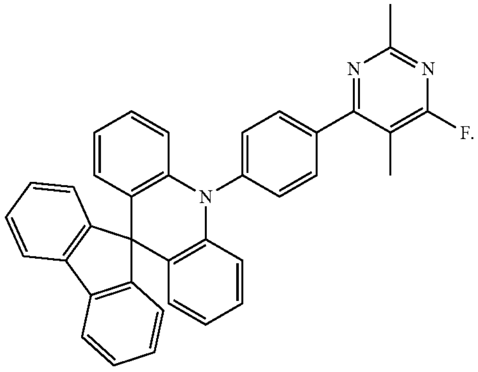

The hole transport region may include a hole injection layer and a hole transport layer, and the electron transport region may include an electron injection layer and an electron transport layer.

The embodiments may be realized by providing a nitrogen-containing compound represented by the following Formula 1':

[Formula 1']

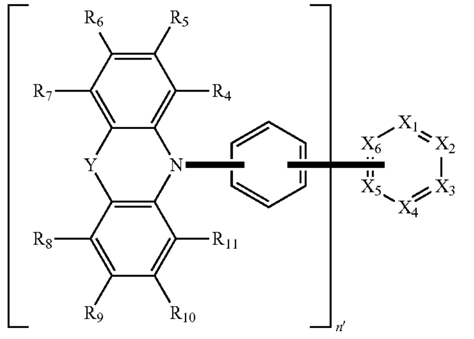

wherein, in Formula 1', $X_1$ to $X_6$ are each independently $CR_1$ or N, provided that two of $X_1$ to $X_6$ are N, each $R_1$ is independently a single bond, a hydrogen atom, a methyl group, or a phenyl group, n' is 1 or 2, Y is a $CR_2R_3$, $R_2$ to $R_{11}$ are each independently a hydrogen atom, a methyl group, or a substituted or unsubstituted phenyl group, and $R_2$ and $R_3$ are separate or are combined to form a ring.

The nitrogen-containing compound represented by Formula 1' may be one of the following Compounds 53, 55, 61, 66, 67, 69, 70, or 71:

53

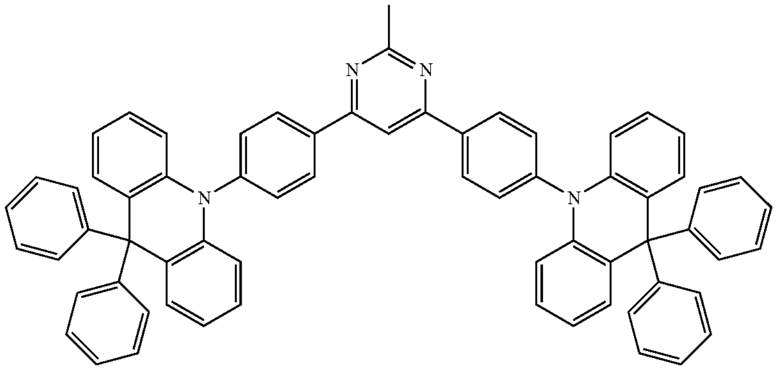

-continued
55
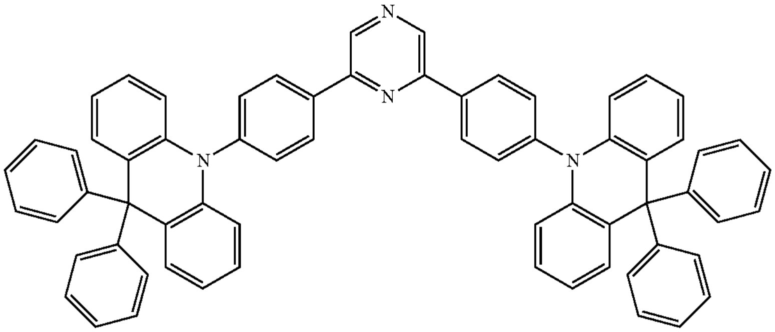
61
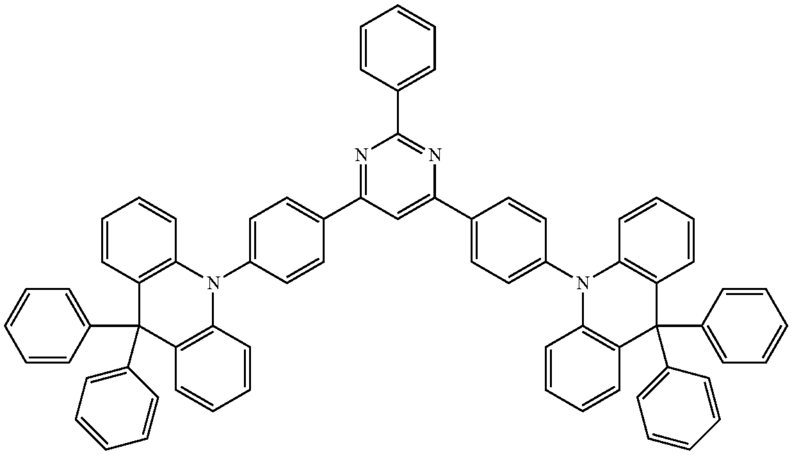
67
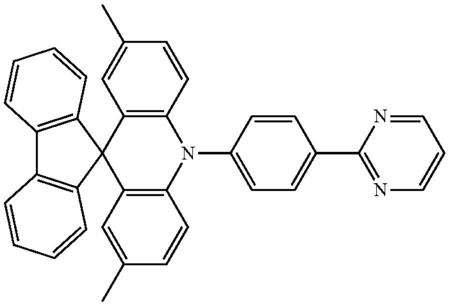
71
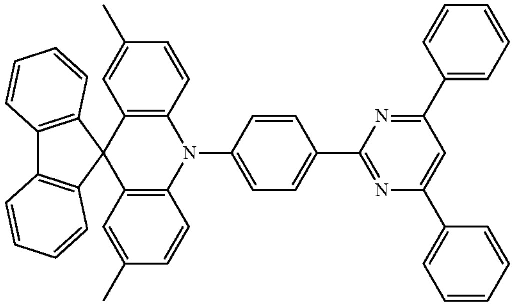
66
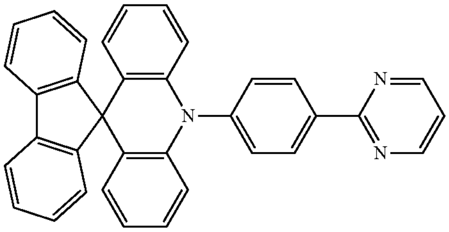
69
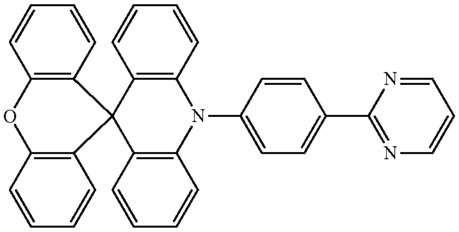
70
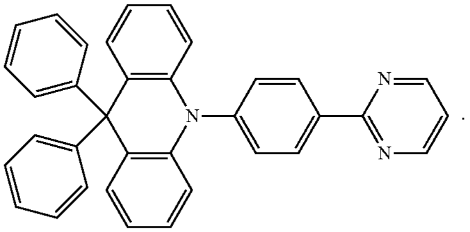

The embodiments may be realized by providing an organic electroluminescence device including a first electrode; a hole transport region on the first electrode; an emission layer on the hole transport region; an electron transport region on the emission layer; and a second electrode on the electron transport region, wherein the emission layer includes the nitrogen-containing compound according to an embodiment.

An absolute value of a difference between a singlet energy level and a triplet energy level of the nitrogen-containing compound may be about 0.2 eV or less.

The nitrogen containing compound may be a dopant in the emission layer.

BRIEF DESCRIPTION OF THE DRAWINGS

Features will be apparent to those of skill in the art by describing in detail exemplary embodiments with reference to the attached drawings in which.

DETAILED DESCRIPTION

Figure 1:
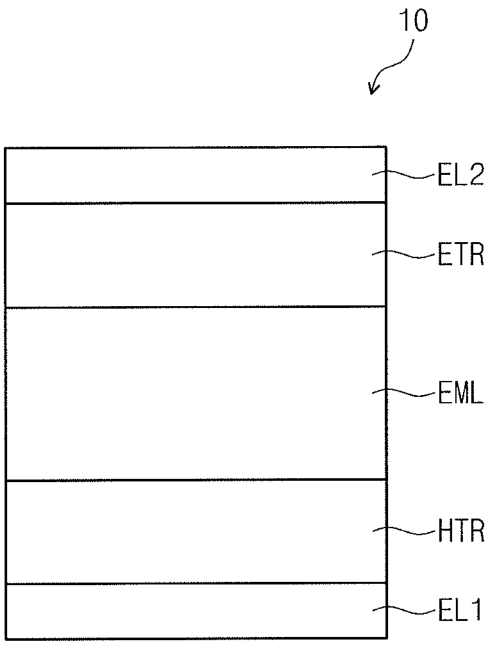
FIG. 1 illustrates a cross-sectional view schematically showing an organic electroluminescence device according to an embodiment.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

Like reference numerals refer to like elements for explaining each drawing. In the drawings, the sizes of elements may be enlarged for clarity of the present disclosure. It will be understood that, although the tell is first, second, etc. may be used herein to describe various elements, these elements should not be limited by these terms. These terms are only used to distinguish one element from another element. For example, a first element discussed below could be termed a second element, and similarly, a second element could be termed a first element. As used herein, the singular forms are intended to include the plural forms as well, unless the context clearly indicates otherwise.

It will be further understood that the terms "comprises", "includes," "including," or "comprising," when used in this specification, specify the presence of stated features, numerals, steps, operations, elements, parts, or a combination thereof, but do not preclude the presence or addition of one or more other features, numerals, steps, operations, elements, parts, or a combination thereof. It will also be understood that when a layer, a film, a region, a plate, etc. is referred to as being 'on' another part, it can be directly on the other part, or intervening layers may also be present. When a layer, a film, a region, a plate, etc. is referred to as being 'under' another part, it can be directly under the other part, or intervening layers may also be present. The term "or" is not an exclusive term, and may have the same meaning as the term "and/or."

In the present disclosure,

means a position to be connected or bonded.

In the present disclosure, "substituted or unsubstituted" may mean substituted with at least one substituent selected from a deuterium atom, a halogen atom, cyano, nitro, amino, silyl, boron, phosphine oxide, phosphine sulfide, alkyl, alkenyl, fluorenyl, aryl, and heteroaryl or unsubstituted. In addition, each of the substituent illustrated above may be substituted or unsubstituted. For example, a biphenyl may be interpreted as aryl, or a phenyl substituted with phenyl.

In the present disclosure, the term "forming a ring by combining adjacent groups with each other" or "combine to form a ring" may mean forming a substituted or unsubstituted hydrocarbon ring, or substituted or unsubstituted heterocycle by combining adjacent groups with each other. The hydrocarbon ring may include an aliphatic hydrocarbon ring and an aromatic hydrocarbon ring. The heterocycle may include an aliphatic heterocycle and aromatic heterocycle. The hydrocarbon ring and heterocycle may be a monocycle or polycycle. In addition, the ring formed by combining adjacent groups may be connected with another ring to form a Spiro structure.

In the present disclosure, the term "adjacent groups" may mean a substituent substituted with an atom directly connected with another atom substituted with a corresponding substituent, a different substituent substituted with an atom substituted with a corresponding substituent, or a substituent disposed stereoscopically at the nearest position to a corresponding substituent. For example, two methyl groups in 1,2-dimethylbenzene may be interpreted as "adjacent groups", and two ethyl groups in 1,1-diethylcyclopentene may be interpreted as "adjacent groups".

In the present disclosure, halogen may include a fluorine atom, a chlorine atom, a bromine atom, or an iodine atom.

In the present disclosure, the alkyl group may have a linear or branched chain or a cycle shape. The carbon number of the alkyl group may be 1 to 30, 1 to 20, 1 to 10, or 1 to 6. Examples of the alkyl group may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethyihexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldodecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyl eicosyl, 2-butyl eicosyl, 2-hexyl eicosyl, 2-octyl eicosyl, n-henicosyl, n-docosyl, n-tricosyl, n-tetracosyl, n-pentacosyl, n-hexacosyl, n-heptacosyl, n-octacosyl, n-nonacosyl, n-triacontyl, etc., without limitation.

In the present disclosure, the aryl group may be monocyclic aryl or polycyclic aryl. The carbon number of the aryl group for forming a ring may be 6 to 30, 6 to 20, or 6 to 15.

Examples of the aryl group may include phenyl, naphthyl, anthracenyl, phenanthryl, biphenyl, terphenyl, quaterphenyl, quinqphenyl, sexiphenyl, triphenylene, pyrenyl, benzofluoranthenyl, chrysenyl, fluorenyl, etc., without limitation.

In the present disclosure, the fluorenyl group may be substituted, or two substituents may be combined to form a Spiro structure.

In the present disclosure, the heteroaryl group may be heteroaryl group including at least one of O, N, or S as a heteroatom. The carbon number of the heteroaryl group for forming a ring may be 2 to 30, or 2 to 20. Examples of the heteroaryl group may include thiophene, furan, pyrrole, imidazole, thiazole, oxazole, oxadiazole, triazole, pyridyl, bipyridyl, pyrimidyl, triazine, triazole, acridyl, pyridazine, pyrazinyl, quinolinyl, quinazoline, quinoxalinyl, phenoxazyl, phthalazinyl, pyrido pyrimidinyl, pyrido pyrazinyl, pyrazino pyrazinyl, isoquinoline, indole, carbazole, N-arylcarbazole, N-heteroaryl carbazole, N-alkyl carbazole, benzoxazole, benzoimidazole, benzothiazole, benzocarbazole, benzothiophene, dibenzothiophene, thienothiophene, benzofuranyl, phenanthroline, thiazolyl, isooxazolyl, oxadiazolyl, thiadiazolyl, benzothiazolyl, phenothiazinyl, dibenzofuranyl, etc., without limitation.

In the present disclosure, the explanation of the aryl group may be applied to the arylene group, except that the arylene is divalent.

In the present disclosure, the silyl group may include alkyl silyl group and aryl silyl group. Examples of the silyl group may include trimethylsilyl, triethylsilyl, t-butyl dimethylsilyl, vinyl dimethylsilyl, propyl dimethylsilyl, triphenylsilyl, diphenylsilyl, phenylsilyl, etc., without limitation.

In the present disclosure, the boron group may include alkyl boron group and aryl boron group. Examples of the boron group may include trimethyl boron, triethyl boron, t-butyl dimethyl boron, triphenyl boron, diphenyl boron, phenyl boron, etc., without limitation.

In the present disclosure, the alkenyl group may be linear or branched. The carbon number may be, e.g., 2 to 30, 2 to 20, or 2 to 10. Examples of the alkenyl may include vinyl, 1-butenyl, 1-pentenyl, 1,3-butadienyl aryl, styrenyl, styrylvinyl, etc., without limitation.

In the present disclosure, the carbon number of the amine group may be, e.g., 1 to 30. The amine may include an alkyl amine group and aryl amine group. Examples of the amine group may include methylamine, dimethylamine, phenylamine, naphthylamine, 9-methyl-anthracenylamine, triphenylamine, etc., without limitation.

Hereinafter, the nitrogen-containing compound according to an embodiment will be explained.

The nitrogen-containing compound according to an embodiment may represented by the following Formula 1.

[Formula 1]

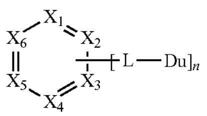

In Formula 1, $X_1$ to $X_6$ may each independently be, e.g., $CR_1$ or N. In an implementation, one or two among $X_1$ to $X_6$ may be N. Each $R_1$ may independently be or include, e.g., a bond to L, a hydrogen atom, a deuterium atom, a halogen atom, a substituted or unsubstituted alkyl group having 1 to 30 carbon atoms, a substituted or unsubstituted aryl group having 6 to 30 ring carbon atoms, or a substituted or unsubstituted heteroaryl group of 2 to 30 ring carbon atoms. In an implementation, $R_1$ may be a substituted or unsubstituted fluorenyl group. L may be or may include, e.g., a substituted or unsubstituted arylene group having 6 to 30 ring carbon atoms. n may be, e.g., 1 or 2. Du may be, e.g., a group represented by the following Formula 2.

[Formula 2]

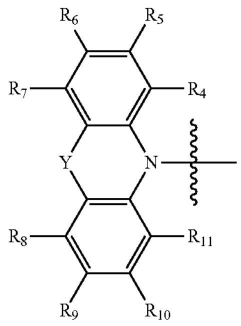

In Formula 2, Y may be, e.g., a direct linkage, O, S, $CR_2R_3$, Si, Ge, or P. $R_2$ to $R_{11}$ may each independently be or include, e.g., a hydrogen atom, a deuterium atom, halogen atom, a substituted or unsubstituted alkyl group having 1 to 30 carbon atoms, a substituted or unsubstituted aryl group having 6 to 30 ring carbon atoms, or a substituted or unsubstituted heteroaryl group having 2 to 30 ring carbon atoms. In an implementation, at least one of $R_2$ to $R_{11}$ may be a substituted or unsubstituted fluorenyl group. In an implementation, adjacent ones of $R_2$ to $R_{11}$ may be separate or may be combined with an adjacent group to form a ring.

represents a bonding site with L of Formula 1.

The direct linkage may be, e.g., a single bond.

The nitrogen-containing compound according to an embodiment may include an electron acceptor, a linker, and an electron donor. For example, the hexagonal ring moiety including $X_1$ to $X_6$ in Formula 1 may be the electron acceptor, L may be the linker, and Du (represented by Formula 2) may be the electron donor.

In an implementation, the hexagonal ring moiety including $X_1$ to $X_6$ in Formula 1 may include one or two N, e.g., one or two of $X_1$ to $X_6$ may be N.

In an implementation, the hexagonal ring moiety including $X_1$ to $X_6$ in Formula 1 may include two N, e.g., two of $X_1$ to $X_6$ may be N. In an implementation, the nitrogen-containing compound may be represented by one of the following Formulae 3 to 5.

[Formula 3]

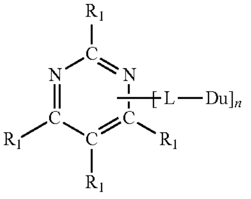

-continued

[Formula 4]

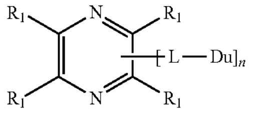

[Formula 5]

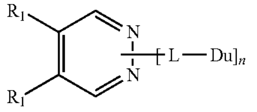

In Formulae 3 to 5, L, Du, $R_1$, and n may be the same as described above.

$X_1$ to $X_6$ (other than N) may be represented by $CR_1$, and a plurality of $R_1$ may be the same or different. For example, in the case where the hexagonal ring moiety including $X_1$ to $X_6$ is substituted with at least two substituents, the substituents may be the same or different.

In an implementation, in the case where $R_1$ is plural, at least one may be hydrogen atom.

In an implementation, $R_1$ may be or may include, e.g., a substituted or unsubstituted alkyl group having 1 to 30 carbon atoms. In an implementation, $R_1$ may be or may include, e.g., a substituted or unsubstituted alkyl group having 1 to 10 carbon atoms. In an implementation, $R_1$ may be methyl or ethyl. In an implementation, $R_1$ may be methyl.

In an implementation, $R_1$ may be or may include, e.g., a substituted or unsubstituted aryl group having 6 to 30 ring carbon atoms. In an implementation, $R_1$ may be or may include, e.g., a substituted or unsubstituted aryl group of 6 to 20 ring carbon atoms. In an implementation, $R_1$ may be phenyl or naphthyl. In an implementation, $R_1$ may be phenyl. In an implementation, $R_1$ may be naphthyl. In an implementation, $R_1$ may be fluorenyl.

In an implementation, a plurality of adjacent $R_1$ may combine but not form a ring. For example, the hexagonal ring moiety including $X_1$ to $X_6$ may be a monocycle.

In an implementation, L may be, e.g., a substituted or unsubstituted phenylene group. In an implementation, L may be, e.g., 1,3-phenylene or 1,4-phenylene. In an implementation, L may be, e.g., 1,4-phenylene.

In an implementation, the compound represented by Formula 1 may be represented by the following Formula 6.

[Formula 6]

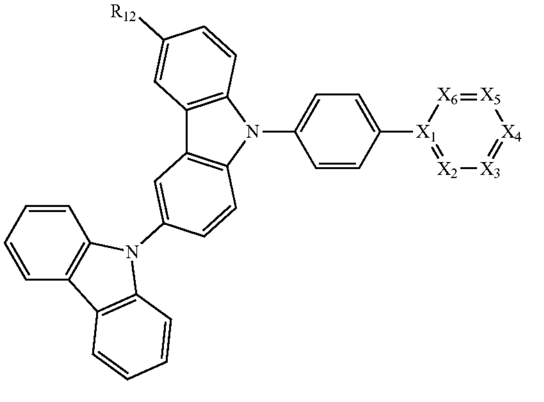

In Formula 6, $R_{12}$ may be or may include, e.g., a hydrogen atom or a substituted or unsubstituted carbazole group. $X_1$ to $X_6$ may be the same as defined in the above. The compound represented by Formula 6 may be provided with a low electron accepting property and a low electron donating property, in the case where the compound is used in a TADF organic electroluminescence device, deep blue may be attained. Y may be a direct linkage, or $CR_2R_3$. In the case where Y is the direct linkage, Du represented by Formula 2 may be, e.g., a substituted or unsubstituted carbazole group. In the case where Y is $CR_2R_3$, $R_2$ and $R_3$ may each independently be, e.g., a substituted or unsubstituted alkyl group having 2 to 30 carbon atoms, or a substituted unsubstituted aryl group having 6 to 30 ring carbon atoms. In an implementation, $R_2$ and $R_3$ may each independently be, e.g., methyl or phenyl. In an implementation, $R_2$ and $R_3$ may combine with each other to form a ring. In an implementation, $R_2$ and $R_3$ may combine to form a fluorene ring. In an implementation, the group represented by Formula 2 may be represented by one of the following Formulae 7 to 16.

[Formula 7]

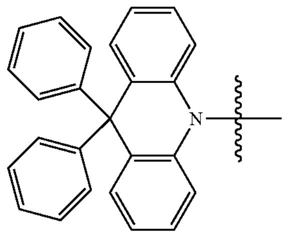

[Formula 8]

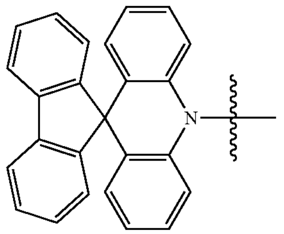

[Formula 9]

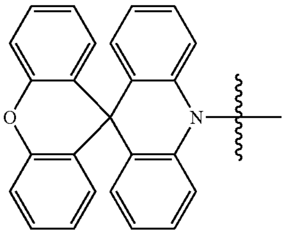

[Formula 10]

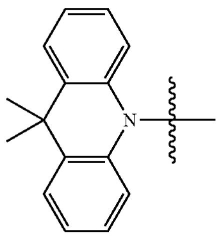

-continued

[Formula 11]

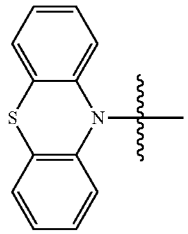

[Formula 12]

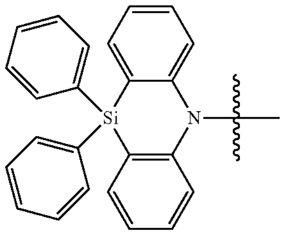

[Formula 13]

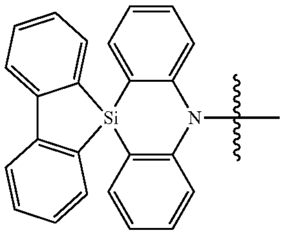

[Formula 14]

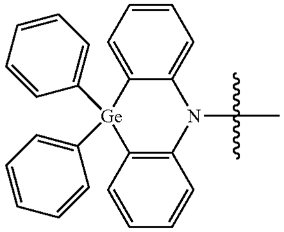

-continued

[Formula 15]

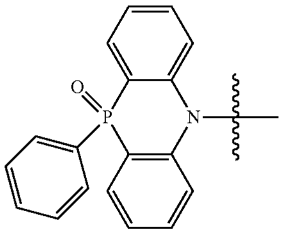

[Formula 16]

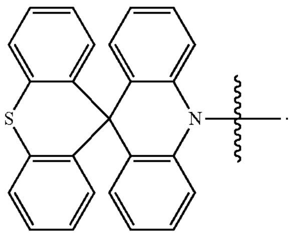

Each of Formulae 9 to 16 may be additionally substituted, and the substituent may be the substituent described in the above definition of “substituted or unsubstituted”. For example, each of Formulae 9 to 16 may be substituted with alkyl or unsubstituted.

In Formula 2, $R_4$ to $R_{11}$ may each independently be or include, e.g., a substituted or unsubstituted heteroaryl group having 2 to 30 ring carbon atoms, a substituent including fluorine atom, or a substituent including silicon atom. The substituent including the fluorine atom may be, e.g., alkyl group substituted with at least one fluorine atom, or aryl group substituted with at least one fluorine atom, which has 6 to 30 ring carbon atoms. The substituent including the fluorine group may be, e.g., $CF_3$. The substituent including the silicon atom may be, e.g., trimethylsilyl.

In an implementation, n may be 2. In the case where n is 2, the compound represented by Formula 1 may include two electron donors represented by Du, and an organic electroluminescence device including the same may easily attain high efficiency.

In the case where n is 2, two L may be the same or different, and two Du may be the same or different.

In an implementation, the nitrogen-containing compound represented by Formula 1 may be one of the following Compounds 1 to 95.

1

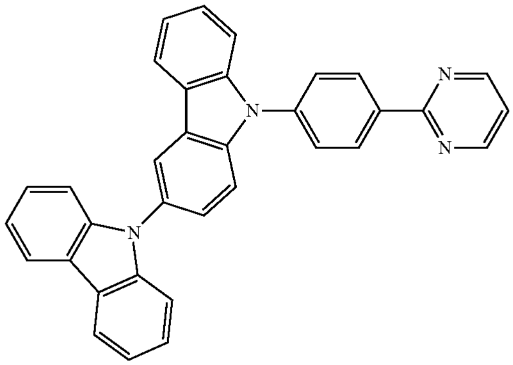

2

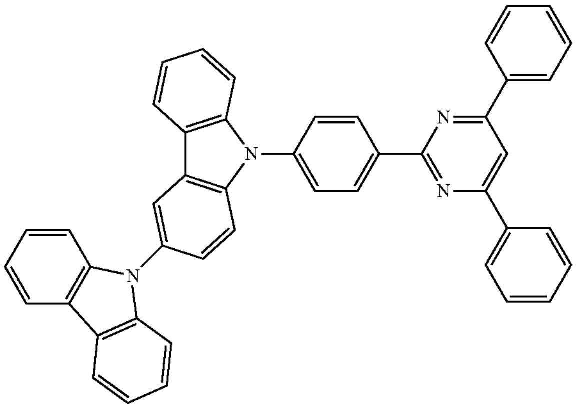

-continued
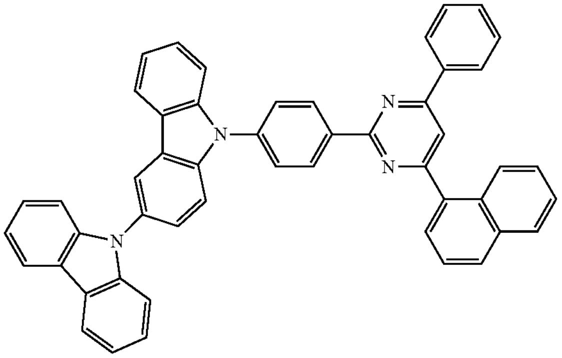
3
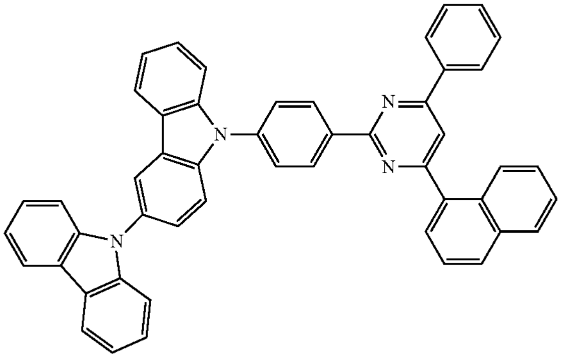
4
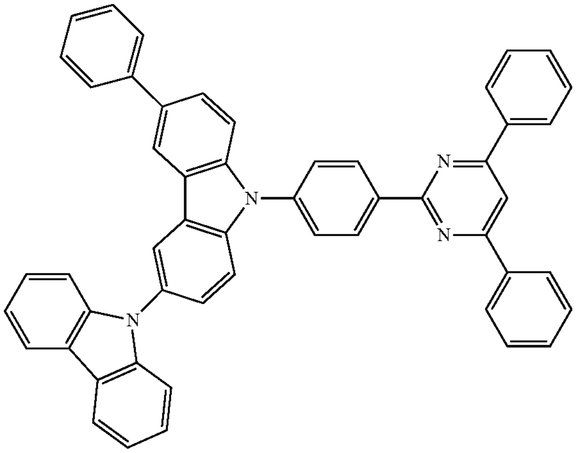
5
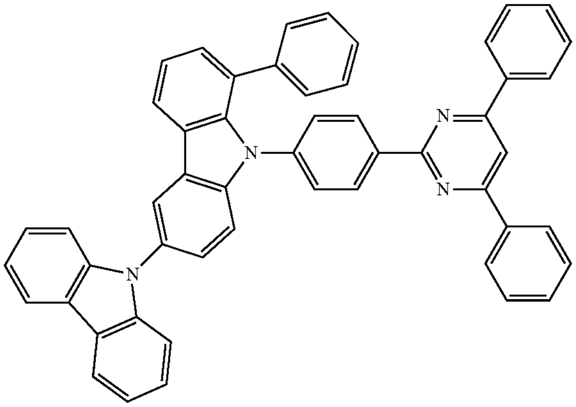
6
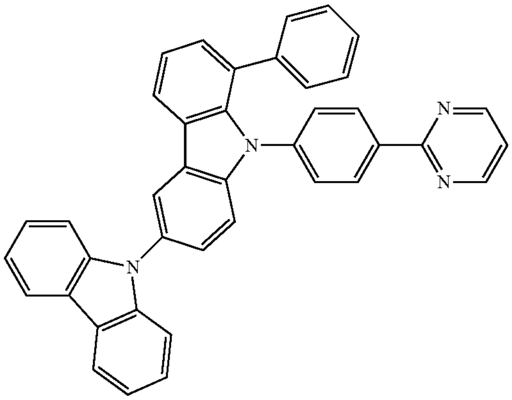
7
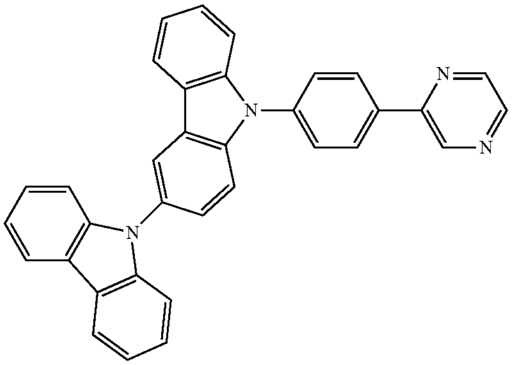
8
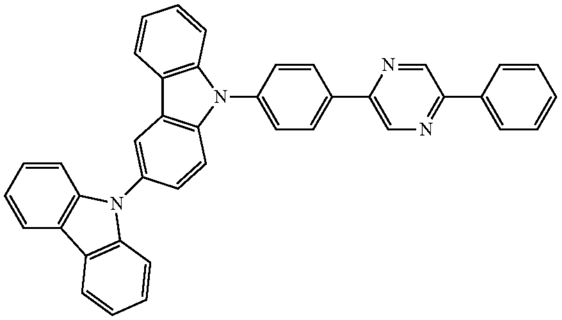
9
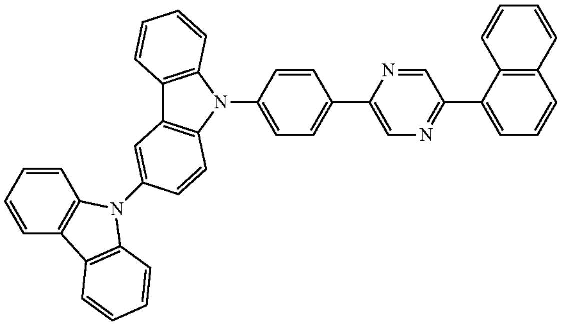
10

-continued
11
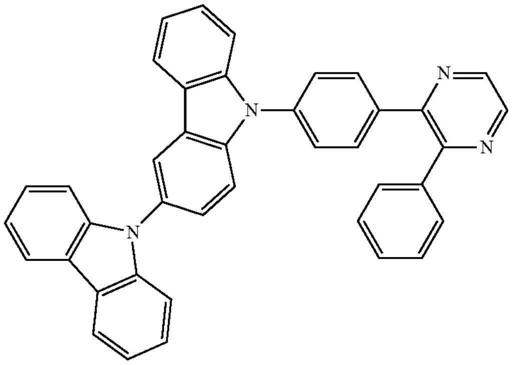
12
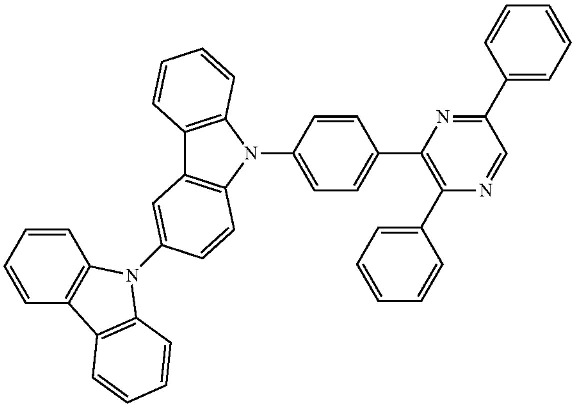
13
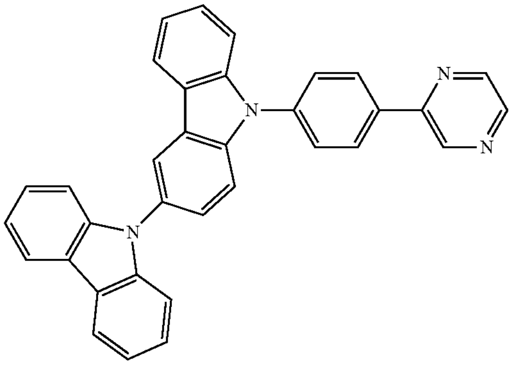
14
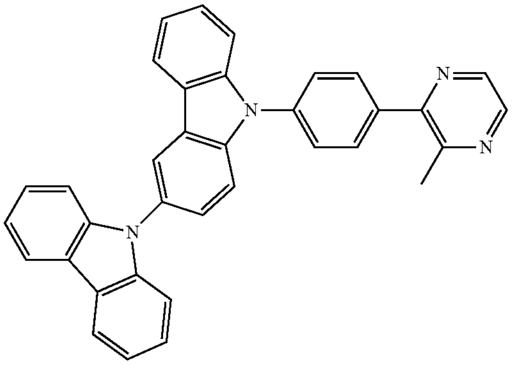
15
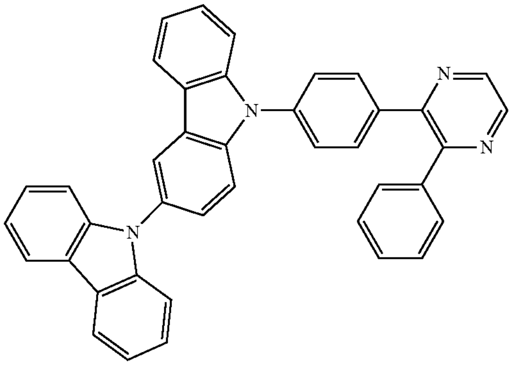
16
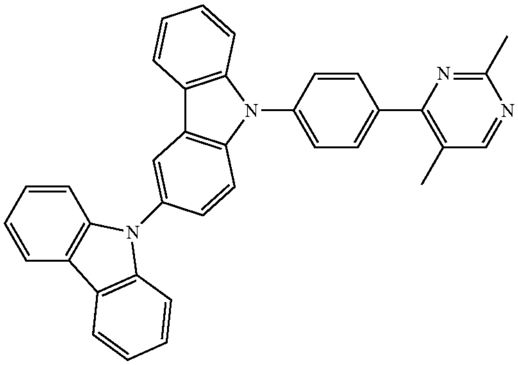
17
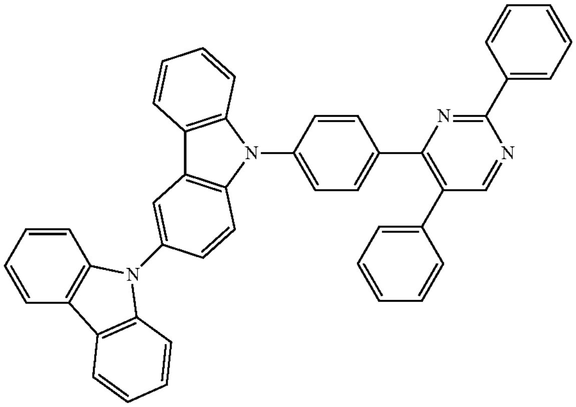
18
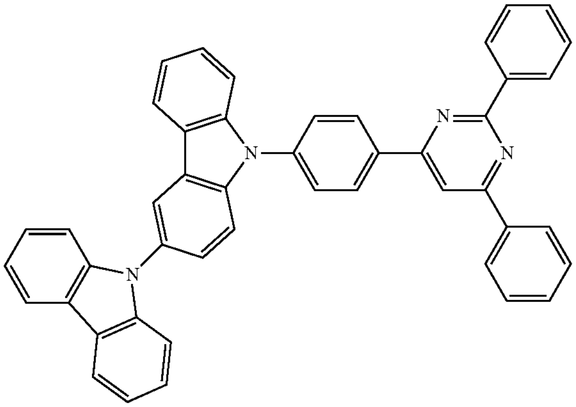

-continued
19
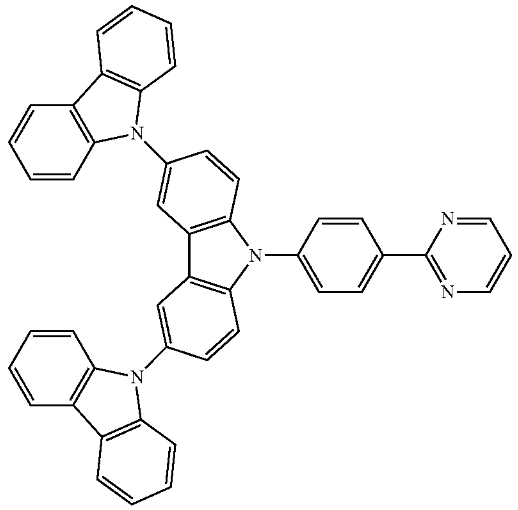
20
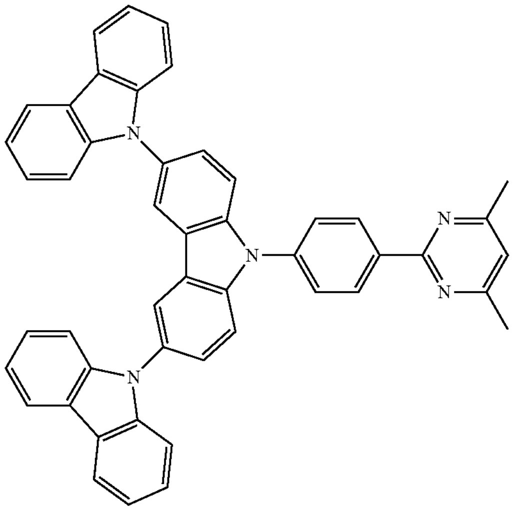
21
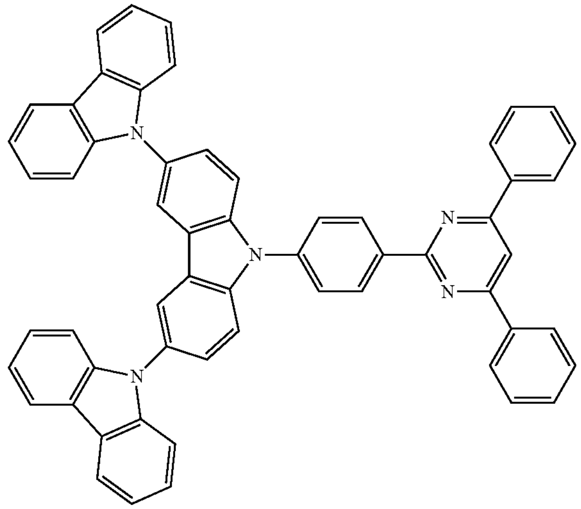
22
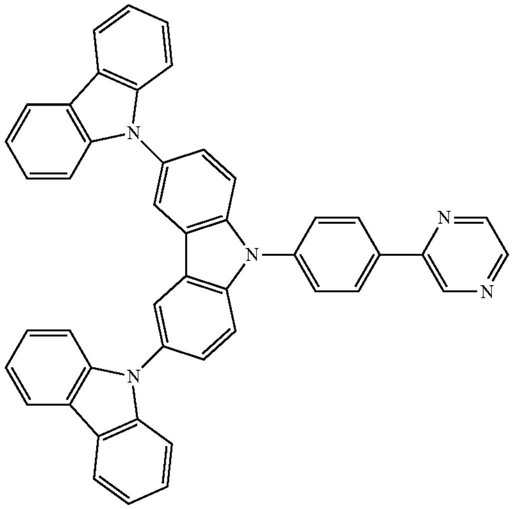
23
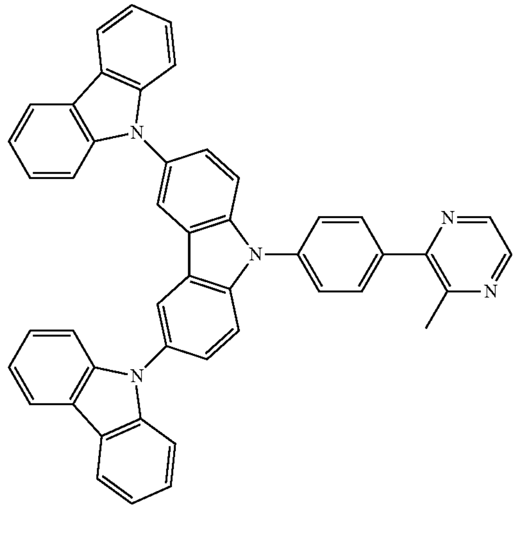
24
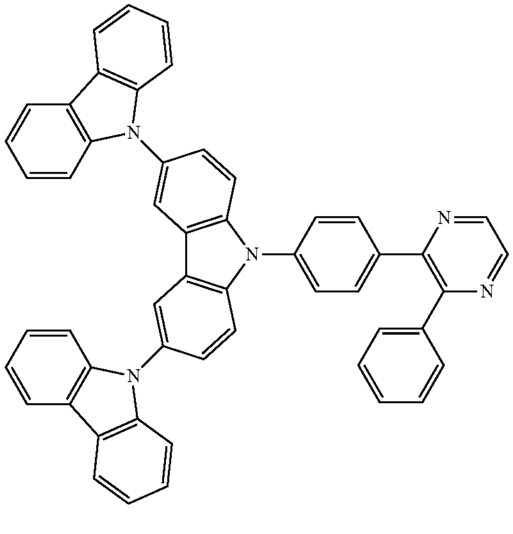

-continued
25
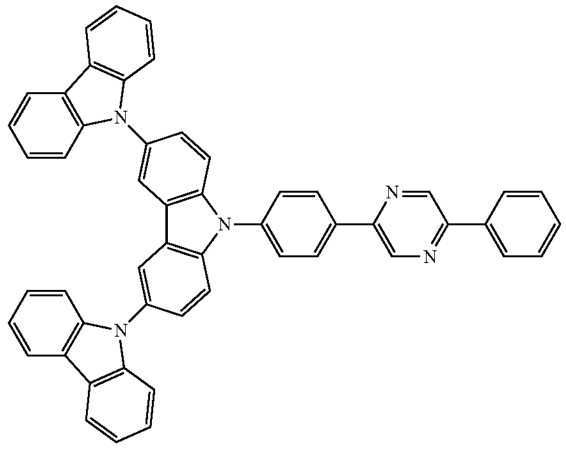
26
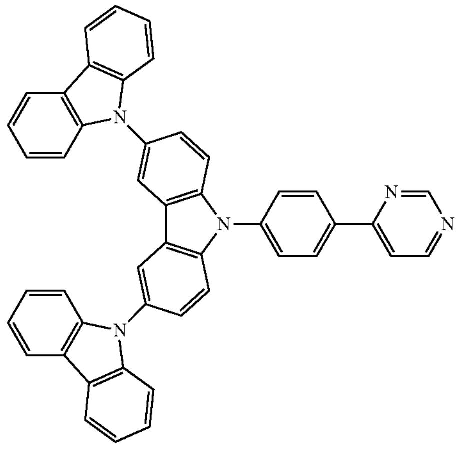
27
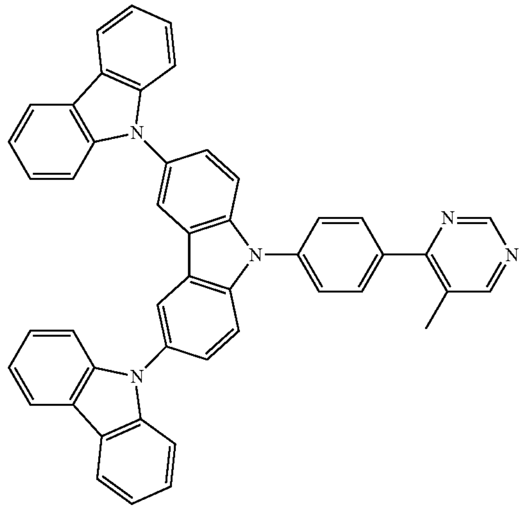
28
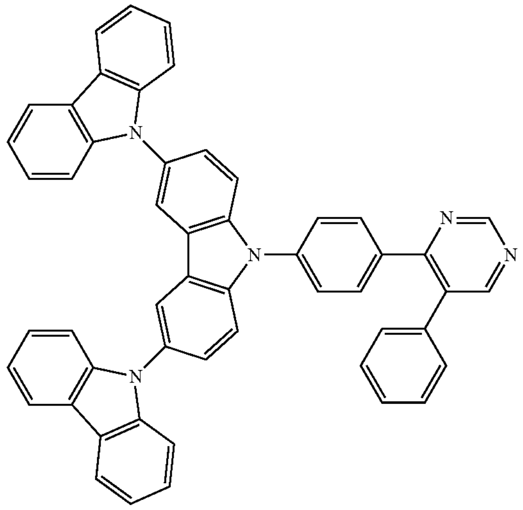
29
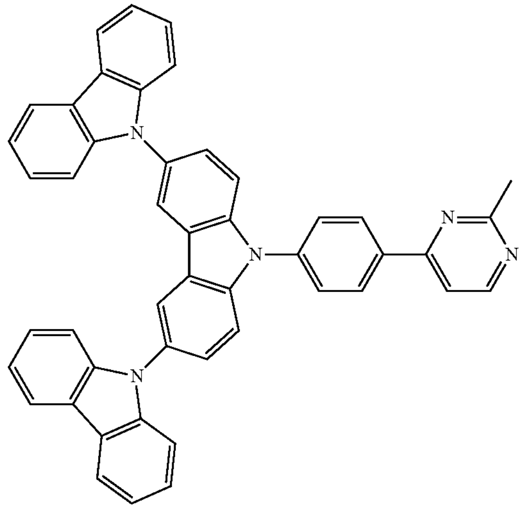
30
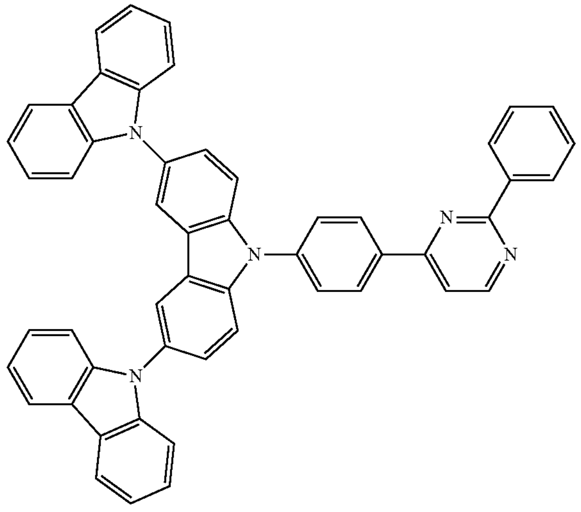

-continued
31
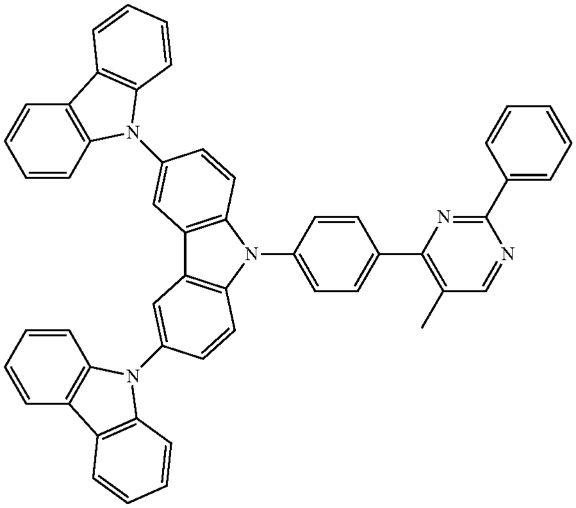
32
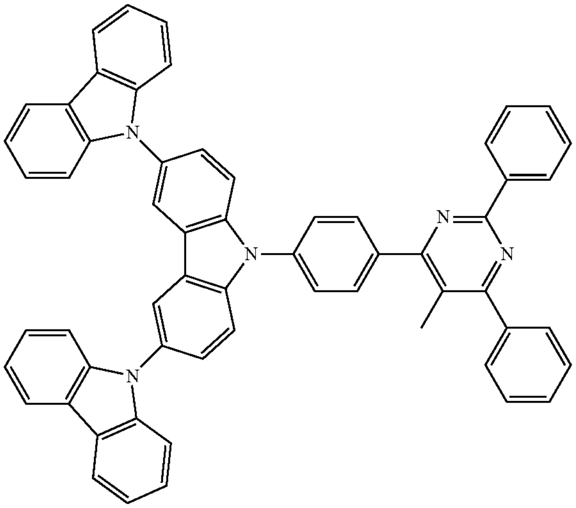
33
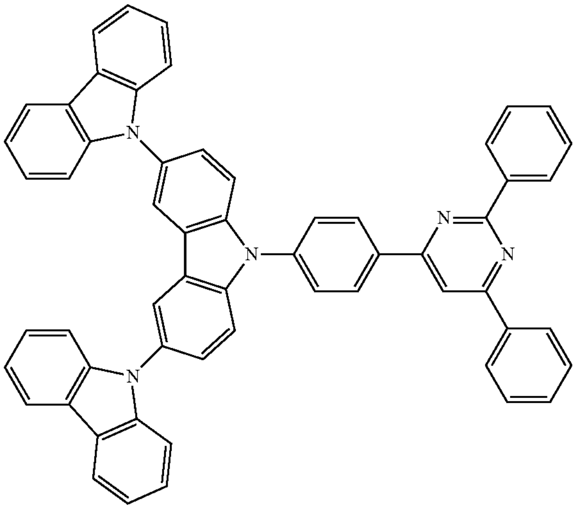
34
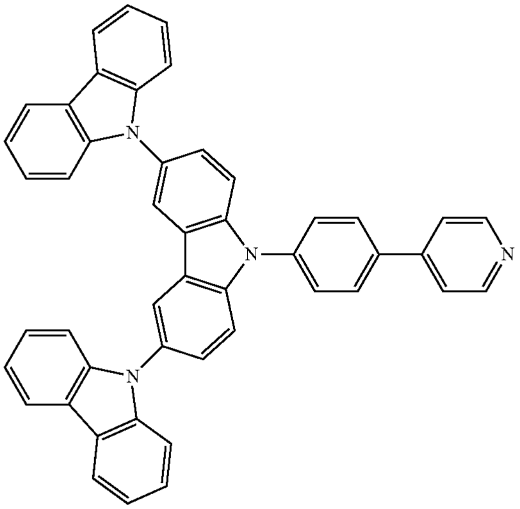
35
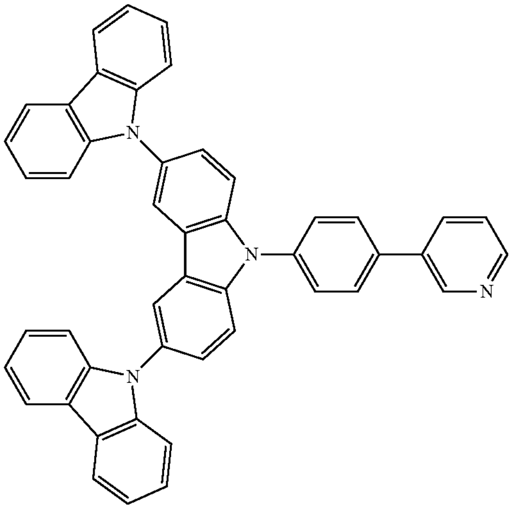
36
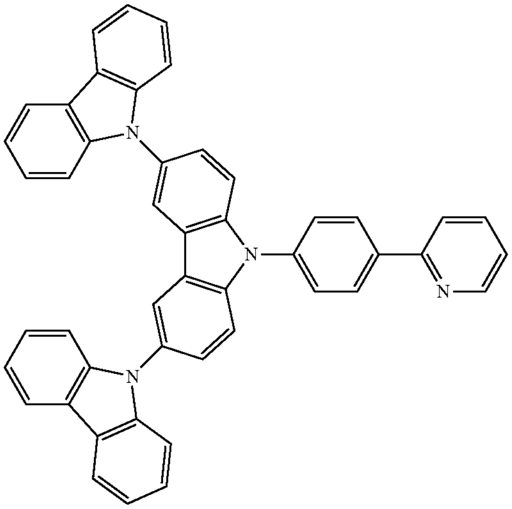

-continued
37
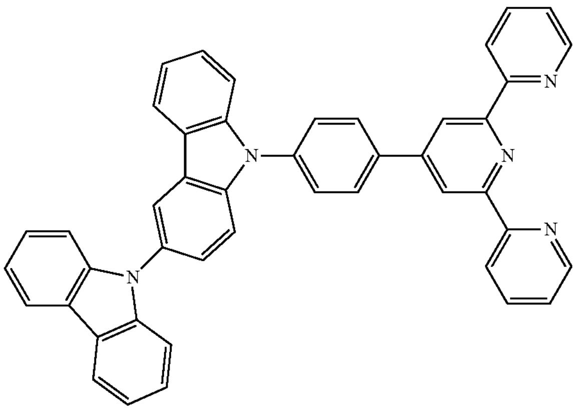
38
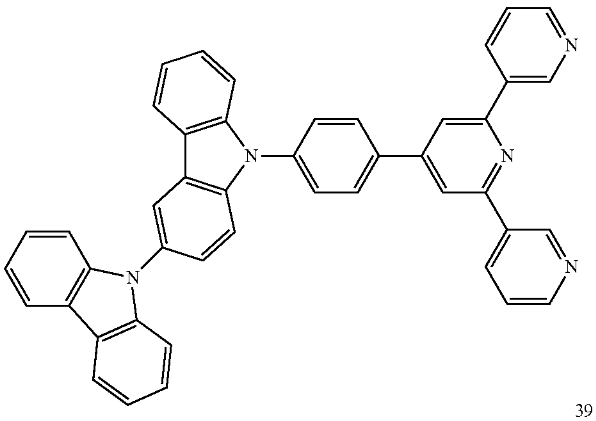
39
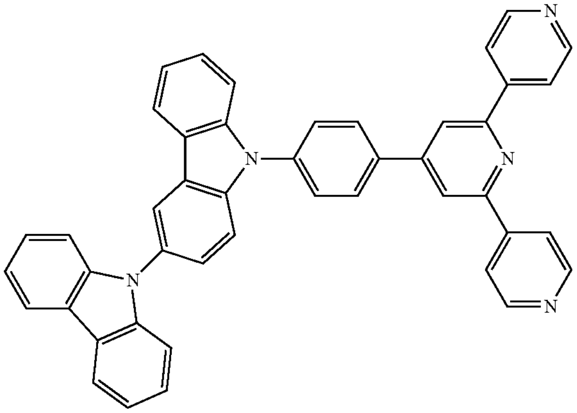
40
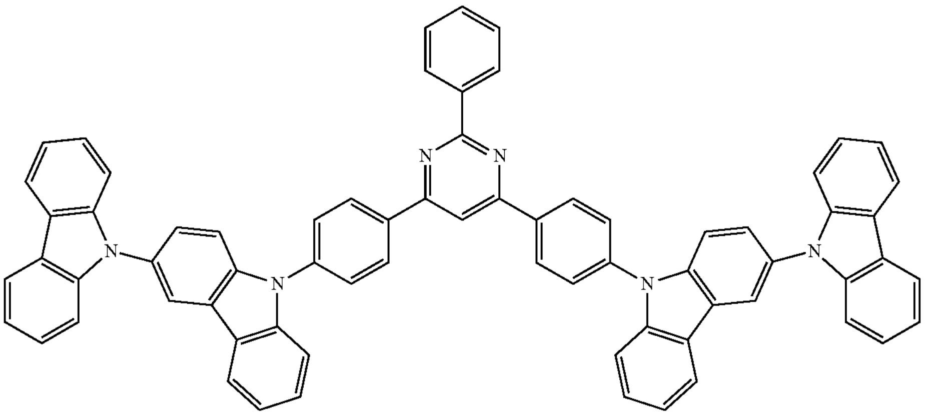
41
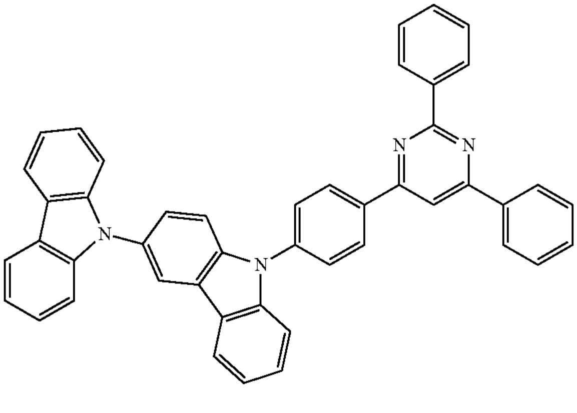
42
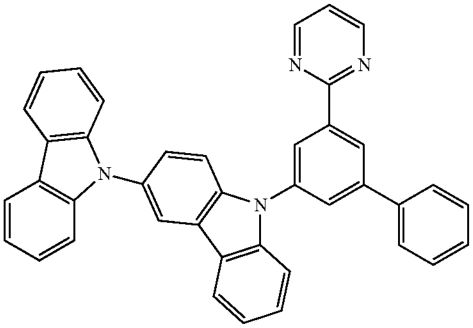

-continued
43
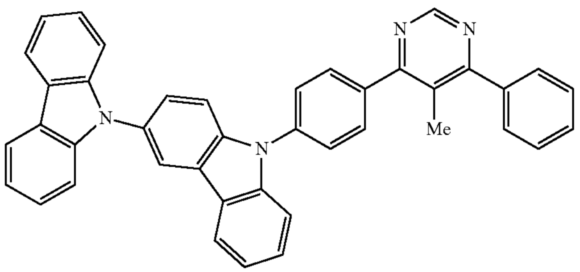
44
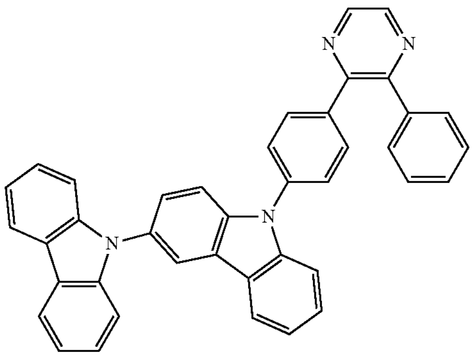
45
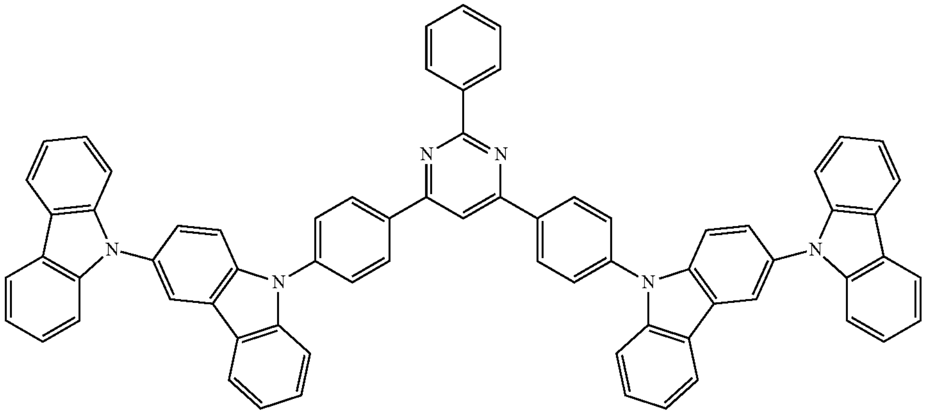
46
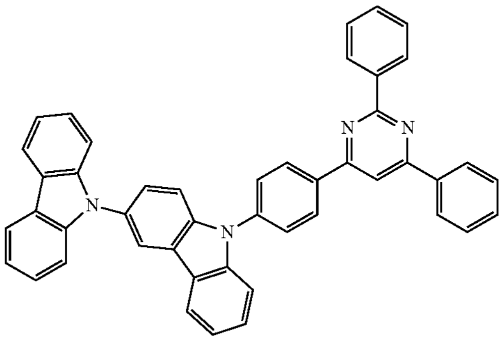
47
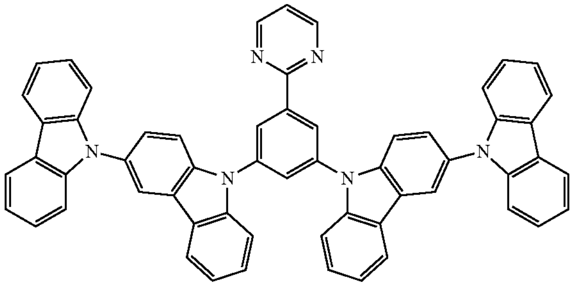
48
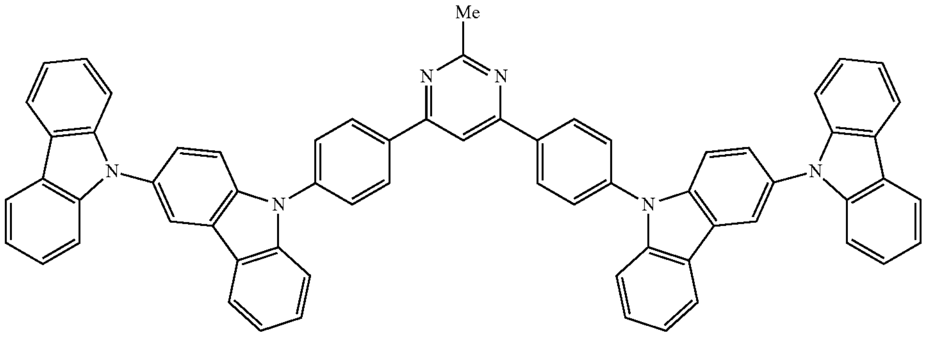

-continued
49
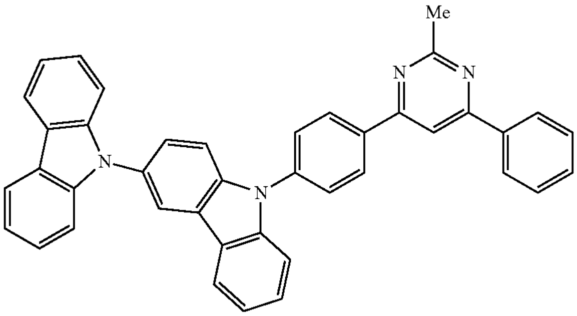
50
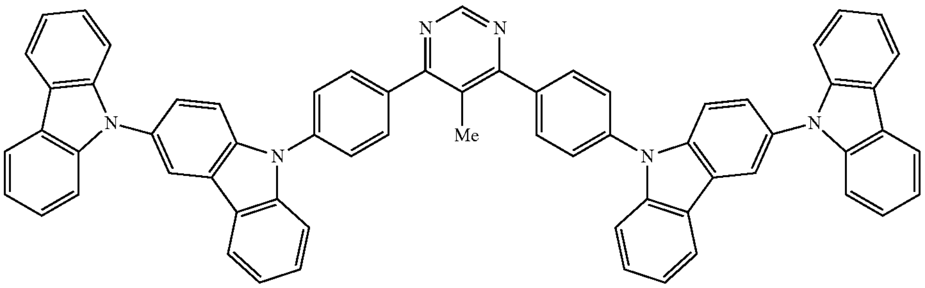
51
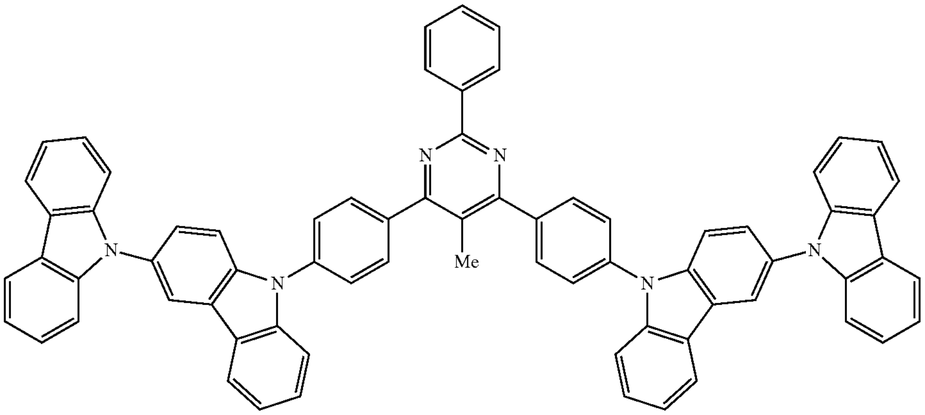
52
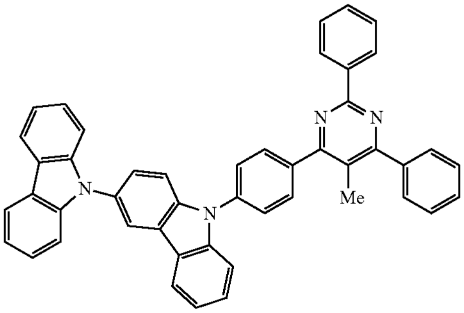
53
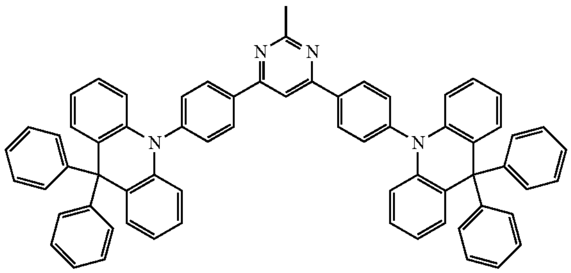

-continued
54
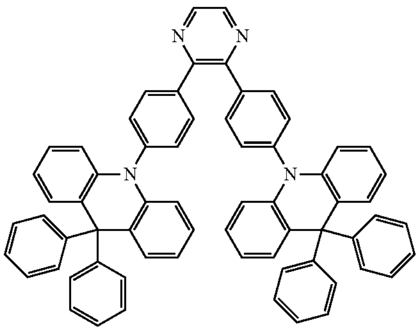
55
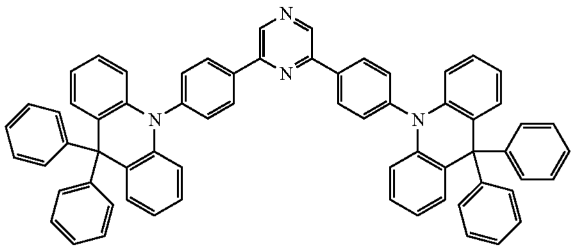
56
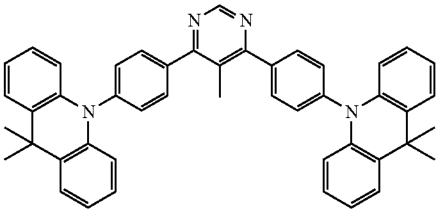
57
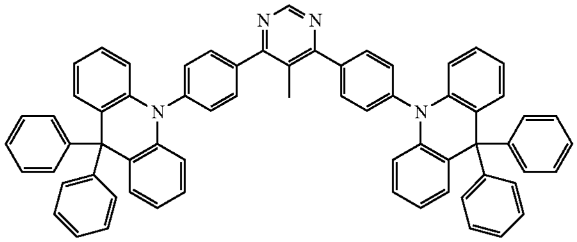
58
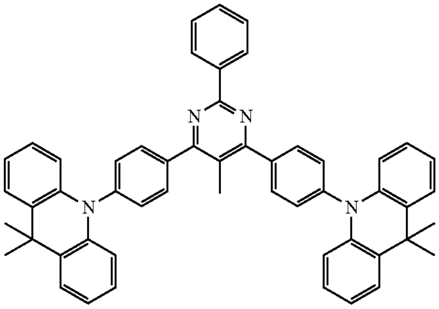
59
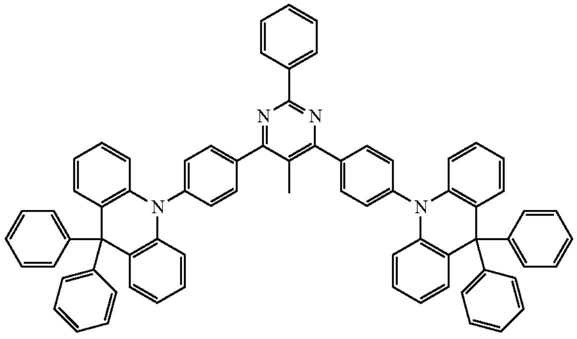
60
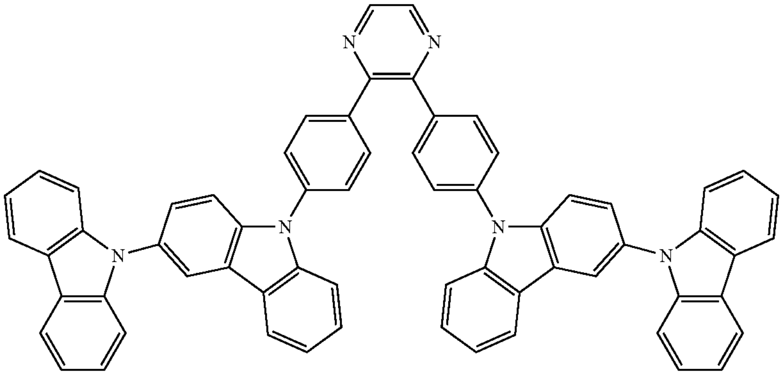

-continued
61
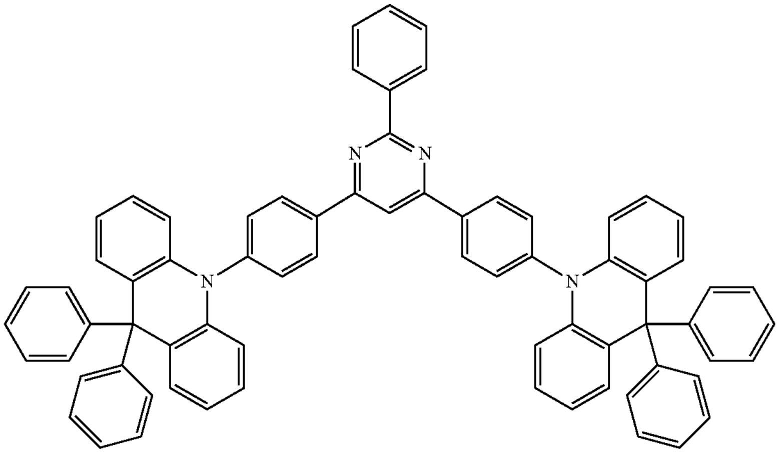
62
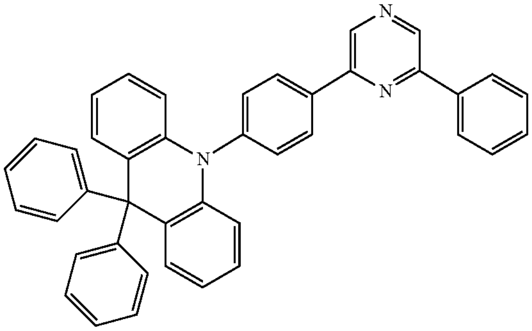
63
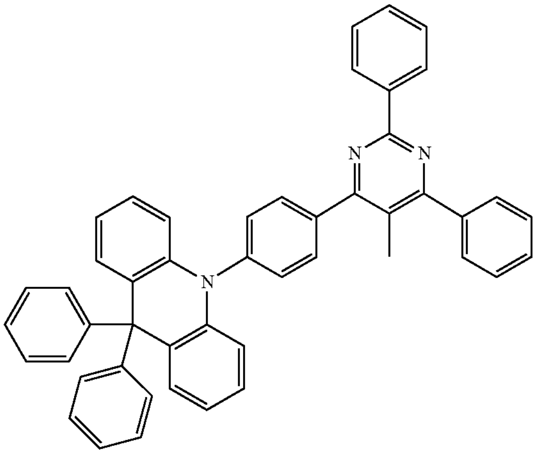
64
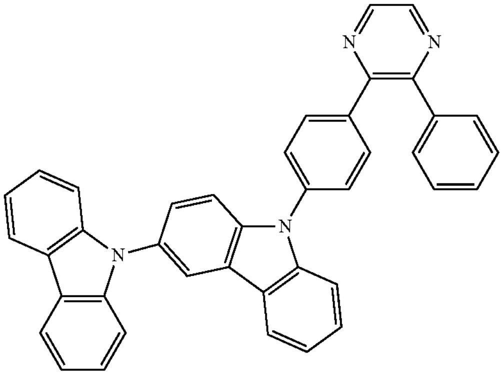
65
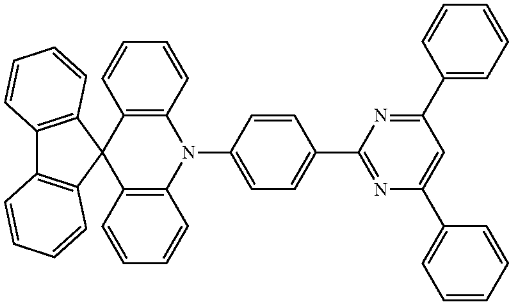
66
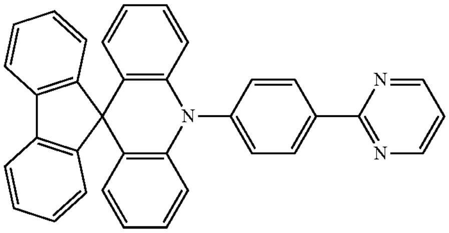
67
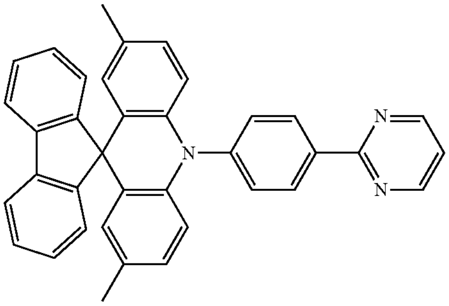

-continued
68
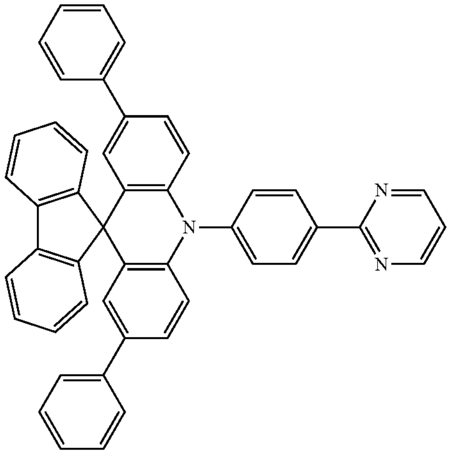
69
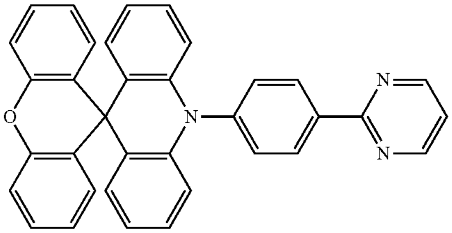
70
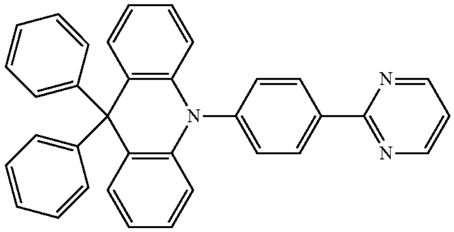
71
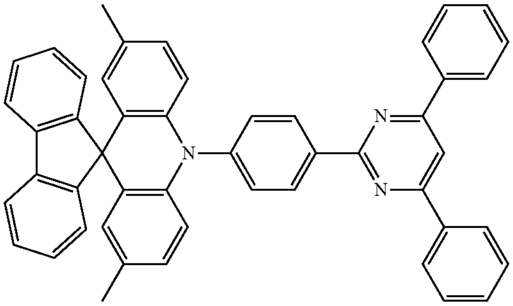
72
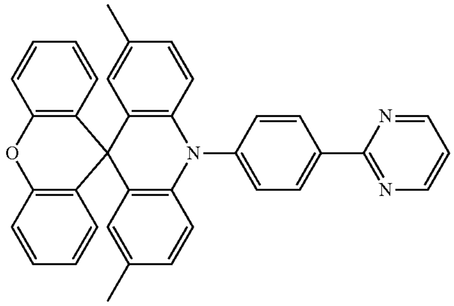
73
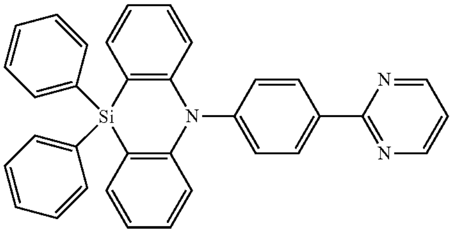
74
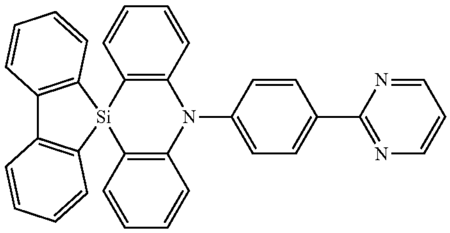
75
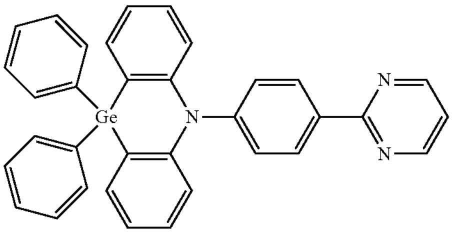
76
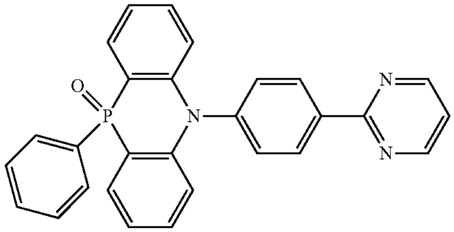

-continued
77
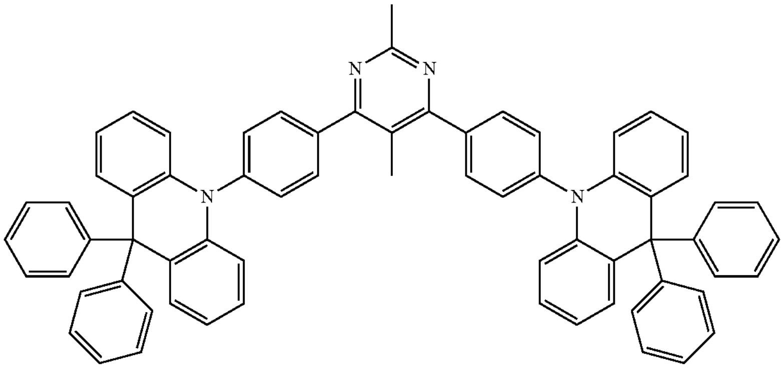
78
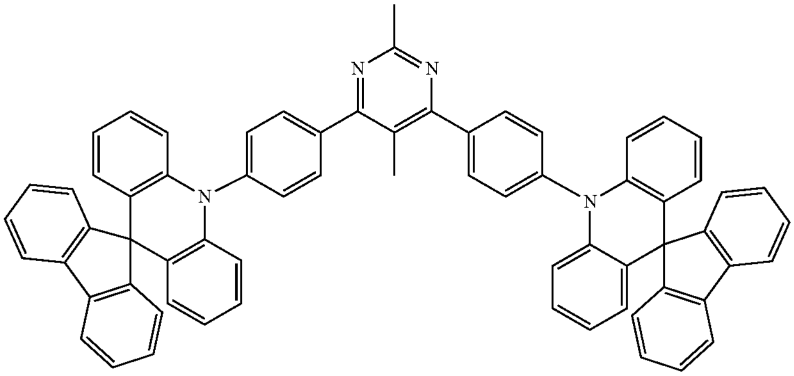
79
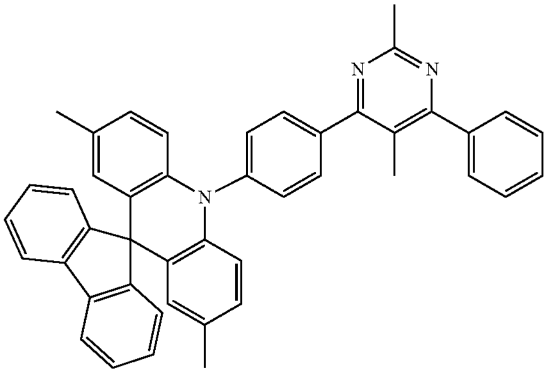
80
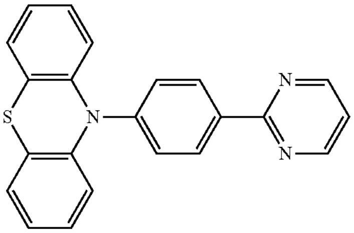
81
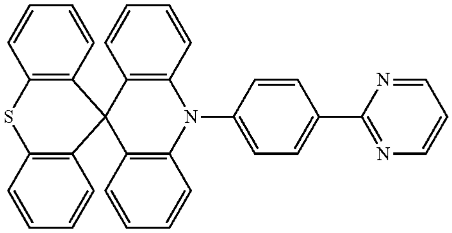
82
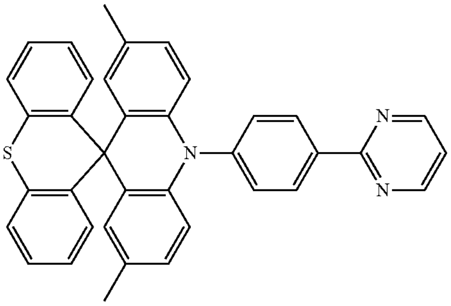

-continued
83
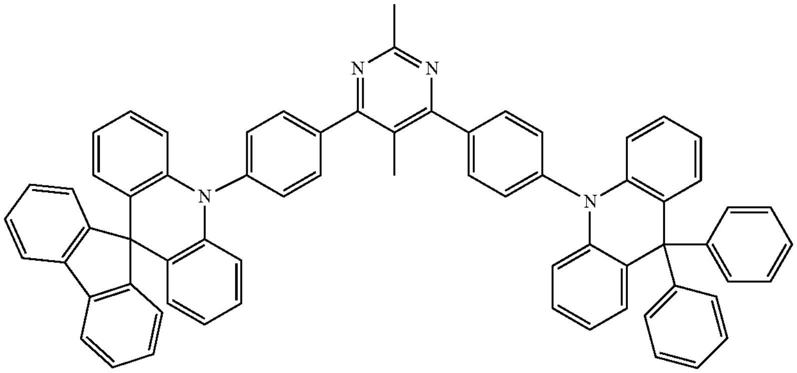
84
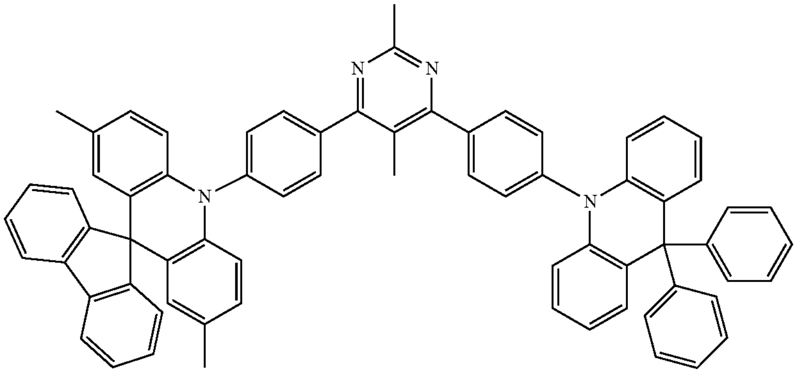
85
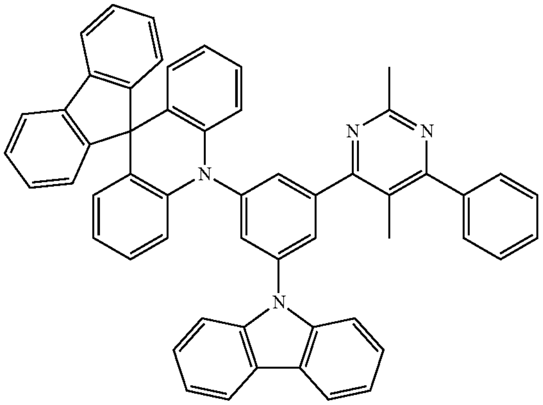
86
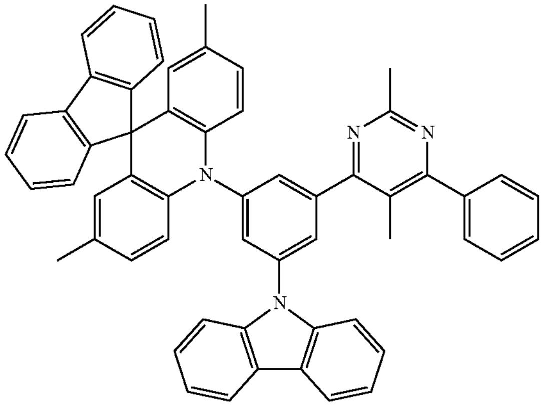
87
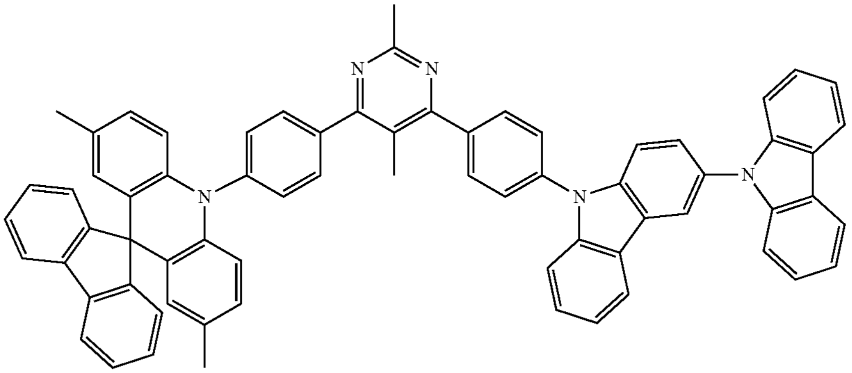

-continued
88
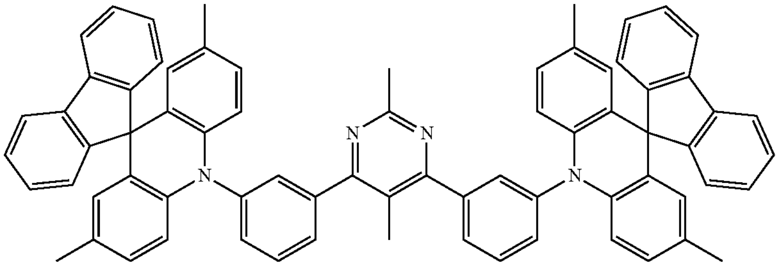
89
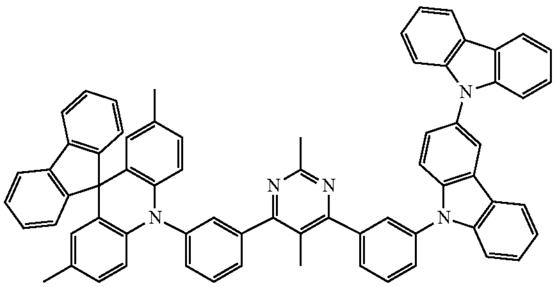
90
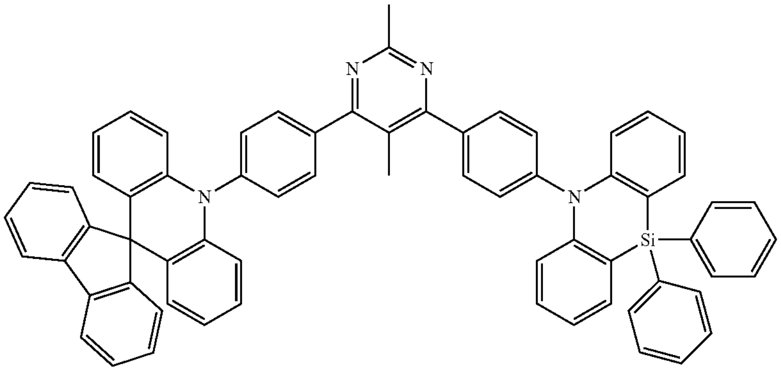
91
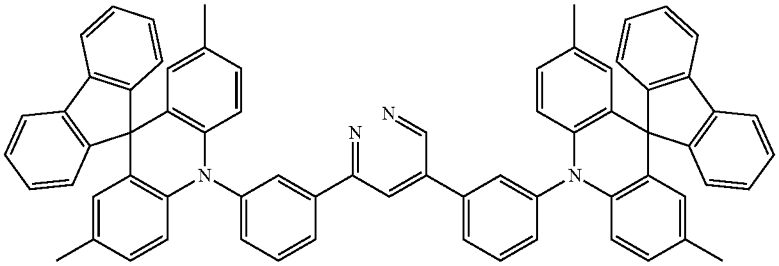
92
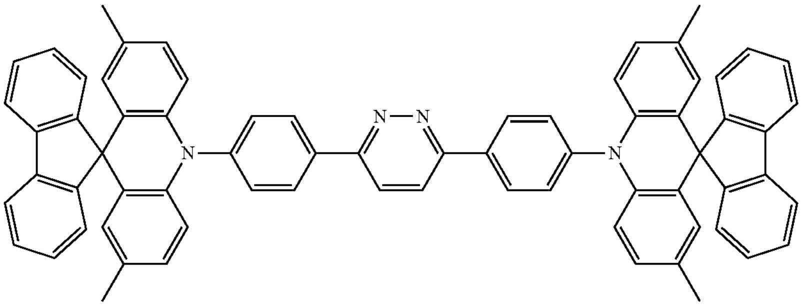

-continued

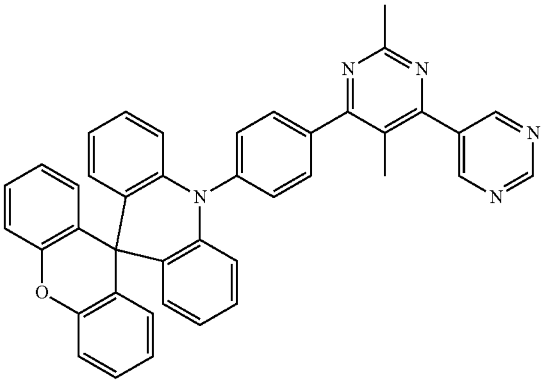

93

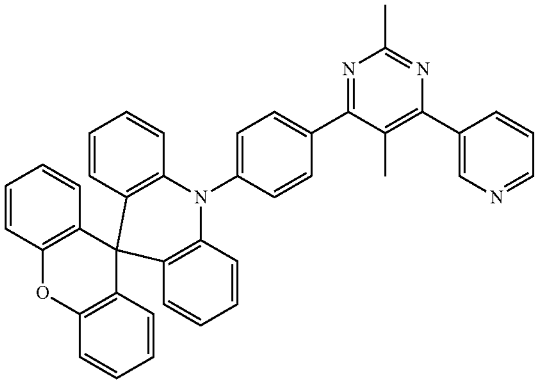

94

95

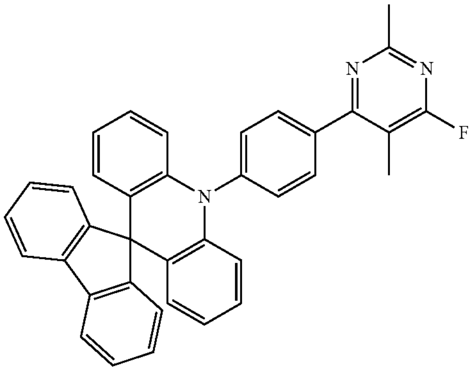

Hereinafter, an organic electroluminescence device according to an embodiment will be explained. The explanation will be mainly with the difference in the nitrogen-containing compound according to an embodiment, and unexplained part will follow the above-description on the nitrogen-containing compound according to an embodiment.

Figure 2:
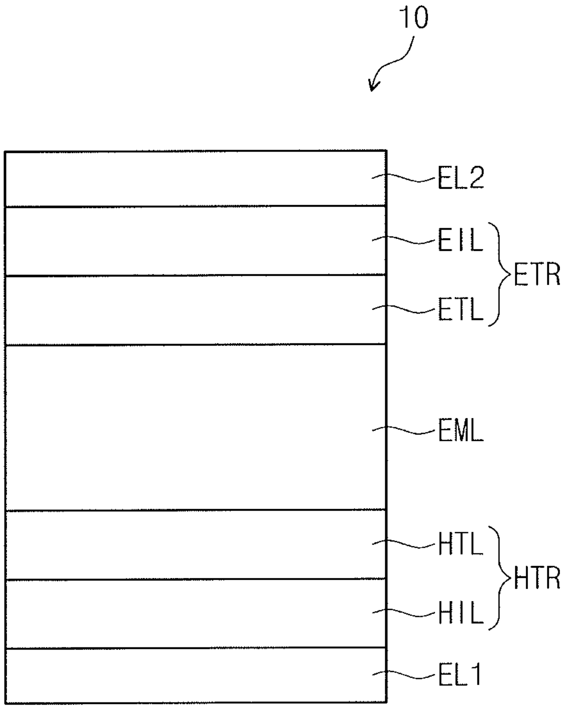
FIG. 2 illustrates a cross-sectional view schematically showing an organic electroluminescence device according to an embodiment.

FIG. 1 illustrates a cross-sectional view schematically showing an organic electroluminescence device according to an embodiment. FIG. 2 illustrates a cross-sectional view schematically showing an organic electroluminescence device according to an embodiment.

Referring to FIGS. 1 and 2, an organic electroluminescence device 10 according to an embodiment may include a first electrode EL1, a hole transport region HTR, an emission layer EML, an electron transport region ETR, and a second electrode EL2.

The first electrode EL1 has conductivity. The first electrode EL1 may be a pixel electrode or an anode. The first electrode EL1 may be a transmissive electrode, a transflective electrode, or a reflective electrode. When the first electrode EL1 is the transmissive electrode, the first electrode EL1 may be formed using a transparent metal oxide such as indium tin oxide (ITO), indium zinc oxide (IZO), zinc oxide (ZnO), or indium tin zinc oxide (ITZO). In the case where the first electrode EL1 is the transflective electrode or reflective electrode, the first electrode EL1 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). Also, the first electrode EL1 may include a plurality of layers including the reflective layer or transflective layer formed using the above materials, or a transparent layer formed using ITO, IZO, ZnO, or ITZO.

The hole transport region HTR may be provided on the first electrode EL1. The hole transport region HTR may include at least one of a hole injection layer HIL, a hole transport layer HTL, a hole buffer layer, or an electron blocking layer. The thickness of the hole transport region HTR may be, e.g., from about 200 Å to about 3,000 Å.

The hole transport region HTR may have a single layer formed using a single material, a single layer formed using a plurality of different materials, or a multilayer structure including a plurality of layers formed using a plurality of different materials.

For example, the hole transport region HTR may have the structure of a single layer such as a hole injection layer HIL and a hole transport layer HTL, or may have a structure of a single layer formed using a hole injection material and a hole transport material. In addition, the hole transport region HTR may have a structure of a single layer formed using a plurality of different materials, or a structure laminated from the first electrode EU of hole injection layer HIL/hole transport layer HTL, hole injection layer HIL/hole transport layer HTL/buffer layer, hole injection layer HIL/hole buffer layer, hole transport layer HTL/hole buffer layer, or hole injection layer HIL/hole transport layer HTL/electron blocking layer, without limitation.

The hole transport region HTR may be formed using various methods such as a vacuum deposition method, a spin coating method, a cast method, a Langmuir-Blodgett (LB) method, an inkjet printing method, a laser printing method, and a laser induced thermal imaging (LITI) method.

The hole injection layer HIL may include, e.g., dipyrazino [2,3-f:2',3'-h]quinoxaline-2,3,6,7,10,11-hexacarbonitrile (HAT-CN), a phthalocyanine compound such as copper phthalocyanine; N,N'-diphenyl-N,N'-bis-[4-(phenyl-m- tolyl-amino)-phenyl]-biphenyl-4,4'-diamine (DNTPD), 4,4',4"-tris(3-methylphenylphenylamino)triphenylamine (m-MTDATA), 4,4',4"-tris(N,N-diphenylamino)triphenylamine (TDATA), 4,4',4"-tris{N-(2-naphthyl)-N-phenylamino}-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-dinaphthalene-1-yl)-N,N'-diphenyl-benzidine (NPB), triphenylamine-containing polyether ketone (TPAPEK), 4-isopropyl-4'-methyldiphenyliodonium tetrakis(pentafluorophenyl)borate, etc.

The hole transport layer HTL may include, e.g., a carbazole derivative such as N-phenyl carbazole, and polyvinyl carbazole, a fluorine-based derivative, N,N'-bis(3-methylphenyl)-N,N'-diphenyl-[1,1-biphenyl]-4,4'-diamine (TPD), a triphenylamine-based derivative such as 4,4',4"-tris(N-carbazolyl)triphenylamine (TCTA), N,N'-di(1-naphthyl)-N,N'-diphenylbenzidine (NPB), 4,4'-cyclohexylidene bis[N,N-bis(4-methylphenyl)benzenamine] (TAPC), 4,4'-bis[N,N'-(3-tolyl)amino]-3,3'-dimethylbiphenyl (HMTPD), etc.

The thickness of the hole transport region HTR may be from about 100 Å to about 10,000 Å, e.g., from about 100 Å to about 1,000 Å. In the case where the hole transport region HTR includes both the hole injection layer HIL and the hole transport layer HTL, the thickness of the hole injection layer HIL may be from about 100 Å to about 10,000 Å, e.g., from about 100 Å to about 1,000 Å, and the thickness of the hole transport layer HTL may be from about 30 Å to about 1,000 Å. In the case where the thicknesses of the hole transport region HTR, the hole injection layer HIL, and the hole transport layer HTL satisfy the above-described ranges, satisfactory hole transport properties may be obtained without the substantial increase of a driving voltage.

The hole transport region HTR may further include a charge generating material other than the above-described materials to improve conductivity. The charge generating material may be dispersed in the hole transport region HTR uniformly or non-uniformly. The charge generating material may be, for example, a p-dopant. The p-dopant may be one of a quinone derivative, a metal oxide, or a cyano group-containing compound, without limitation. For example, non-limiting examples of the p-dopant may include a quinone derivative such as tetracyanoquinodimethane (TCNQ), and 2,3,5,6-tetrafluoro-tetracyanoquinodimethane (F4-TCNQ), a metal oxide such as tungsten oxide, and molybdenum oxide, without limitation.

As described above, the hole transport region HTR may further include one of the hole buffer layer or the electron blocking layer other than the hole injection layer HIL and the hole transport layer HTL. The hole buffer layer may compensate an optical resonance distance according to the wavelength of light emitted from the emission layer EML and increase light emission efficiency. Materials included in the hole transport region HTR may be used as materials included in the hole buffer layer. The electron blocking layer is a layer preventing electron injection from the electron transport region ETR to the hole transport region HTR.

The emission layer EML may be provided on the hole transport region HTR. The thickness of the emission layer EML may be, e.g., from about 100 Å to about 1,000 Å. The emission layer EML may have a single layer formed using a single material, a single layer formed using a plurality of different materials, or a multilayer structure having a plurality of layers formed using a plurality of different materials.

Hereinafter, inclusion of the nitrogen-containing compound according to an embodiment of the present disclosure in an emission layer EML will be explained. In an implementation, the nitrogen-containing compound according to an embodiment may be included in at least one organic layer provided between the first electrode EL1 and the second electrode EL2. In an implementation, the nitrogen-containing compound according to an embodiment may be included in the hole transport region HTR. In an implementation, the nitrogen-containing compound according to an embodiment may be included in the hole transport layer HTL.

The emission layer EML may include the nitrogen-containing compound according to an embodiment. For example, the emission layer EML may include a nitrogen-containing compound represented by the following Formula 1.

[Formula 1]

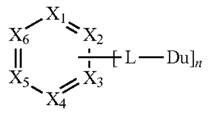

In Formula 1, $X_1$ to $X_6$, L, Du, n, and L are the same as described above.

The emission layer EML may include at least one kind of the nitrogen-containing compound represented by Formula 1. In an implementation, the emission layer EML may further include a suitable material other than the nitrogen-containing compound represented by Formula 1. In an implementation, the emission layer EML may further include a fluorescent material including, e.g., spiro-DPVBi, spiro-6P, 2,2',7,7'-tetrakis(biphenyl-4-yl)-9,9'-spirobifluorene (spiro-sexiphenyl), distyryl-benzene (DSB), distyryl-arylene (DSA), a polyfluorene (PFO)-based polymer, or a poly(p-phenylene vinylene)-based polymer.

In an implementation, the nitrogen-containing compound according to an embodiment may be a material included in the emission layer EML and may radiate delayed fluorescence. For example, the nitrogen-containing compound represented by Formula 1 may be a delayed fluorescence material. In an implementation, the nitrogen-containing compound represented by Formula 1 may be a TADF material.

The nitrogen-containing compound according to an embodiment may include an electron acceptor, a linker, and an electron donor to radiate delayed fluorescence. For example, the hexagonal ring moiety including $X_1$ to $X_6$ may be the electron acceptor, L may be the linker, and Du represented by Formula 2 may be the electron donor. By providing the linker between the electron acceptor and the electron donor, interaction between the electron acceptor and the electron donor may become weak or may attenuate, and a deep blue color emitting device may be easily obtained. In addition, due to the linker provided between the electron acceptor and the electron donor, an energy gap between singlet-triplet may be controlled to be small and, as a result, TADF may be efficiently emitted.

In an implementation, the nitrogen-containing compound according to an embodiment may be a TADF material emitting blue light. In an implementation, the nitrogen-containing compound according to an embodiment may be a TADF material emitting deep blue light. In an implementation, the nitrogen-containing compound according to an embodiment may emit blue light having a wavelength region of about 440 nm to about 480 nm, e.g., about 440 nm to about 475 nm, about 440 nm to about 470 nm, or about 440 nm to about 450 nm.

In an implementation, the compound according to an embodiment may be included as a dopant material of the emission layer.

In an implementation, the nitrogen-containing compound according to an embodiment may have an absolute difference of about 0.2 eV or less between a singlet energy level and a triplet energy level. By controlling the singlet-triplet energy gap small, the TADF may be efficiently emitted.

The emission layer EML may further include a host. In an implementation, the host may include a suitable host material, e.g., tris(8-hydroxyquinolino)aluminum (Alq3), 4,4'-bis(N-carbazolyl)-1,1'-biphenyl (CBP), poly(n-vinylcarbazole) (PVK), 9,10-di(naphthalene-2-yl)anthracene (ADN), 4,4',4"-tris(carbazol-9-yl)-triphenylamine (TCTA), 1,3,5-tris(N-phenylbenzimidazole-2-yl)benzene (TPBi), 3-tert-butyl-9,10-di(naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), bis[2-(diphenylphosphino)phenyl] ether oxide (DPEPO), hexaphenyl cyclotriphosphazene (CP1), 1,4-bis(triphenylsilyl)benzene (UGH2), hexaphenylcyclotrisiloxane ($DPSiO_3$), octaphenylcyclotetra siloxane (DP $SiO_4$), 2,8-bis(diphenylphosphoryl)dibenzofuran (PPF), etc.

In an implementation, the emission layer EML may have a thickness, e.g., of about 10 nm to about 100 nm.

The electron transport region ETR may be provided on the emission layer EML. The electron transport region ETR may include at least one of an electron blocking layer, an electron transport layer ETL, or an electron injection layer EIL.

The electron transport region ETR may have a single layer formed using a single material, a single layer formed using a plurality of different materials, or a multilayer structure including a plurality of layers formed using a plurality of different materials.

In an implementation, the electron transport region ETR may have the structure of a single layer such as the electron injection layer EIL or the electron transport layer ETL, a single layer structure formed using an electron injection material and an electron transport material. In an implementation, the electron transport region ETR may have a single layer structure, or a structure laminated from the first electrode EL1 of electron transport layer ETL/electron injection layer EIL, or hole blocking layer/electron transport layer ETL/electron injection layer EIL. In an implementation, the thickness of the electron transport region ETR may be, e.g., about 1,000 Å to about 1,500 Å.

The electron transport region ETR may be formed using various methods such as a vacuum deposition method, a spin coating method, a cast method, a Langmuir-Blodgett (LB) method, an inkjet printing method, a laser printing method, and a laser induced thermal imaging (LITI) method.

In the case where the electron transport region ETR includes the electron transport layer ETL, the electron transport region ETR may include, e.g., tris(8-hydroxyquinolinato)aluminum (Alq3), 1,3,5-tri[(3-pyridye-phen-3-yl]benzene, 2,4,6-tris(3'-(pyridin-3-yl)biphenyl-3-yl)-1,3,5-triazine, 2-(4-(N-phenylbenzoimidazolyl-1-ylphenyl)-9,10-dinaphthylanthracene, 1,3,5-tri(1-phenyl-1H-benzo[d]imidazol-2-yl)phenyl (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato) aluminum (BAlq), berylliumbis(benzoquinolin-10-olate (Bebq2), 9,10-di(naphthalene-2-yeanthracene (ADN), or a mixture thereof. In an implementation, the thickness of the electron transport layer ETL may be from about 100 Å to about 1,000 Å, e.g., from about 150 Å to about 500 Å. If the thickness of the electron transport layer ETL satisfies the above-described range, satisfactory electron transport properties may be obtained without the substantial increase of a driving voltage.

In the case where the electron transport region ETR includes the electron injection layer EIL, the electron transport region ETR may include, e.g., LiF, lithium quinolate (LiQ), $Li_2O$, BaO, NaCl, CsF, a metal in lanthanoides such as Yb, or a metal halide such as RbCl and RbI. In an implementation, the electron injection layer EIL also may be formed using a mixture material of an electron transport material and an insulating organo metal salt. The organo metal salt may be a material having an energy band gap of about 4 eV or more. In an implementation, the organo metal salt may include, e.g., a metal acetate, a metal benzoate, a metal acetoacetate, a metal acetylacetonate, or a metal stearate. In an implementation, the thickness of the electron injection layer EIL may be from about 1 Å to about 100 Å, e.g., about 3 Å to about 90 Å. In the case where the thickness of the electron injection layer EIL satisfies the above described range, satisfactory electron injection property may be obtained without inducing the substantial increase of a driving voltage.

In an implementation, the electron transport region ETR may include a hole blocking layer, as described above. In an implementation, the hole blocking layer may include, e.g., at least one of 2,9-dimethyl-4,7-diphenyl-1,10-phenanthroline (BCP), or 4,7-diphenyl-1,10-phenanthroline (Bphen).

The second electrode EL2 may be provided on the electron transport region ETR. The second electrode EL2 may be a common electrode or a cathode. The second electrode EL2 may be a transmissive electrode, a transflective electrode, or a reflective electrode. In the case where the second electrode EL2 is the transmissive electrode, the second electrode EL2 may include a transparent metal oxide, e.g., ITO, IZO, ZnO, ITZO, etc.

In the case where the second electrode EL2 is the transflective electrode or the reflective electrode, the second electrode EL2 may include, e.g., Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). In an implementation, the second electrode EL2 may have a multilayered structure including a reflective layer or a transflective layer formed using the above-described materials or a transparent conductive layer formed using ITO, IZO, ZnO, ITZO, etc.

In an implementation, the second electrode EL2 may be connected with an auxiliary electrode. If the second electrode EL2 is connected with the auxiliary electrode, the resistance of the second electrode EL2 may decrease.

In the organic electroluminescence device 10, voltages may be applied to each of the first electrode EL2 and the second electrode EL2, and holes injected from the first electrode EL1 may move via the hole transport region HTR to the emission layer EML, and electrons injected from the second electrode EL2 may move via the electron transport region ETR to the emission layer EML. The electrons and holes may be recombined in the emission layer EML to generate excitons, and the excitons may emit light via transition from an excited state to a ground state.

In the case where the organic electroluminescence device 10 is a top emission type, the first electrode EL1 may be the reflective electrode, and the second electrode EL2 may be the transmissive electrode or transflective electrode. In the case where the organic electroluminescence device 10 is a bottom emission type, the first electrode EL1 may be the transmissive electrode or the transflective electrode, and the second electrode EL2 may be the reflective electrode.

The organic electroluminescence device according to an embodiment may include the nitrogen-containing compound represented by Formula 1, thereby attaining high emission efficiency. For example, the nitrogen-containing compound represented by Formula 1 may emit light via a TAFD process. Accordingly, the organic electroluminescence device according to an embodiment may accomplish high efficiency. In an implementation, the organic electroluminescence device according to an embodiment of the present disclosure may emit blue light via the TAPF process and attain high efficiency.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

(Synthetic Examples)

1. Synthesis of Compound 19

Compound 19, which is a nitrogen-containing compound according to an embodiment, was synthesized by the following reaction.

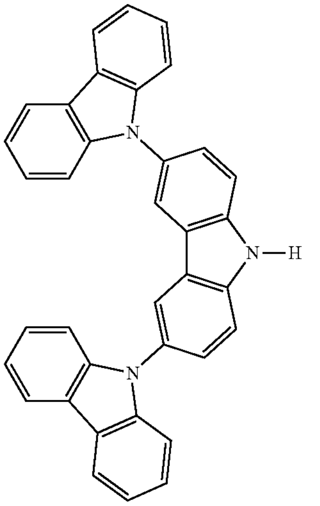

+

A

-continued

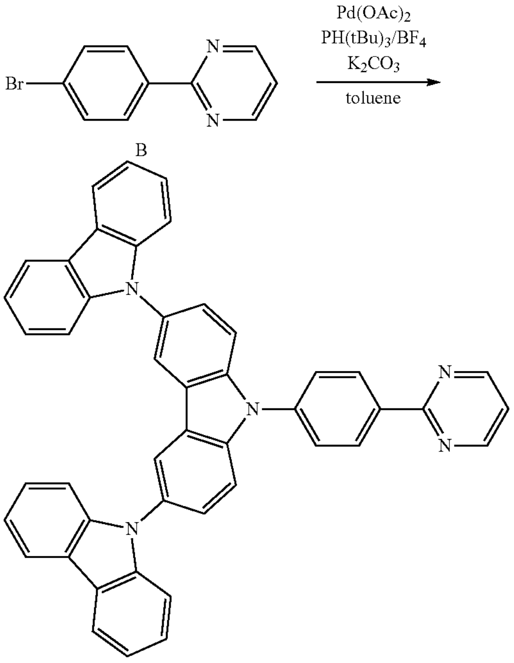

B

19

Under an argon (Ar) atmosphere, 3.1 g of Compound A, 1 g of Compound B, 0.1 g of palladium acetate, 0.25 g of tri-tert-butylphosphonium tetrafluoroborate ($PH(tBu)_3/BF_4$), and 1.77 g of potassium carbonate ($K_2CO_3$) were added to a 100 mL, three-necked flask, followed by heating and refluxing in 50 mL of a toluene solvent at about 130° C. for about 6 hours.

The crude product thus obtained was separated by silica gel column chromatography (using a mixed solvent of dichloromethane and hexane) and then, recrystallized using a mixed solvent of toluene/hexane to obtain 2.77 g (yield 82%) of a white solid compound.

The chemical shift values (δ) of the white solid compound measured by $^1H$ NMR were $^1H$ NMR (300 MHz, $CDCl_3$, δ): 8.92 (d, J=8.7 Hz, 2H), 8.88 (d, J=8.1 Hz, 2H), 8.28 (s, 2H), 8.14 (d, J=7.1 Hz, 2H), 7.89 Hz (d, J=8.7 Hz, 2H), 7.76 (d, J=8.7 Hz, 2H), 7.66-7.63 (m, 2H), 7.41-7.32 (m, 8H), 7.31-7.24 (m, 5H). In addition, the molecular weight of the white solid compound measured by FAB-MS was 651. Through the results, the white solid compound was identified as Compound 19.

2. Synthesis of Compound 53

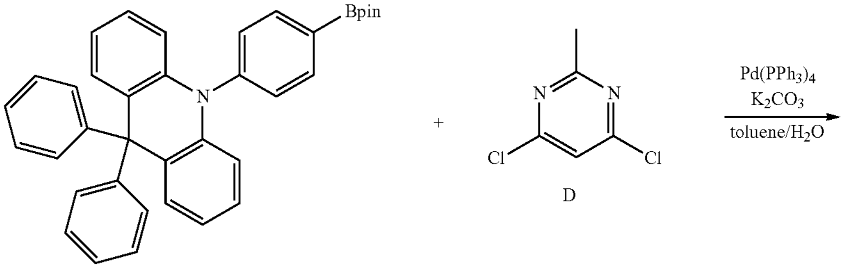

C

+

D

-continued

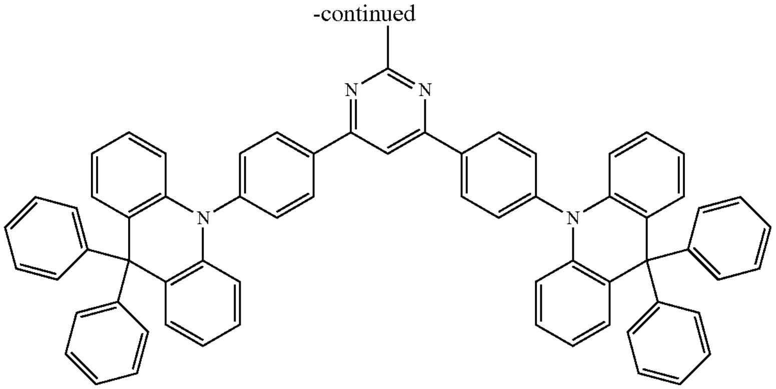

53

Under a nitrogen ($N_2$) atmosphere, 2.00 g of Compound C, 0.24 g of Compound D, 0.13 g of tetrakis(triphenylphosphine)palladium(0) [$Pd(PPh_3)_4$] and 80 mL of dehydrated toluene were added to a 300 mL, three-necked flask, followed by stirring. An aqueous potassium carbonate ($K_2CO_3$) solution (30 mL, 1.55 g) was added thereto, followed by heating and refluxing for about 48 hours. The crude product thus obtained was filtered using Celite, extracted with chloroform, and dried with sodium sulfate ($Na_2SO_4$). After removing solvents, the crude product was separated by silica gel column chromatography (using a mixed solvent of hexane/ethyl acetate/chloroform) to obtain 1.94 g (yield 57%) of a light yellow solid compound.

The chemical shift values (δ) of the white solid compound measured by $^1H$ NMR were $^1H$ NMR (400 MHz, DMSO-$d_6$, δ): 8.60 (d, J=8.0 Hz, 5H), 7.37-7.25 (m, 16H), 7.12 (t, J=7.2 Hz, 4H), 6.95-6.92 (m, 12H), 6.80 (d, J=6.8 Hz, 4H), 6.44 (d, J=8.4 Hz, 4H), 2.81 (s, 3H). In addition, the molecular weight of the compound measured by MALDI-TOF-MS was 909.65. Through the results, the light yellow solid compound was identified as Compound 53.

3. Synthesis of Compound 55

Under a nitrogen ($N_2$) atmosphere, 2.00 g of Compound C, 0.25 g of Compound E, 40.10 g of tetrakis(triphenylphosphine)palladium(0) [$Pd(PPh_3)_4$] and 80 mL of dehydrated toluene were added to a 300 mL, three-necked flask, followed by stirring. An aqueous potassium carbonate ($K_2CO_3$) solution (30 mL, 0.93 g) was added thereto, followed by heating and refluxing for about 24 hours. The crude product thus obtained was filtered using Celite, extracted with chloroform, and dried with sodium sulfate ($Na_2SO_4$). After removing solvents, the crude product was separated by silica gel column chromatography (using a mixed solvent of hexane/ethyl acetate/chloroform) to obtain 2.70 g (yield 80%) of a light yellow solid compound.

The chemical shift values (δ) of the white solid compound measured by $^1H$ NMR were $^1H$ NMR (400 MHz, $CDCl_3$, δ): 9.07 (s, 2H), 8.33 (d, J=8.4 Hz, 4H), 7.28-7.26 (m, 16H), 7.07-7.01 (m, 12H), 6.92-6.91 (m, 8H), 6.51 (d, J=8.1 Hz, 4H). Through the results, the light yellow solid compound was identified as Compound 55.

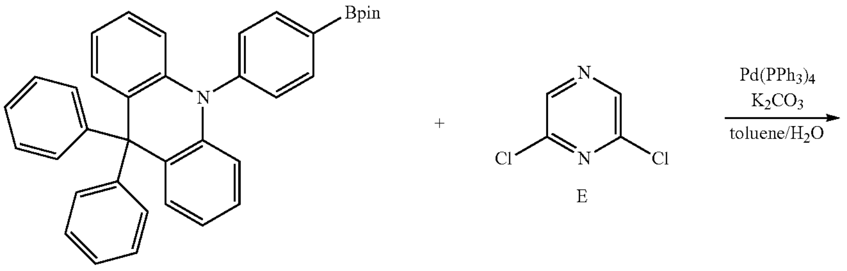

C

E

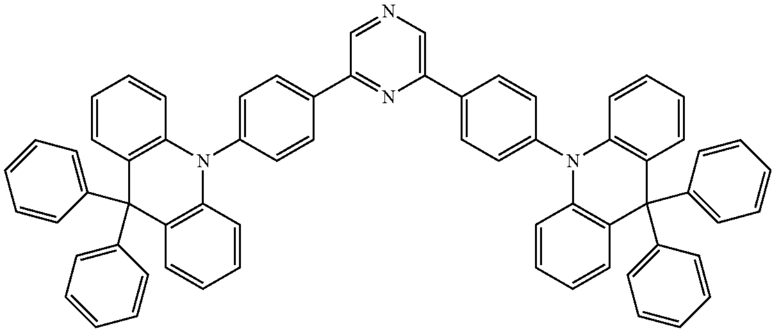

55

4. Synthesis of Compound 61

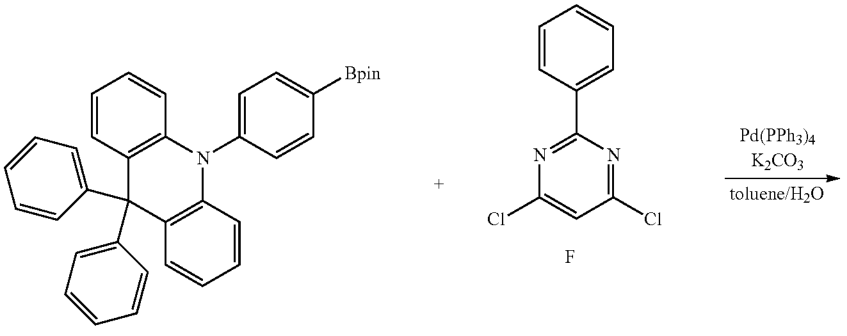

F

C

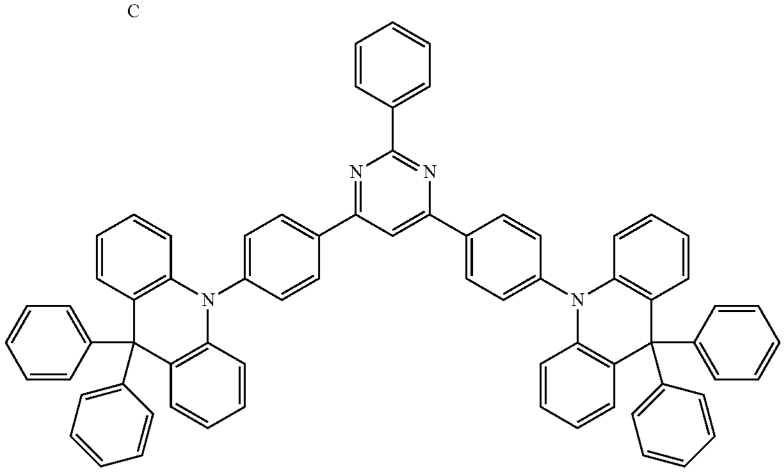

61

Under a nitrogen ($N_2$) atmosphere, 2.00 g of Compound C, 0.30 g of Compound F, 40.13 g of tetrakis(triphenylphosphine)palladium(0) [$Pd(PPh_3)_4$] and 80 mL of dehydrated toluene were added to a 300 mL, three-necked flask, followed by stirring. An aqueous potassium carbonate ($K_2CO_3$) solution (30 mL, 1.55 g) was added thereto, followed by heating and refluxing for about 48 hours. The crude product thus obtained was filtered using Celite, extracted with chloroform, and dried with sodium sulfate ($Na_2SO_4$). After removing solvents, the crude product was separated by silica gel column chromatography (using a mixed solvent of hexane/ethyl acetate/chloroform) to obtain 2.36 g (yield 65%) of a light yellow solid compound.

The chemical shift values (δ) measured by $^1$H NMR were $^1$H NMR (400 MHz, DMSO-$d_6$, δ): 8.77 (d, J=8.4 Hz, 4H), 8.74-8.71 (m, 3H), 7.64-7.61 (m, 3H), 7.38-7.28 (m, 16H), 7.13 (t, J=8.0 Hz, 4H), 6.96-6.93 (m, 12H), 6.81 (d, J=8.0 Hz, 4H), 6.48 (d, J=8.4 Hz, 4H). In addition, the molecular weight of the compound measured by MALDI-TOF-MS was 971.51. Through the results, the light yellow solid compound was identified as Compound 61.

5. Synthesis of Compound 66

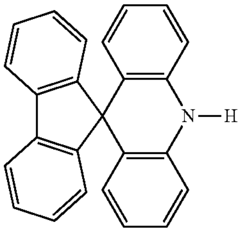

G

+

-continued

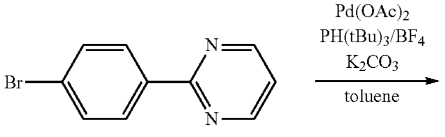

B

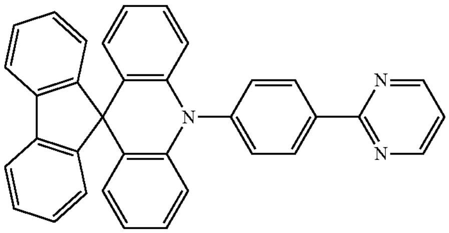

66

Under a nitrogen ($N_2$) atmosphere, 1.41 g of Compound G, 1.0 g of Compound B, 0.01 g of palladium acetate, 0.01 g of tri-tert-butylphosphonium tetrafluoroborate ($PH(tBu)_3/BF_4$), and 1.76 g of potassium carbonate ($K_2CO_3$) were added to a 100 mL, three-necked flask, followed by heating and refluxing in 30 mL of a toluene solvent at about 110° C. for about 12 hours. The crude product thus obtained was separated by silica gel column chromatography (using a mixed solvent of dichloromethane and hexane) and recrystallized using a mixed solvent of toluene/hexane to obtain 1.8 g (yield 90%) of a white solid compound.

The chemical shift values (δ) of the white solid compound measured by $^1$H NMR were $^1$H NMR (400 MHz, $CDCl_3$, δ):

8.90 (d, J=4.8 Hz, 2H), 8.79 (d, J=8.8 Hz, 2H), 7.79 (d, J=7.3 Hz, 2H), 7.65 (d, J=8.4 Hz, 2H), 7.46 (d, J=8.5 Hz, 2H), 7.38 (t, J=6.6 Hz, 2H), 7.30-7.26 (m, 3H), 6.92 (t, J=7.0 Hz, 2H), 6.58 (t, J=6.6 Hz, 2H), 6.43 (t, 8.8 Hz, 4H). Through the results, the light yellow solid compound was identified as Compound 66.

6. Synthesis of Compound 67

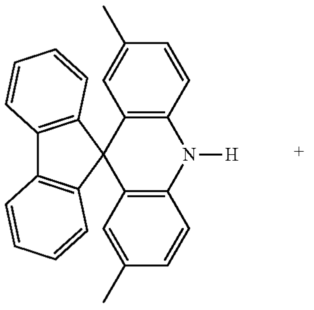

H

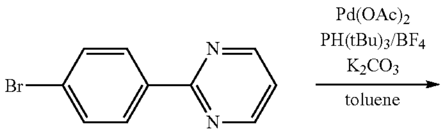

B

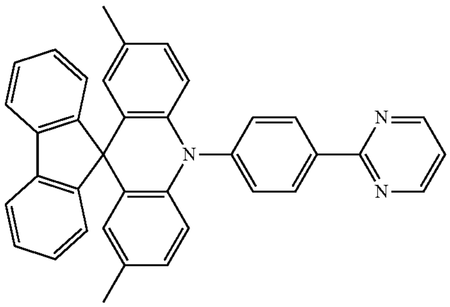

67

Under an argon (Ar) atmosphere, 2.9 g of Compound H, 1.6 g of Compound B, 0.11 g of palladium acetate, 0.28 g of tri-tert-butylphosphonium tetrafluoroborate ($PH(tBu)_3/BF_4$), and 2.88 g of potassium carbonate ($K_2CO_3$) were added to a 100 mL, three-necked flask, followed by heating and refluxing in 34 mL of a toluene solvent (about 110° C.) for about 5 hours. The crude product thus obtained was separated by silica gel column chromatography (using a mixed solvent of dichloromethane and hexane) and recrystallized using a mixed solvent of toluene/hexane to obtain 3.4 g (yield 98%) of a white solid compound.

The chemical shift values (δ) of the white solid compound measured were $^1$H NMR (300 MHz, $CDCl_3$, δ): 8.90 (d, J=5.1 Hz, 2H), 8.90 (d, J=8.7 Hz, 2H), 7.83 (d, J=1.2 Hz, 2H), 7.62 (d, J=8.7 Hz, 2H), 7.46-7.41 (m, 3H), 7.39-7.30 (m, 4H), 6.72 (d, J=6H), 6.33 (d, J=8.7 Hz, 2H), 6.20-6.19 (m, 2H), 1.95 (s, 6H). The molecular weight of the white solid compound measured by FAB-MS was 514. Through the results, the white solid compound was identified as Compound 67.

7. Synthesis of Compound 69

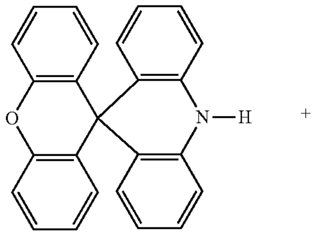

I

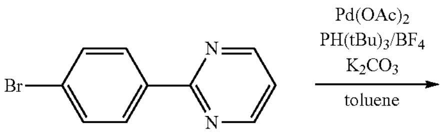

B

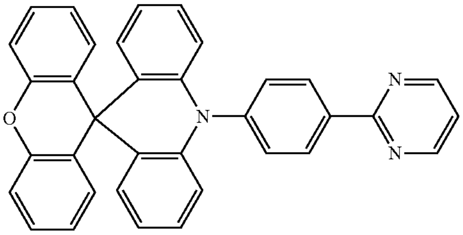

69

Under a nitrogen ($N_2$) atmosphere, 2.96 g of Compound I, 2.00 g of Compound B, 0.02 g of palladium acetate, 40.03 g of tri-tert-butylphosphonium tetrafluoroborate ($PH(tBu)_3/BF_4$), and 3.53 g of potassium carbonate were added to a 100 mL, three-necked flask, followed by heating and refluxing in 100 mL of a toluene solvent (about 110° C.) for about 12 hours. The crude product thus obtained was separated by silica gel column chromatography (using a mixed solvent of dichloromethane and hexane) and recrystallized using a mixed solvent of toluene/hexane to obtain 2.80 g (yield 66%) of a white solid compound.

The chemical shift values (δ) of the white solid compound measured by were $^1$H NMR (400 MHz, $CDCl_3$, δ): 8.90 (d, J=5.1 Hz, 2H), 8.77 (d, J=8.4 Hz, 2H), 7.59 (d, J=8.4 Hz, 2H), 7.29 (d, J=4.8 Hz, 2H), 7.20-7.17 (m, 6H), 6.99-6.95 (m, 2H), 6.90-6.86 (m, 4H), 6.69 (t, J=7.3 Hz, 2H), 6.36 (d, J=8.8 Hz, 2H). Through the results, the white solid compound was identified as Compound 69.

8. Synthesis of Compound 70

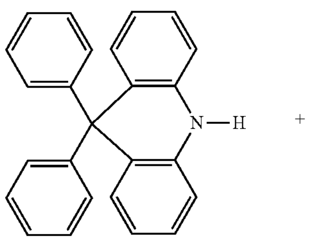

G

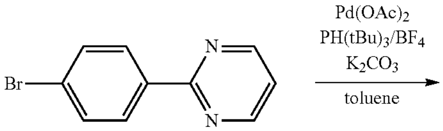

B

-continued

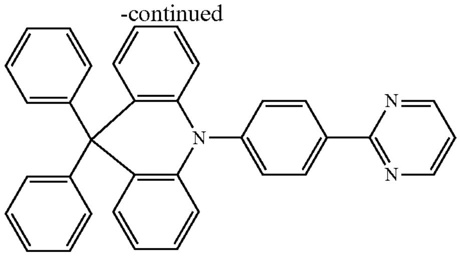

70

Under a nitrogen ($N_2$) atmosphere, 1.42 g of Compound G, 1.00 g of Compound B, 0.01 g of palladium acetate, 0.01 g of $PH(tBu)_3/BF_4$, and 1.40 g of potassium carbonate were added to a 100 mL, three-necked flask, followed by heating and refluxing in 30 mL of a toluene solvent (about 110° C.) for about 6 hours. The crude product thus obtained was separated by silica gel column chromatography (using a mixed solvent of dichloromethane and hexane) and recrystallized using a mixed solvent of toluene/hexane to obtain 1.87 g (yield 90%) of a white solid compound.

The chemical shift values (δ) of the white solid compound measured were $^1H$ NMR (400 MHz, $CDCl_3$, δ): 8.85 (d, J=4.8 Hz, 2H), 8.60 (d, J=8.4 Hz, 2H), 7.27-7.21 (m, 9H), 7.06-7.01 (m, 6H), 6.90-6.88 (m, 4H), 6.49 (d, J=8.4 Hz, 2H). Through the results, the white solid compound was identified as Compound 70.

9. Synthesis of Compound 71

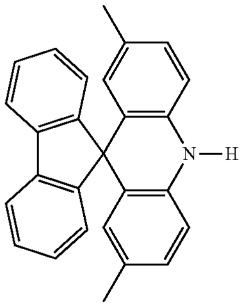

+

H

-continued

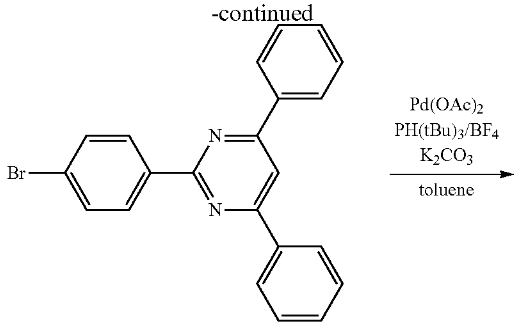

J

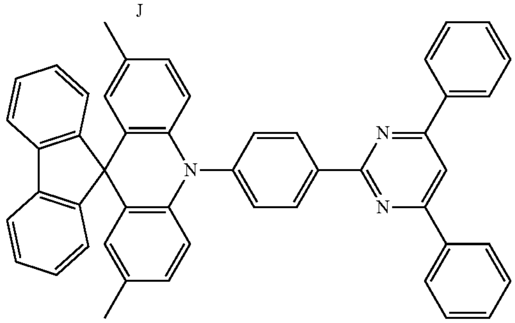

71

Under an argon (Ar) atmosphere, 1.46 g of Compound H, 1.52 g of Compound J, 0.061 g of palladium acetate, 0.16 g of $PH(tBu)_3/BF_4$, and 1.64 g of potassium carbonate were added to a 100 mL, three-necked flask, followed by heating and refluxing in 77 mL of a toluene solvent (about 110° C.) for about 4 hours. The crude product thus obtained was separated by silica gel column chromatography (using a mixed solvent of dichloromethane and hexane) and recrystallized using a mixed solvent of toluene/hexane to obtain 2.17 g (yield 84%) of a white solid compound.

The chemical shift values (δ) of the white solid compound measured were $^1H$ NMR (400 MHz, $CDCl_3$, δ): 9.03 (d, J=8.7 Hz, 2H), 8.37-8.35 (m, 4H), 8.11 (s, 1H), 7.83 (d, J=8.7 Hz, 2H), 7.67-7.61 (m, 8H), 7.47 (d, J=1.5 Hz, 2H), 7.40 (t, J=12 Hz, 2H), 7.31-7.29 (m, 2H), 6.73 (d, J=8.4 Hz, 2H), 6.39 (d, J=8.4 Hz, 2H), 6.19 (s, 2H), 1.96 (s, 6H). The molecular weight of the compound measured by FAB-MS was 666. Through the results, the white solid compound was identified as Compound 71.

(Device Manufacturing Example)

Organic electroluminescence devices of Examples 1 to 5 were manufactured using Compounds 53, 55, 61, 67, and 71 as emission layer materials.

[Example Compounds]

53

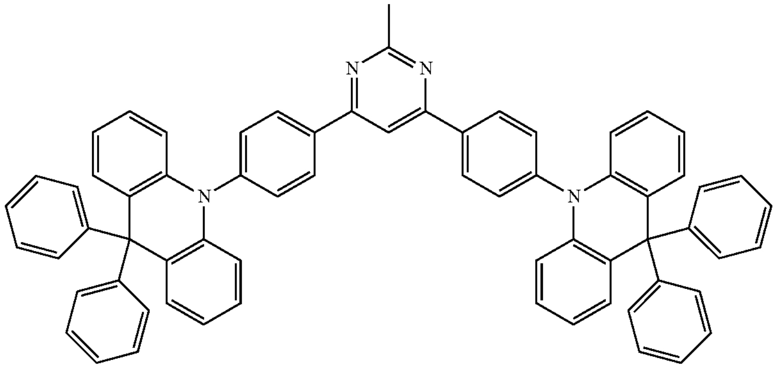

-continued

55

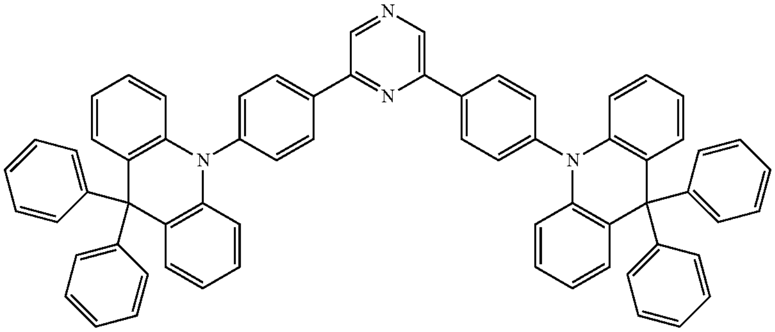

61

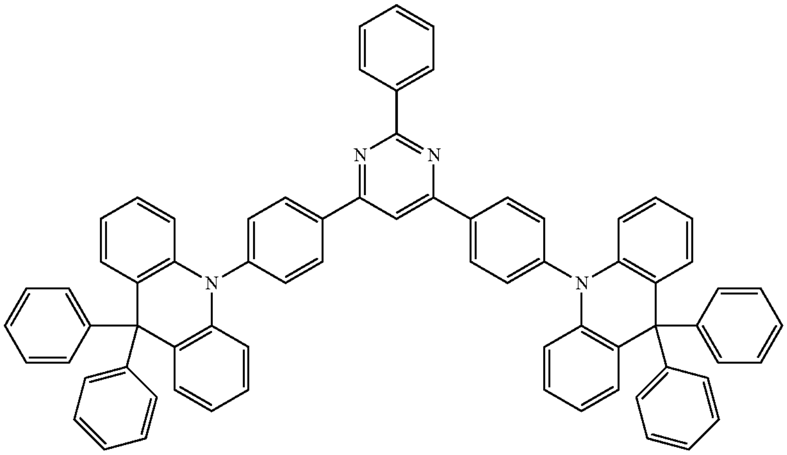

67

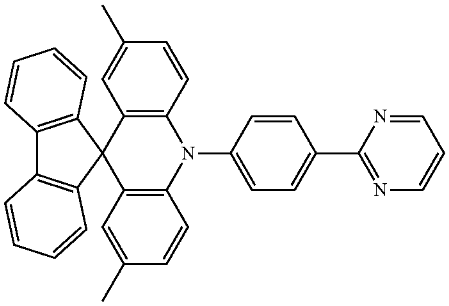

71

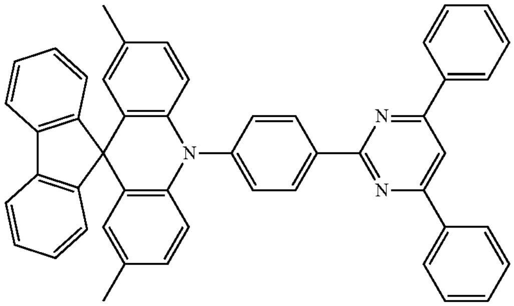

Organic electroluminescence devices of Comparative Examples 1 and 2 were manufactured using the following Comparative Compounds X1 and X2 as emission layer materials.

[Comparative Compounds]

X-1

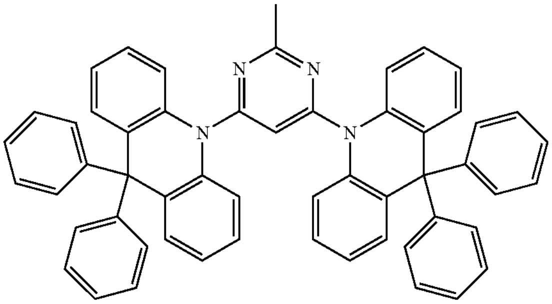

-continued

X-2

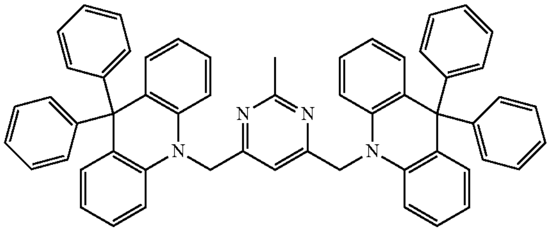

The organic electroluminescence devices of Examples 1 to 5 and Comparative Examples 1 and 2 were manufactured as follows. On a glass substrate, ITO with a thickness of about 150 nm was patterned, washed with ultrapure water, and treated with UV-ozone for about 10 minutes. After that, a hole injection layer with a thickness of about 10 nm was formed using HAT-CN, a hole transport layer with a thickness of about 80 nm was formed using NPB, an emission layer in which the above-described nitrogen-containing compound is doped in a doping amount of 18% in a DPEPO host material and having a layer thickness of about 20 nm was formed, an electron transport layer with a thickness of about 30 nm was formed using TPBi, an electron injection layer with a thickness of about 0.5 nm was formed using LiF, and a second electrode with a thickness of about 100 nm was formed using aluminum (Al). Each layer and the second electrode were formed by a resistance heating method using a vacuum deposition apparatus.

After that, the maximum emission wavelength and external quantum efficiency of the organic electroluminescence devices thus manufactured were measured. The maximum emission wavelength was obtained using deposited specimens of target compounds for measuring on a quartz glass plate by measuring the maximum emission wavelength of an emission spectrum at room temperature (about 300 K). The external quantum efficiency was measured using an external quantum efficiency measurement apparatus C9920-2-12 of HAMAMATSU Photonics Co. The measured results are shown in the following Table 1. The difference $\Delta E_{ST}$ of a singlet energy level and a triplet energy level was calculated using Gaussian09 by a function B3LYP, 6-31G(d).

TABLE 1

| Device manufacturing example | Dopant material in emission layer | $\Delta E_{ST}^{(b)}$ | λmax | External quantum efficiency EQE % |
|---|---|---|---|---|
| Example 1 | Compound 53 | 0.01 | 461 | 18.7 |
| Example 2 | Compound 55 | 0.01 | 446 | 9.5 |
| Example 3 | Compound 61 | 0.01 | 469 | 14.8 |
| Example 4 | Compound 67 | 0.01 | 462 | 9.9 |
| Example 5 | Compound 71 | 0.01 | 468 | 20.5 |
| Comparative Example 1 | Comparative Compound X-1 | 0.01 | 490 | 20.9 |
| Comparative Example 2 | Comparative Compound X-2 | 0.01 | 525 | 13.3 |

When comparing Example 1 and Comparative Example 1, the maximum emission wavelength of Example 1 (in which the emission material included a linker between a donor and an acceptor) was decreased to shorter wavelength by about 30 nm, when compared to that of Comparative Example 1 (in which an emission material did not include a linker). In addition, the emission wavelength of Comparative Example 2 (in which the emission material included an alkyl group between an electron donor and an electron acceptor) was increased to longer wavelength, when compared to that of Example 1, e.g., due to the weakening of the electron donating property of the electron donor. Selecting an appropriate linker may have an effect on the separation of HOMO-LUMO orbital.

By way of summation and review, the application of the organic electroluminescence device to a display, driving voltage may be decreased and emission efficiency and life may be increased. To stably achieve such effects, materials for the organic electroluminescence device may be developed.

For example, various fluorescent materials to attain an organic electroluminescence device with high efficiency have been developed. For example, a technique may attain the high efficiency of a fluorescent device based on triplet-triplet annihilation (TTA) due to the collision of triplet excitons. According to the technique, singlet excitons, of which theoretical production ratio is only about 25%, may be produced up to about 40%. The production ratio may increase to about twice that of other fluorescent devices. The loss of triplet excitons may be also included.

Fluorescent emission by thermally activated delayed fluorescence (TADF) may have theoretical production efficiency of singlet excitons of about 100%, and may rapidly increase emission efficiency. For example, various TADF materials may exhibit red and/or green color. TADF materials exhibiting blue color with high efficiency may be rarely reported. For the application to a full color device, a blue emitting device using the TADF may be used.

TADF materials may have a nitrogen-containing polycyclic structure and may be green emitting materials. Materials exhibiting blue-green emission may have not have ideal efficiency. An organic electroluminescence device using TADF materials may emit sky blue color. The material may not emit blue color with short wavelength of about 480 nm or less, which is suitable for a display.

Compounds having TADF material properties may be applied to organic electroluminescence devices. The embodiments may provide pyridine-, pyrimidine-, pyridazine-, pyrazine-based compounds from which a π-conjugation system is not diffused, which emit blue light. For example, a compound according to an embodiment may have a combined structure of an acceptor having a pyridine-, pyrimidine-, pyridazine-, pyrazine-based skeleton with a donor, which may be used in an organic electroluminescence device emitting blue light with high efficiency.

The embodiments may provide a compound emitting blue to deep blue color, and a blue emitting material with short wavelength may be obtained by reinforcing the electron donating property as in Example 1.

By introducing a substituent to the compound represented by Formula 1 according to an embodiment, blue emission may be attained, and at the same time, high external quantum efficiency may be accomplished.

The compound according to an embodiment may be used as a material for an organic electroluminescence device.

The compound according to an embodiment may be used as a TADF material.

The compound according to an embodiment may increase or improve the emission efficiency of an organic electroluminescence device.

The embodiments may provide a nitrogen-containing compound with improved emission efficiency.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A nitrogen-containing compound represented by the following Formula 1:

[Formula 1]

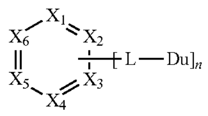

wherein, in Formula 1, $X_1$ to $X_6$ are each independently $CR_1$ or N, provided that one or two of $X_1$ to $X_6$ are N and the others are $CR_1$, each $R_1$ is independently a bond to L, a hydrogen atom, a deuterium atom, a halogen atom, a substituted or unsubstituted alkyl group having 1 to 30 carbon atoms, a substituted or unsubstituted aryl group having 6 to 30 ring carbon atoms, or a substituted or unsubstituted heteroaryl group having 2 to 30 ring carbon atoms, L is a substituted or unsubstituted arylene group having 6 to 30 ring carbon atoms, n is 1 or 2, and when only one of $X_1$ to $X_6$ is N, Du is a group represented by one selected from the following Formulae 8 to 9 and 13 to 16, and when only two of $X_1$ to $X_6$ are N, Du is a group represented by one selected from the following Formulae 7 to 9 and 12 to 16,

[Formula 7]

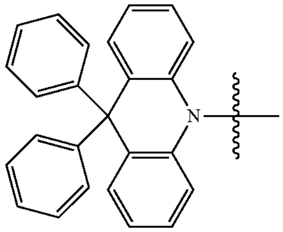

[Formula 8]

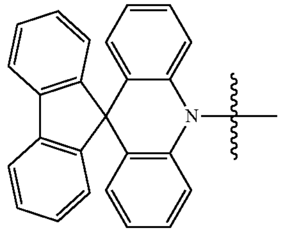

[Formula 9]

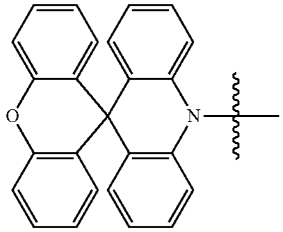

[Formula 12]

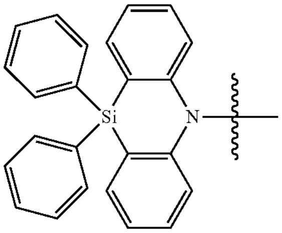

-continued

[Formula 13]

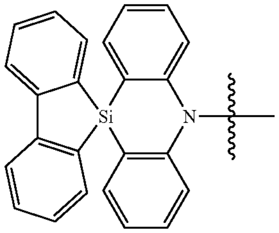

[Formula 14]

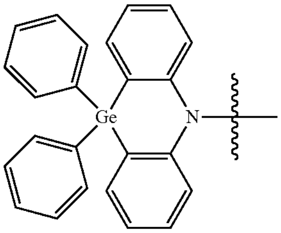

[Formula 15]

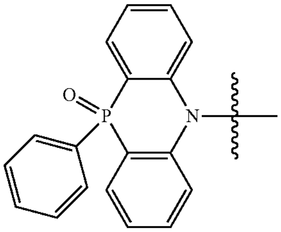

[Formula 16]

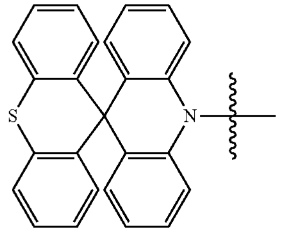

.

wherein, in Formulae 7 to 9 and 12 to 16,

represents a bonding site with L of Formula 1.

2. The nitrogen-containing compound as claimed in claim 1, wherein L is a substituted or unsubstituted phenylene group.

3. The nitrogen-containing compound as claimed in claim 1, wherein the nitrogen-containing compound represented by Formula 1 is represented by the following Formula 3:

[Formula 3]

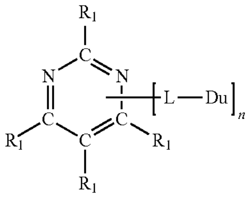

wherein, in Formula 3, L, Du, $R_1$, and n are defined the same as those of Formula 1.

4. The nitrogen-containing compound as claimed in claim 1, wherein the nitrogen-containing compound represented by Formula 1 is represented by the following Formula 4:

[Formula 4]

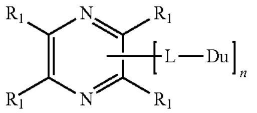

wherein, in Formula 4, L, Du, $R_1$, and n are defined the same as those of Formula 1.

5. The nitrogen-containing compound as claimed in claim 1, wherein the nitrogen-containing compound represented by Formula 1 is represented by the following Formula 5:

[Formula 5]

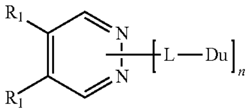

wherein, in Formula 5, L, Du, $R_1$, and n are defined the same as those of Formula 1.

6. A nitrogen-containing compound, wherein the nitrogen-containing compound is one of the following Compounds:

8

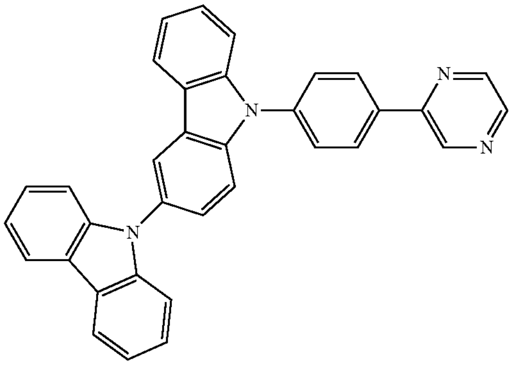

9

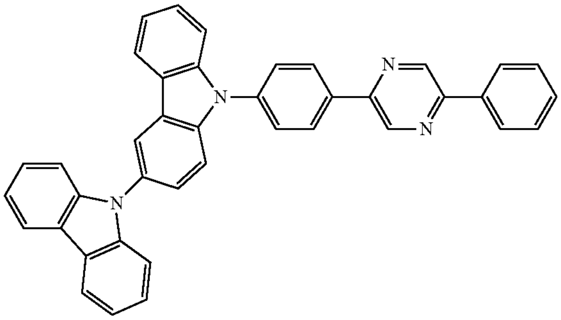

10

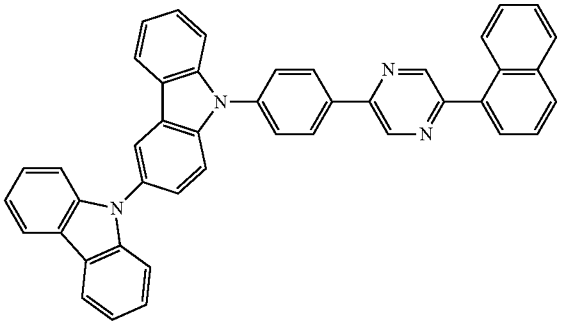

11

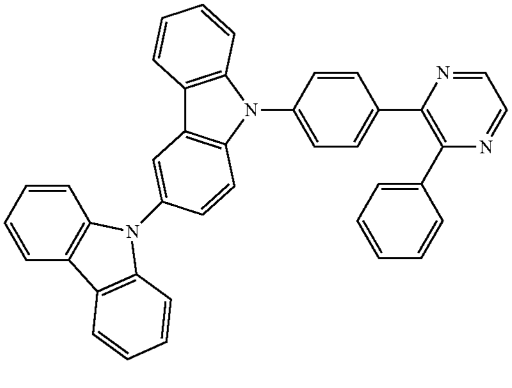

12

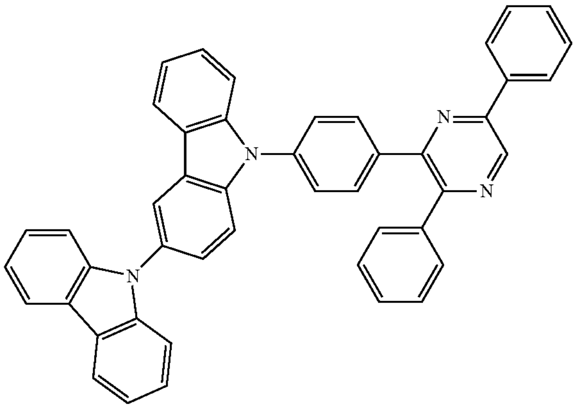

37

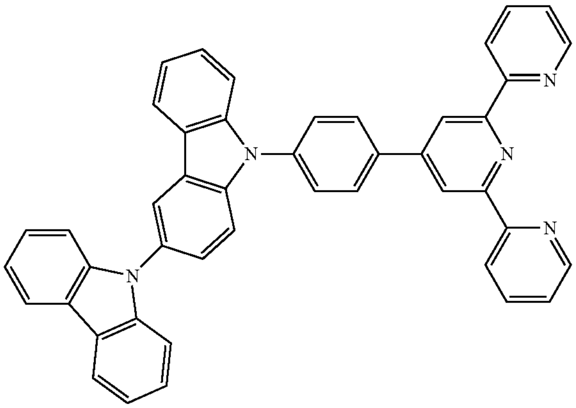

-continued
7
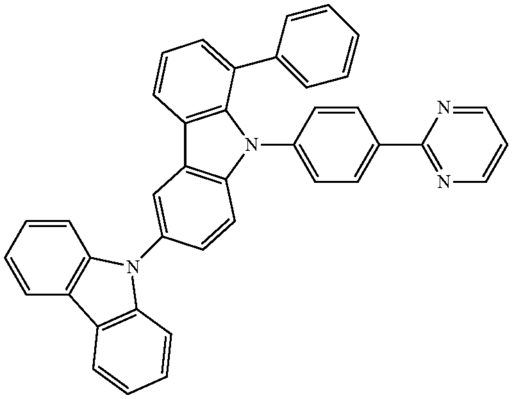
8
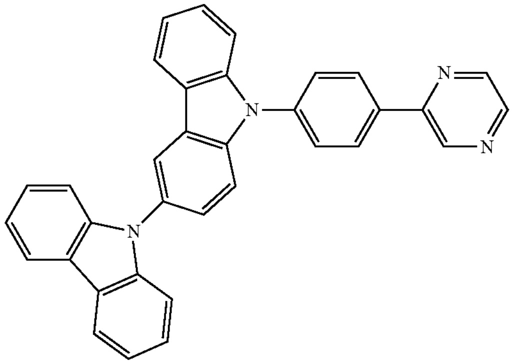
39
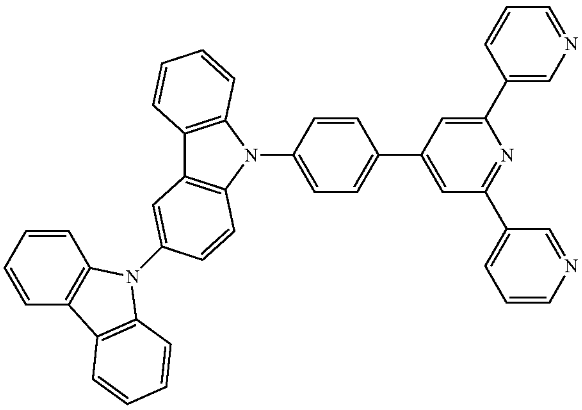
38
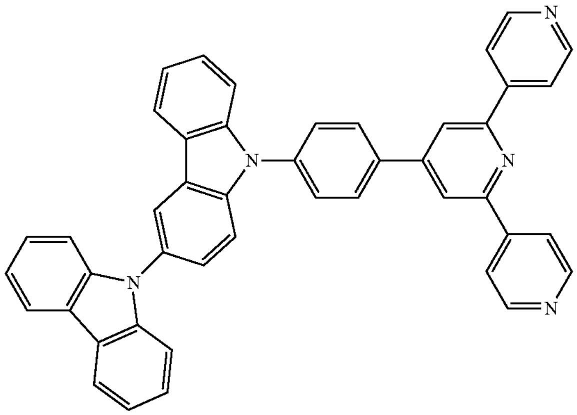
44
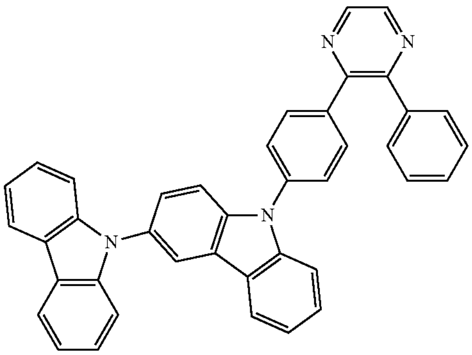
53
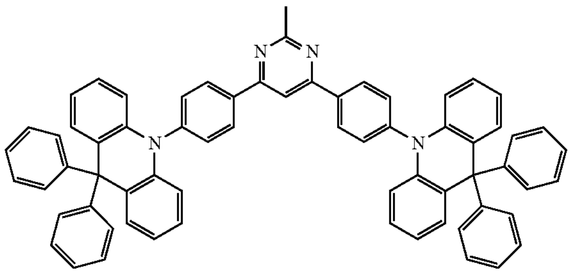
54
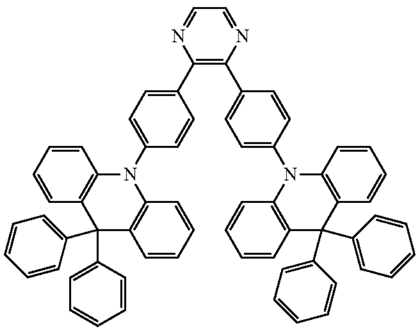
55
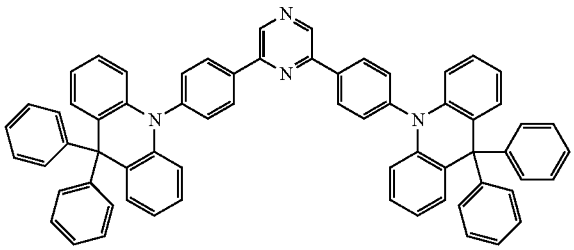

-continued
56
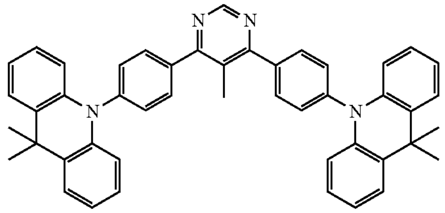
57
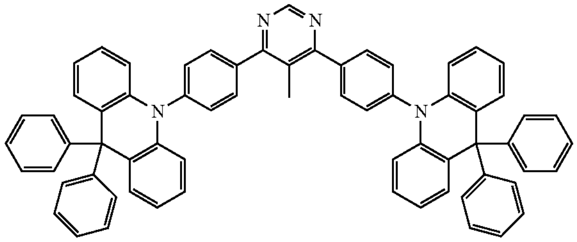
58
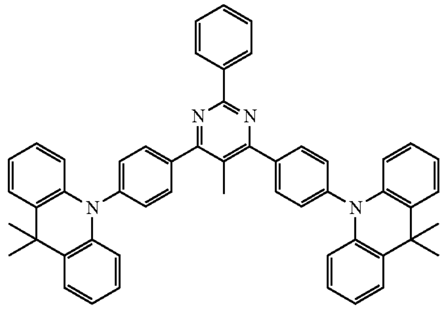
59
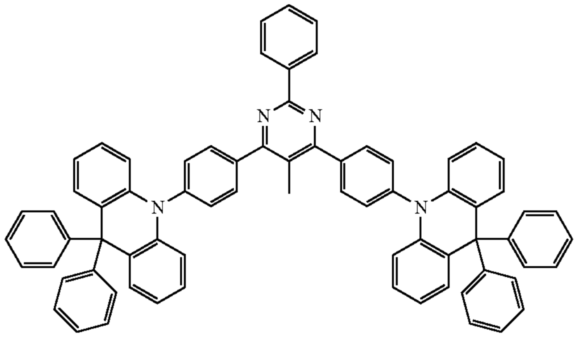
60
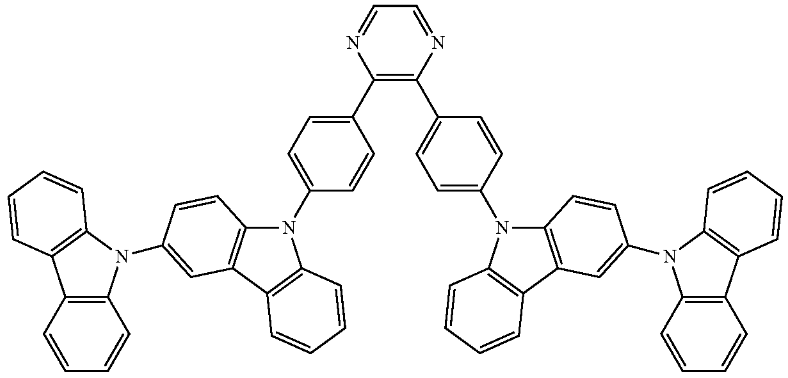
61
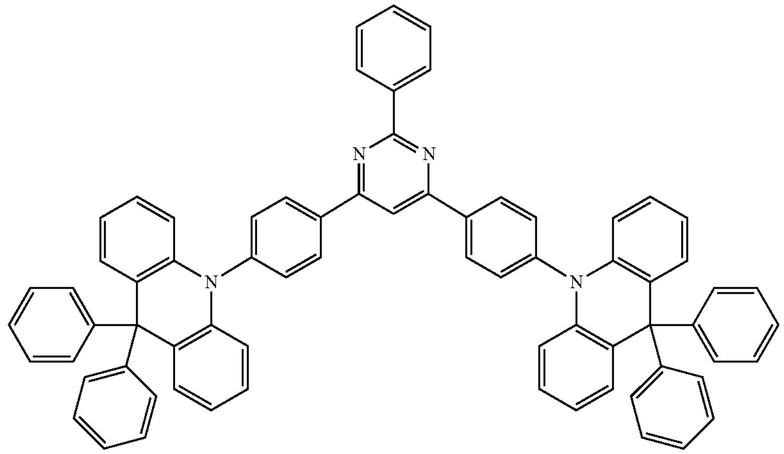

-continued
62
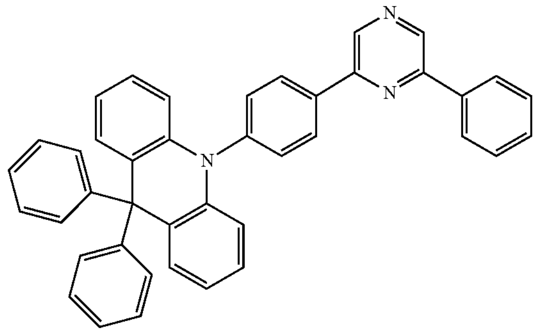
63
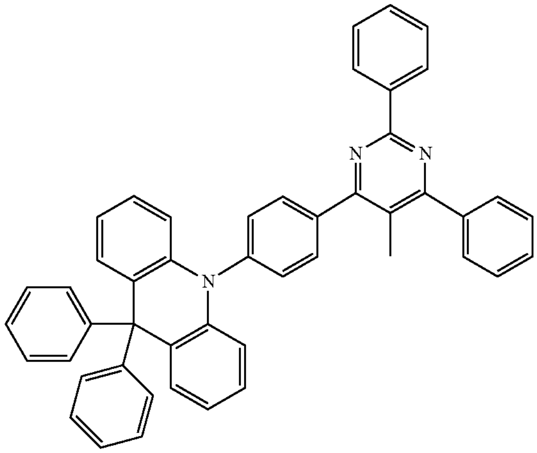
64
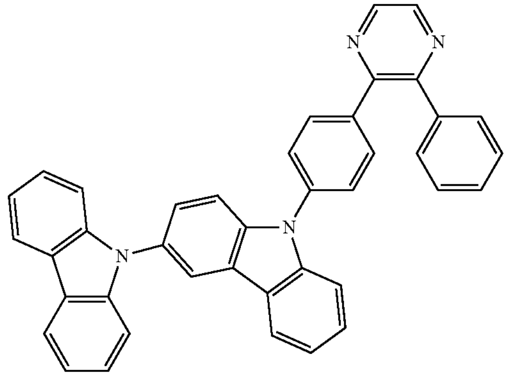
65
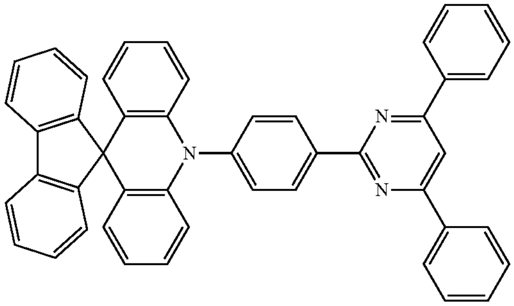
66
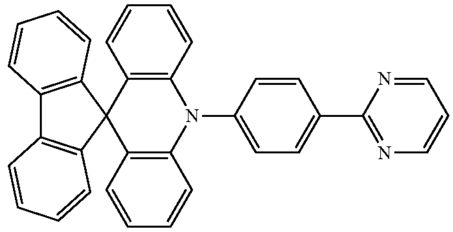
67
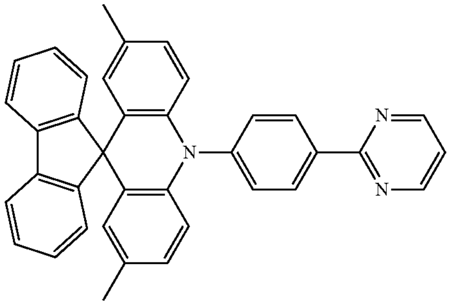
68
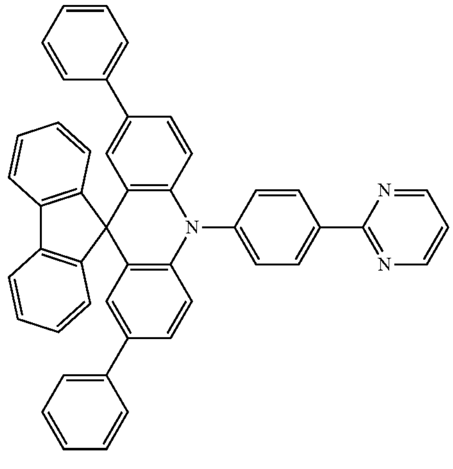
69
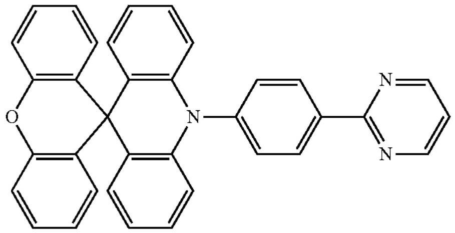

-continued
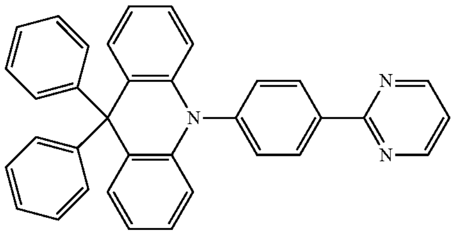
70
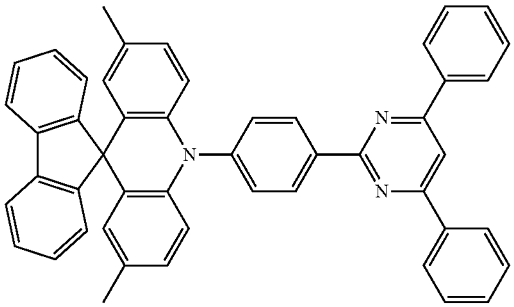
71
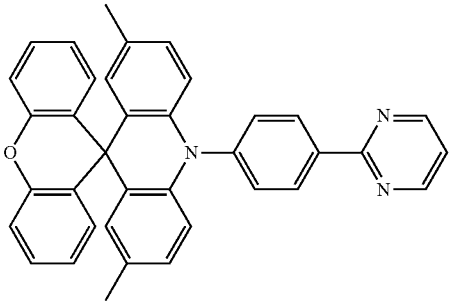
72
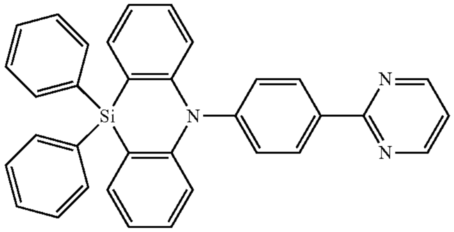
73
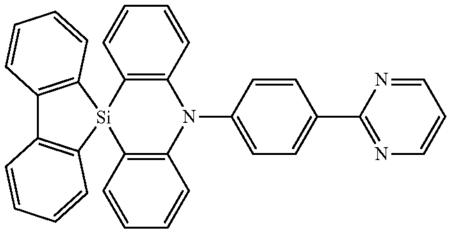
74
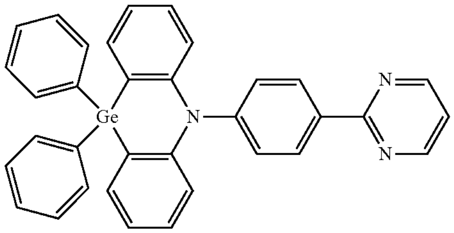
75
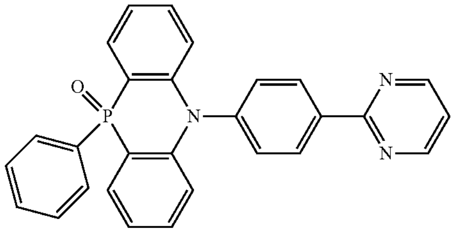
76
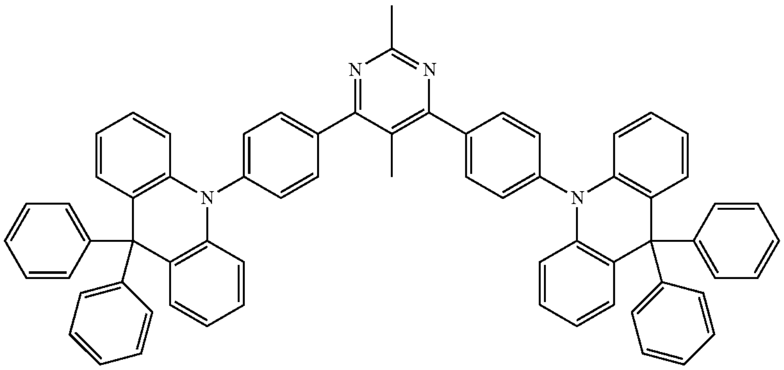
77

-continued
78
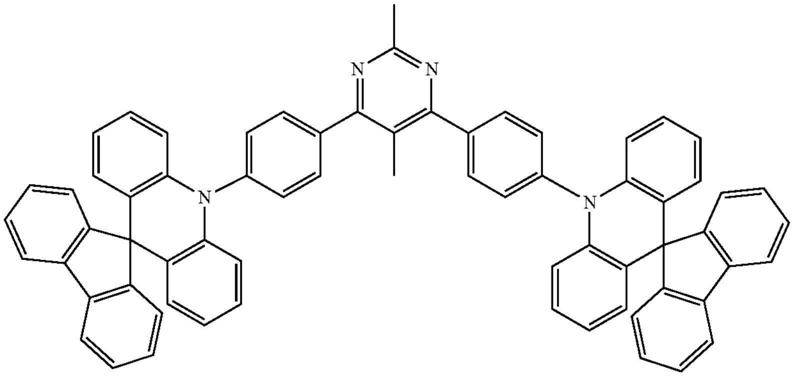
79
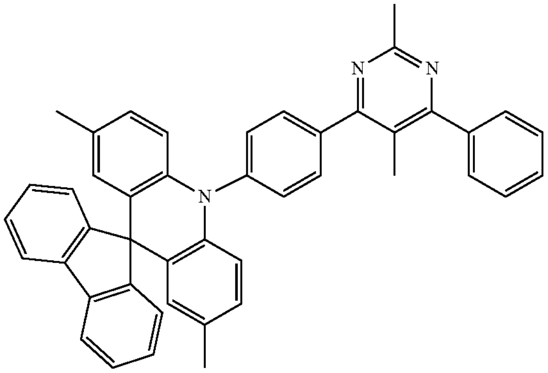
80
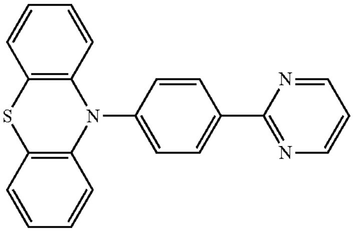
81
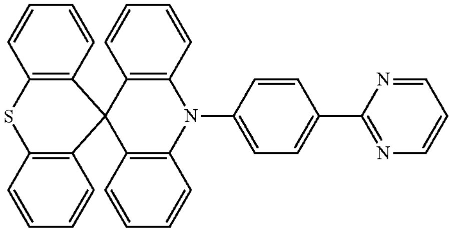
82
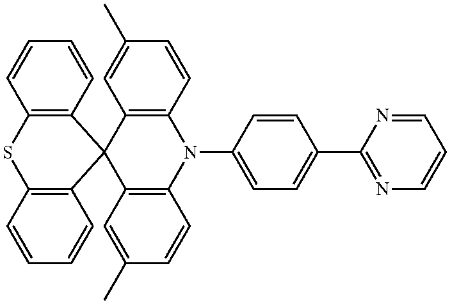
83
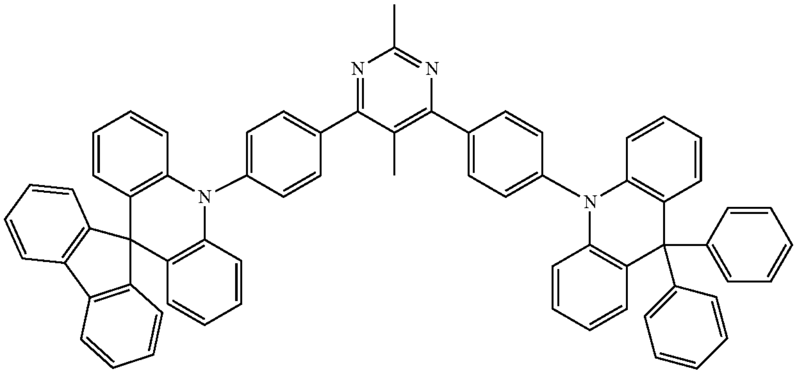

-continued
84
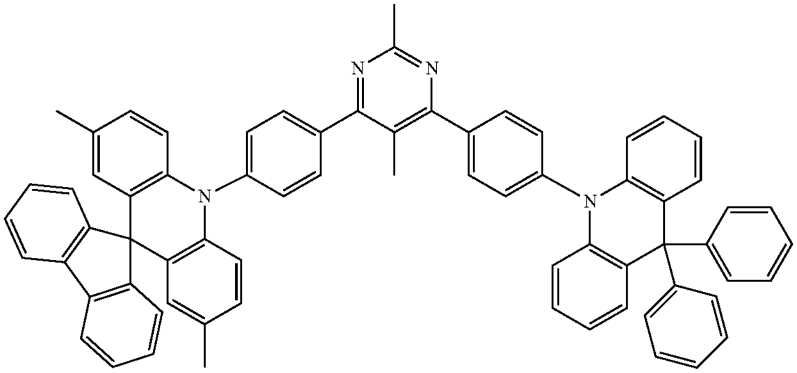
85
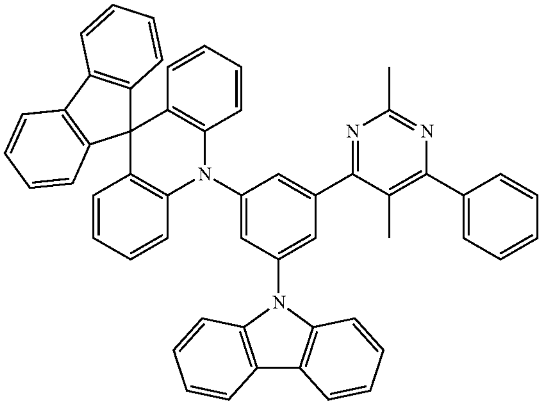
86
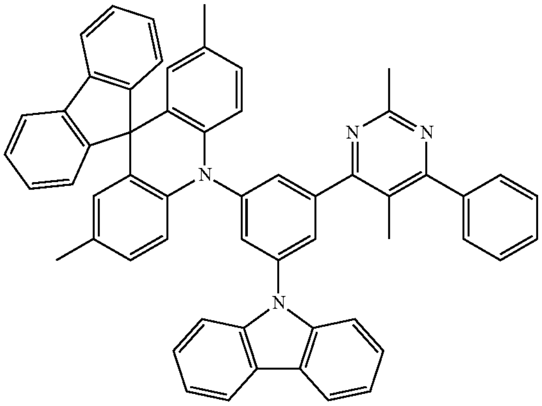
87
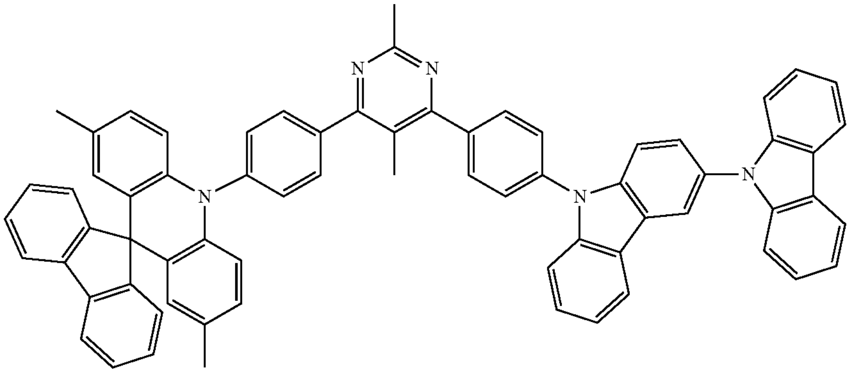
88
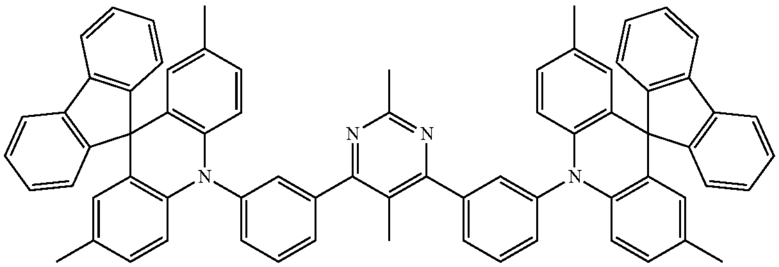

-continued
89
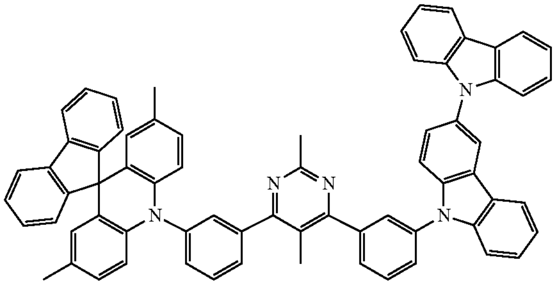
90
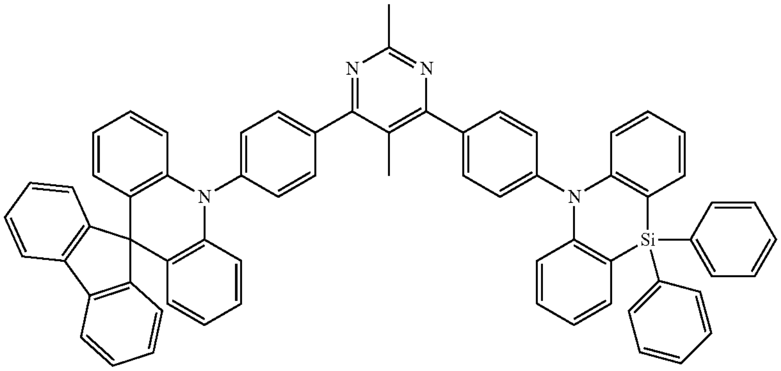
91
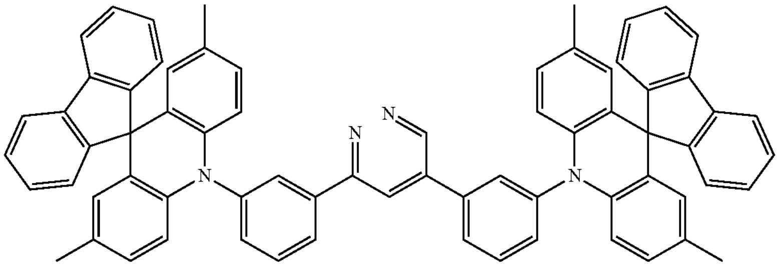
92
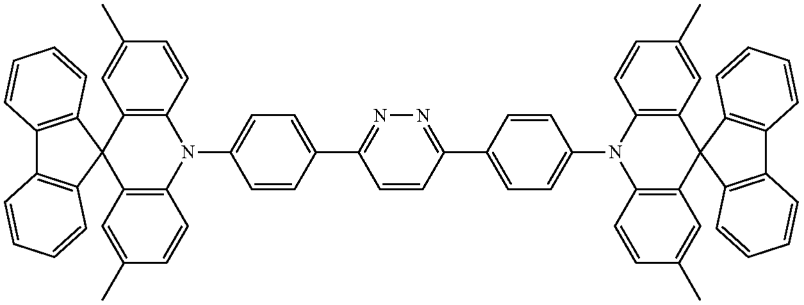
93
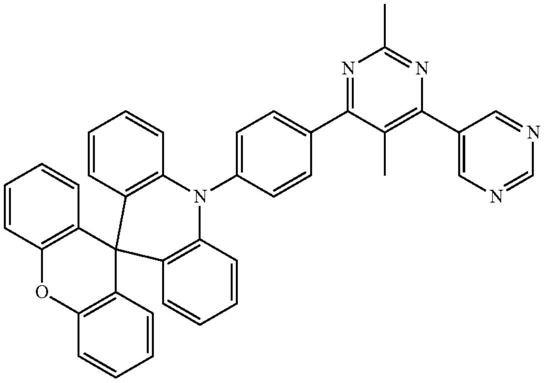
94
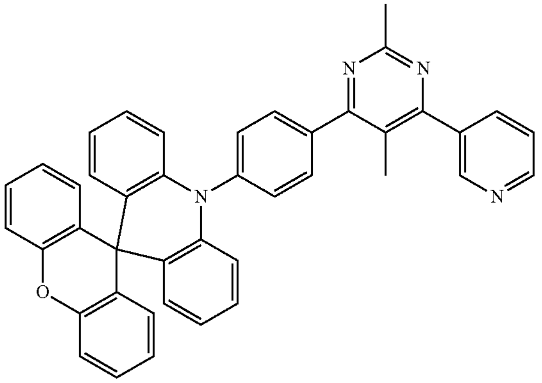

-continued

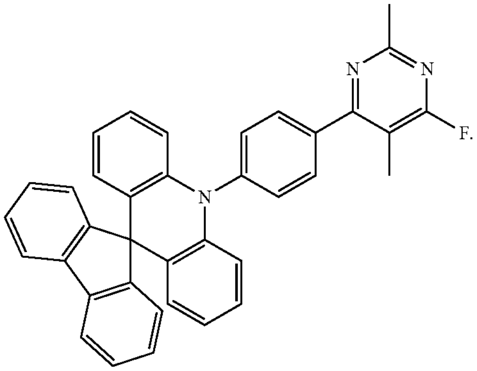

7. An organic electroluminescence device, comprising:

a first electrode;

a hole transport region on the first electrode;

an emission layer on the hole transport region;

an electron transport region on the emission layer; and a second electrode on the electron transport region, wherein the emission layer includes a host and a dopant, the dopant being included in an amount less than that of the host and being a nitrogen-containing compound represented by the following Formula 1:

[Formula 1]

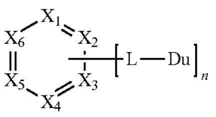

wherein, in Formula 1, $X_1$ to $X_6$ are each independently $CR_1$ or N provided that one or two of $X_1$ to $X_6$ are N and the others are $CR_1$, each $R_1$ is independently a bond to L, a hydrogen atom, a deuterium atom, a halogen atom, a substituted or unsubstituted alkyl group having 1 to 30 carbon atoms, a substituted or unsubstituted aryl group having 6 to 30 ring carbon atoms, or a substituted or unsubstituted heteroaryl group having 2 to 30 ring carbon atoms, L is a substituted or unsubstituted arylene group having 6 to 30 ring carbon atoms, n is 1 or 2, and Du is a group represented by one selected from the following Formulae 7-9 and 12-16, when only one of $X_1$ to $X_6$ is N, Du is a group represented by the following Formulae 8 to 9 and 13 to 16, and when only two of $X_1$ to $X_6$ are N, Du is a group represented by one selected from the following Formulae 7 to 9 and 12 to 16,

[Formula 7]

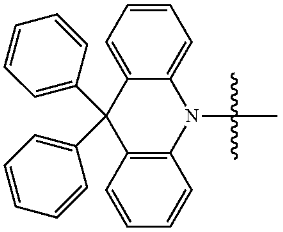

-continued

[Formula 8]

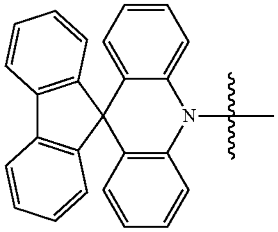

[Formula 9]

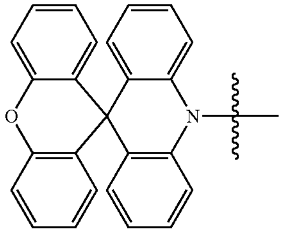

[Formula 10]

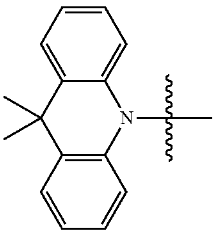

[Formula 11]

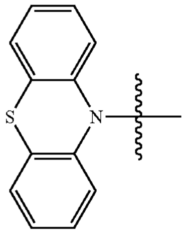

-continued

[Formula 12]

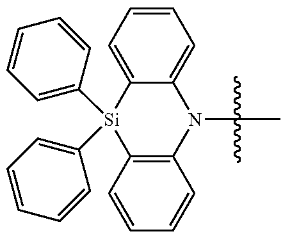

[Formula 13]

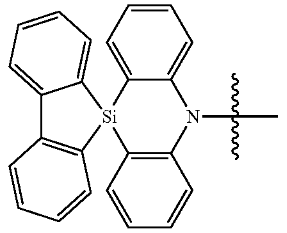

[Formula 14]

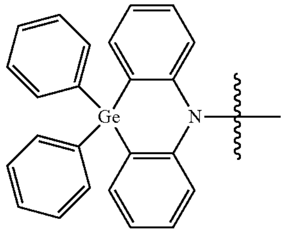

[Formula 15]

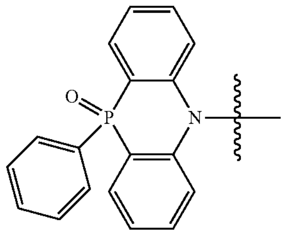

[Formula 16]

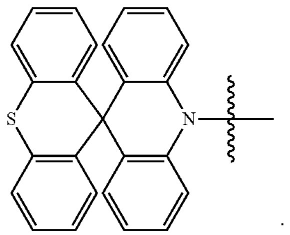

.

wherein, in Formulae 7-9 and 12-16,

represents a bonding site with L of Formula 1, or the nitrogen-containing compound is represented by the following Formula 5:

[Formula 5]

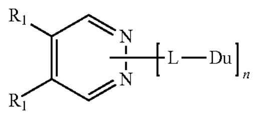

wherein, in Formula 5, L, Du, $R_1$, and n are defined the same as those of Formula 1.

8. The organic electroluminescence device as claimed in claim 7, wherein an absolute value of a difference between a singlet energy level and a triplet energy level of the nitrogen-containing compound represented by Formula 1 or a triplet energy level of the nitrogen-containing compound represented by Formula 5 is about 0.2 eV or less.

9. The organic electroluminescence device as claimed in claim 7, wherein L is a substituted or unsubstituted phenylene group.

10. The organic electroluminescence device as claimed in claim 7, wherein the nitrogen-containing compound represented by Formula 1 is represented by the following Formula 3:

[Formula 3]

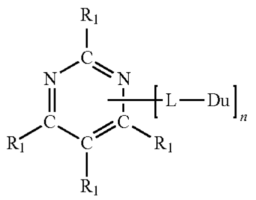

wherein, in Formula 3, L, Du, $R_1$, and n are defined the same as those of Formula 1.

11. The organic electroluminescence device as claimed in claim 7, wherein the nitrogen-containing compound represented by Formula 1 is represented by the following Formula 4:

[Formula 4]

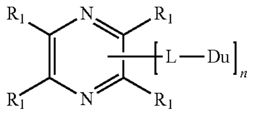

wherein, in Formula 4, L, Du, $R_1$, and n are defined the same as those of Formula 1.

12. The organic electroluminescence device as claimed in claim 7, wherein the nitrogen-containing compound is represented by the following Formula 6:

[Formula 6]

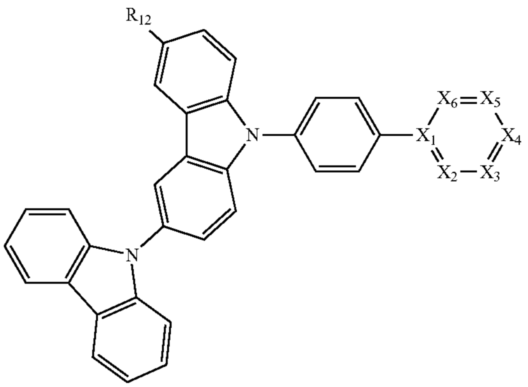

wherein, in Formula 6, $R_{12}$ is a hydrogen atom, or substituted or unsubstituted aryl group having 6 to 30 ring carbon atoms, and $X_1$ to $X_6$ are defined the same as those of Formula 1.

13. The organic electroluminescence device as claimed in claim 7, wherein the nitrogen-containing compound represented by Formula 1 is one of the following Compounds:

1
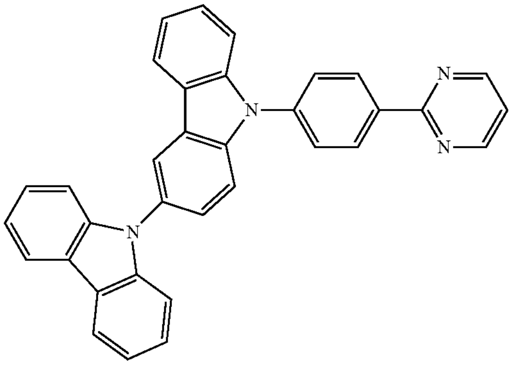
2
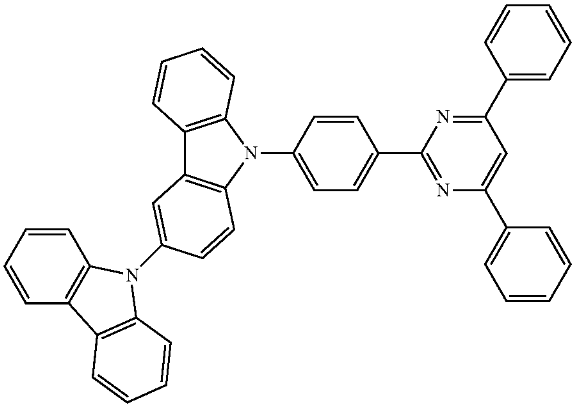
3
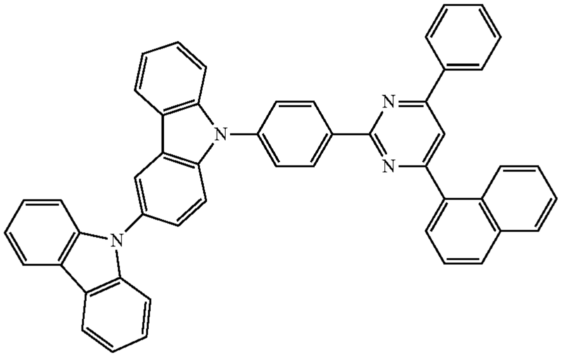
4
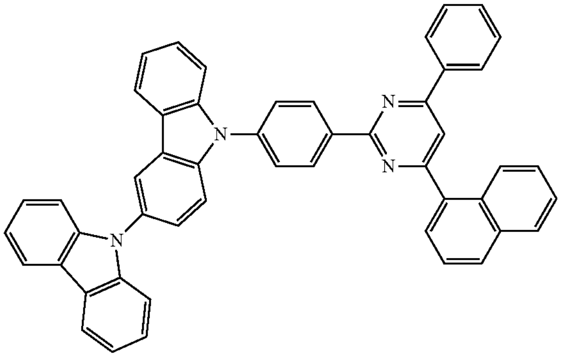
5
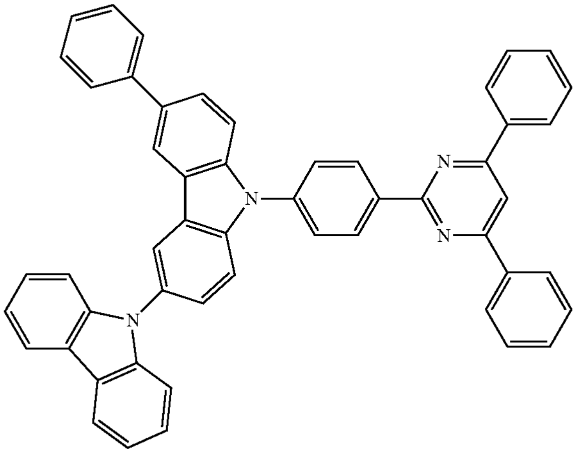
6
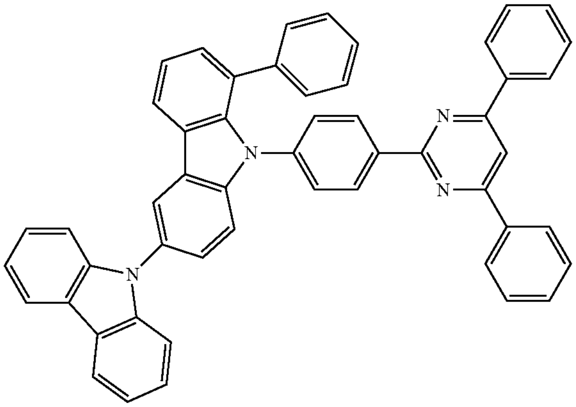
7
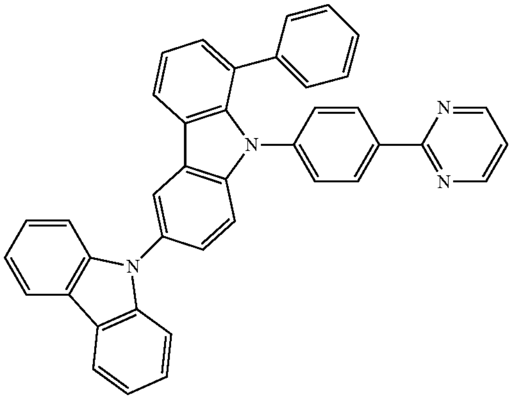
8
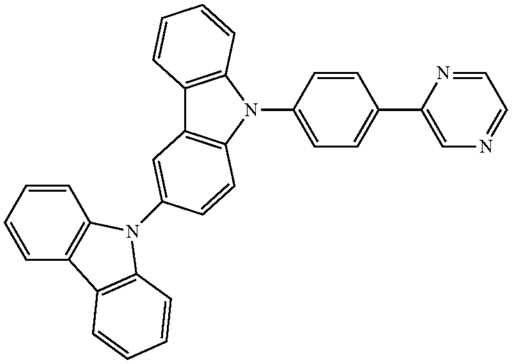

-continued
9
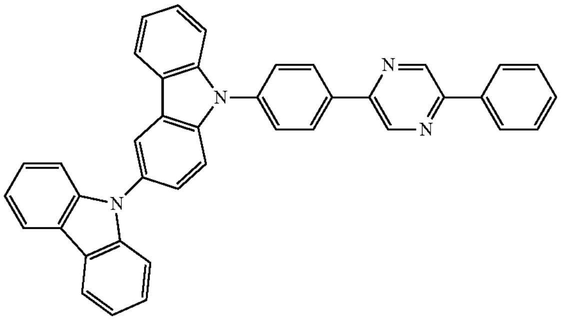
10
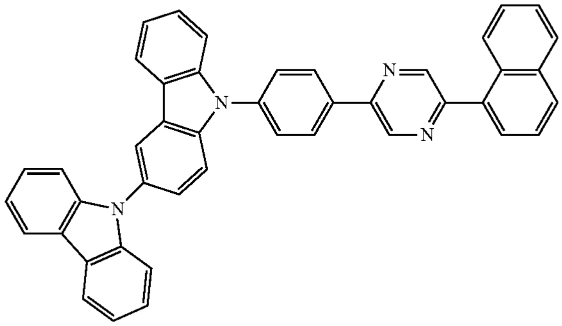
11
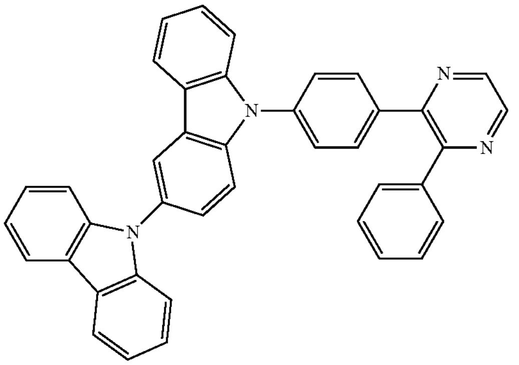
12
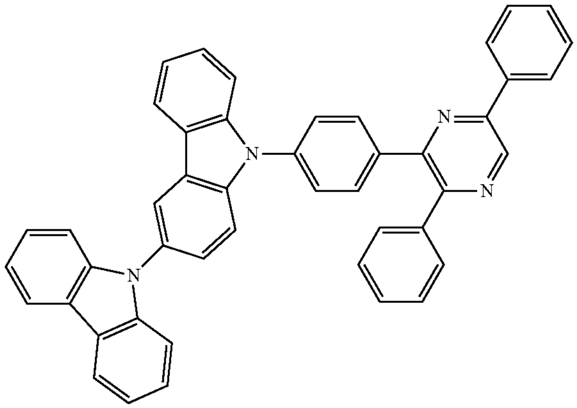
13
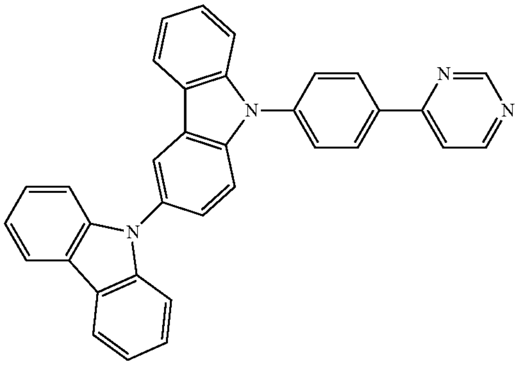
14
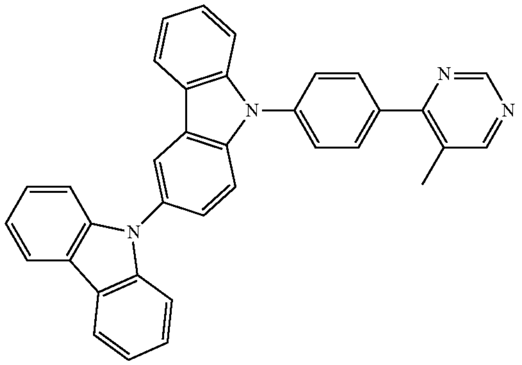
15
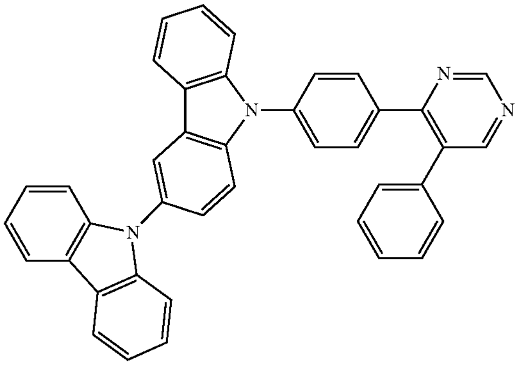
16
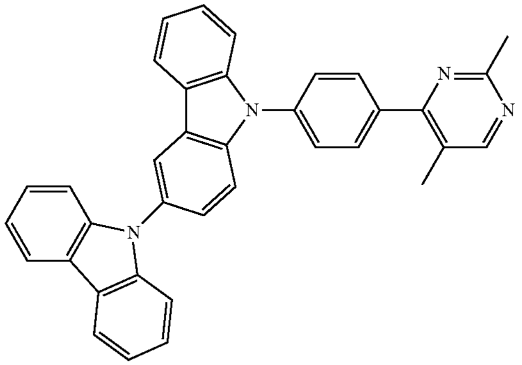

-continued
17
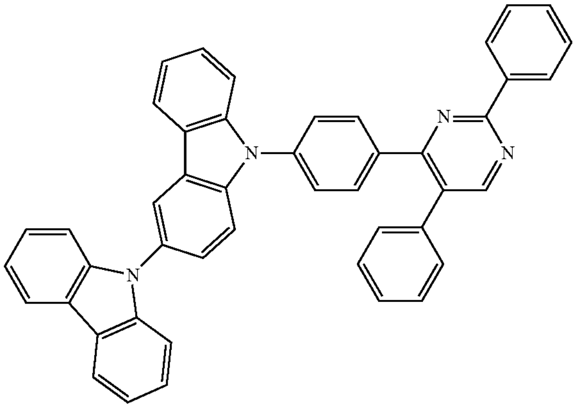
18
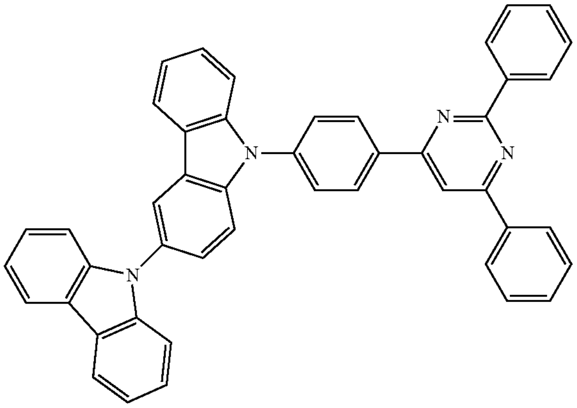
37
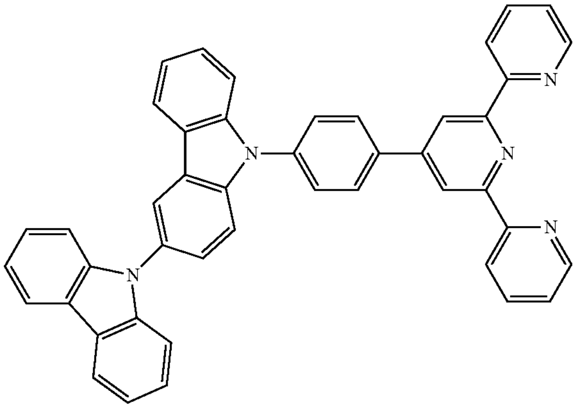
38
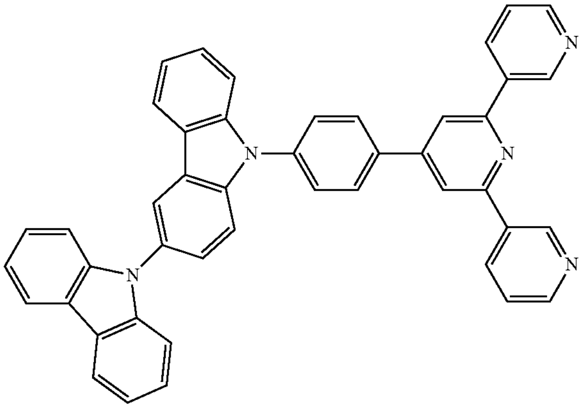
39
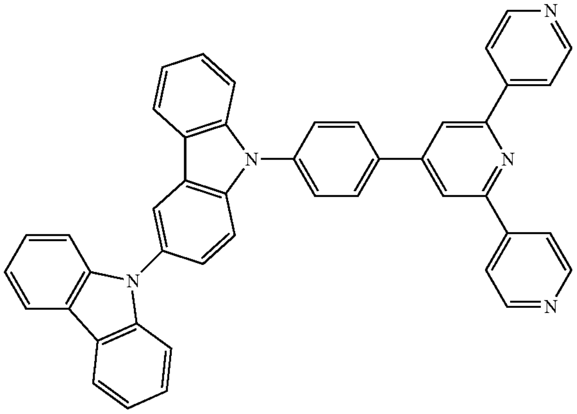

-continued
40
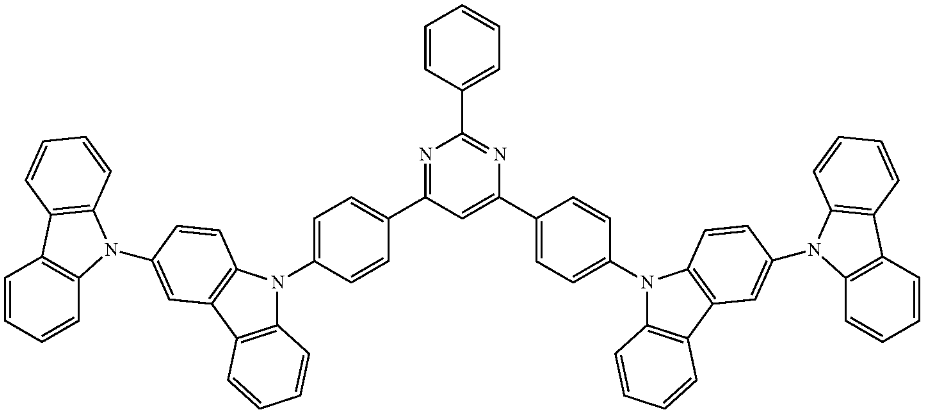
41
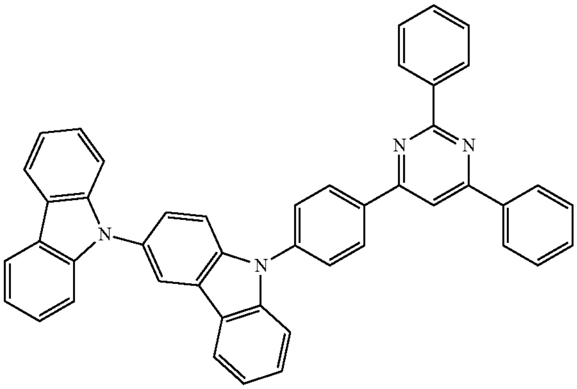
42
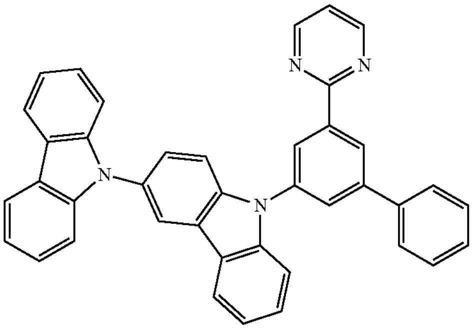
43
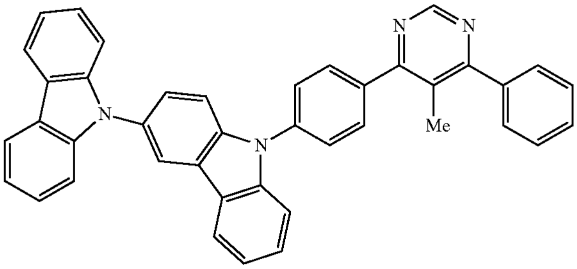
44
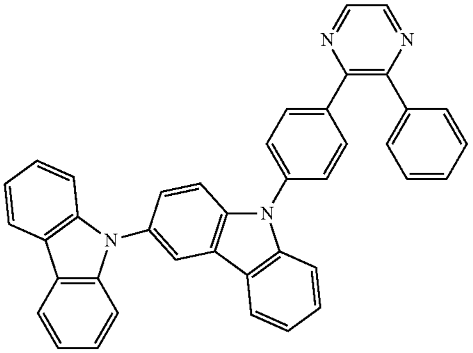
45
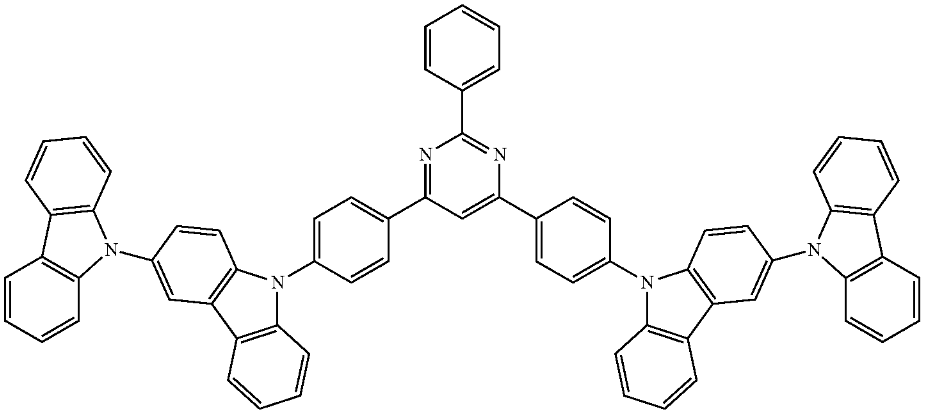

-continued
46
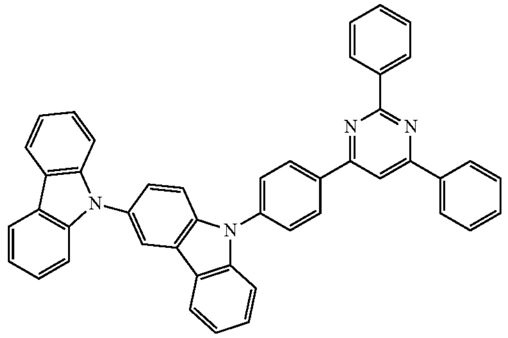
47
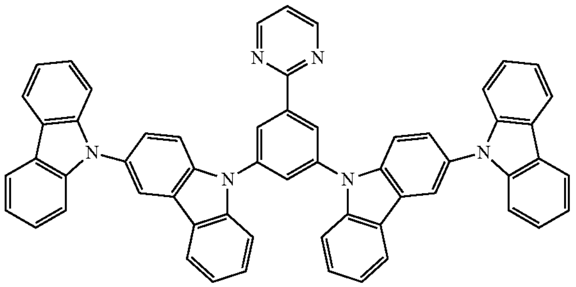
48
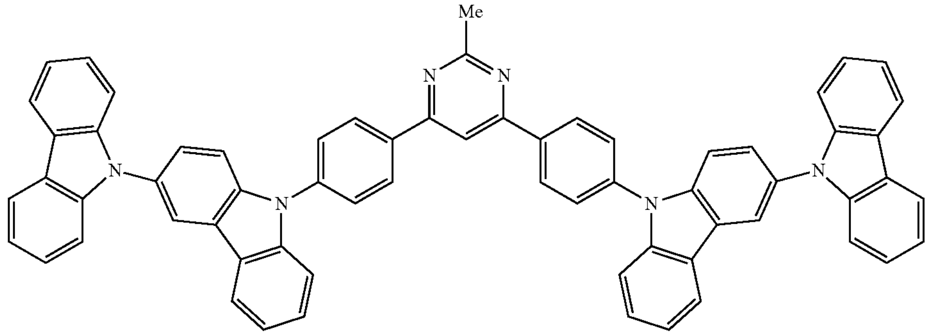
49
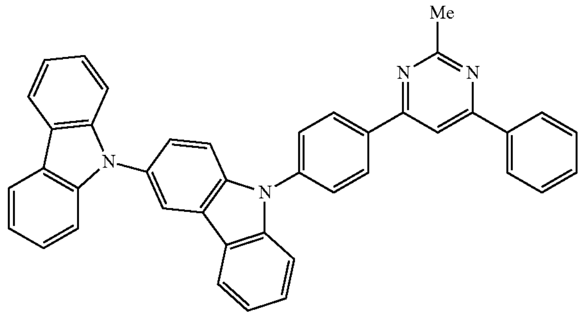
50
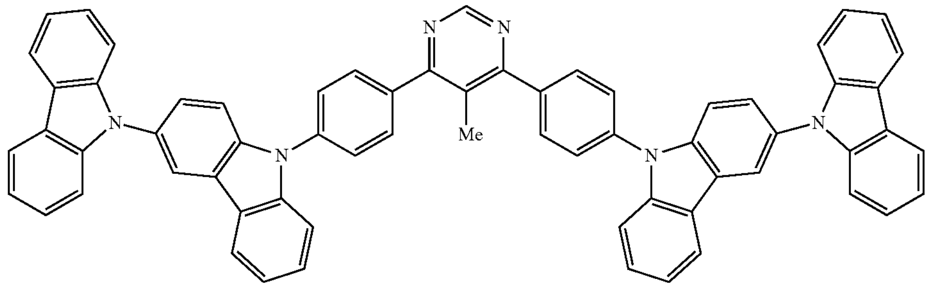

-continued
51
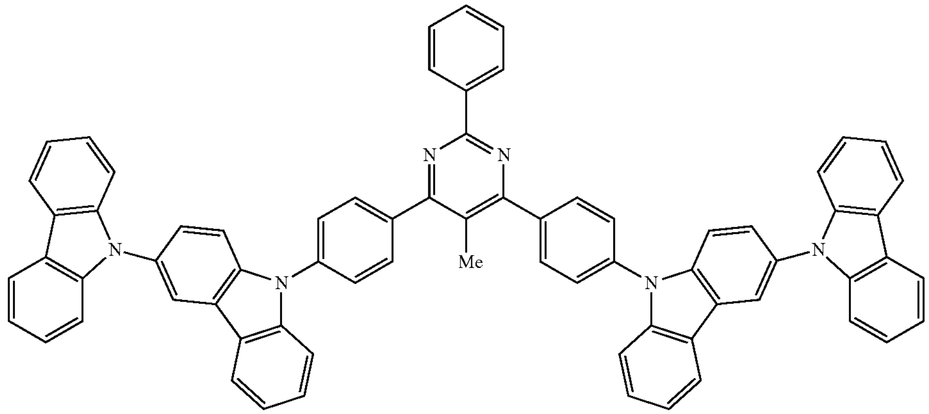
52
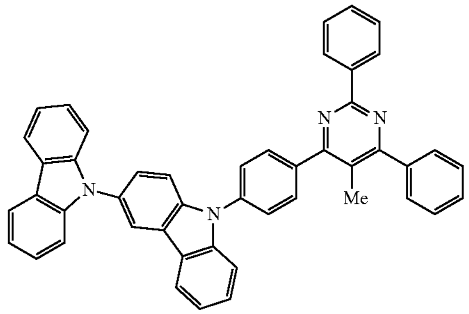
53
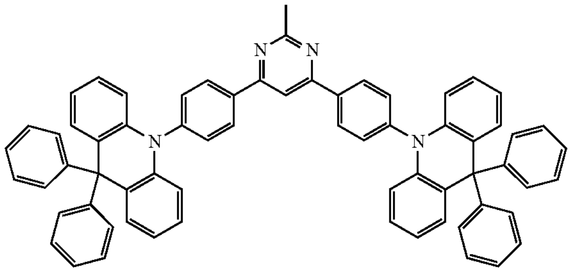
54
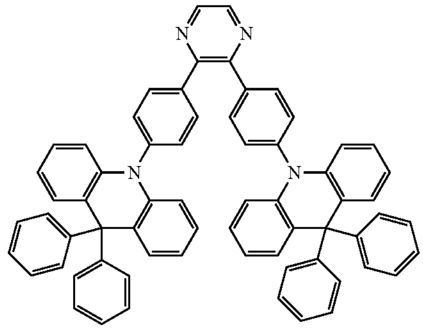
55
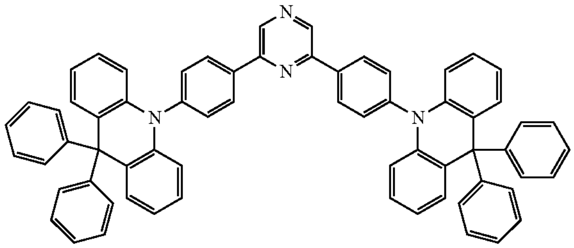
56
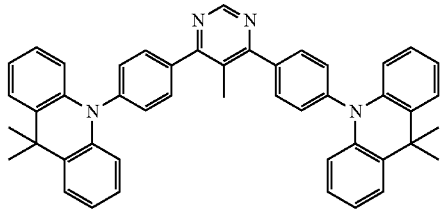
57
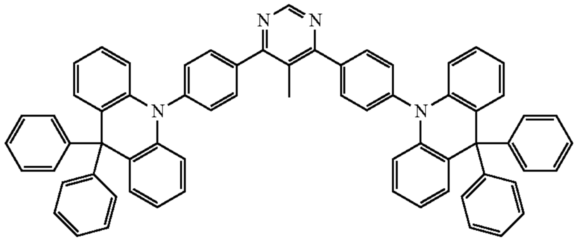

-continued
58
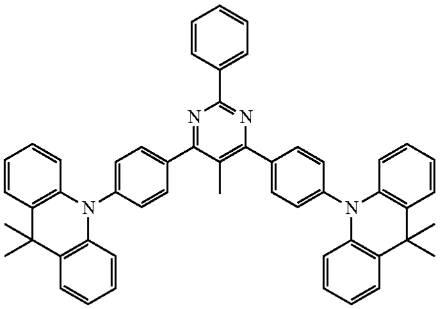
59
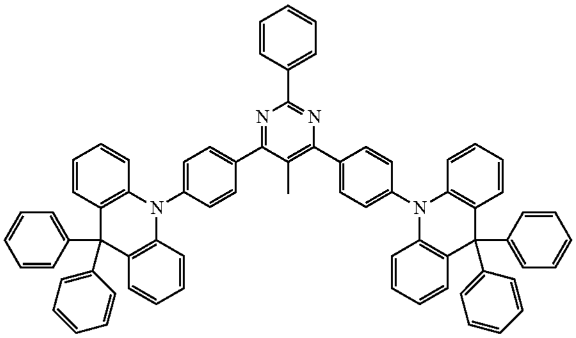
60
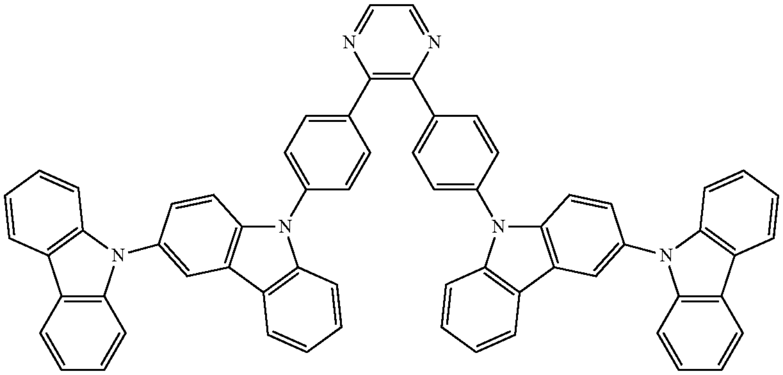
61
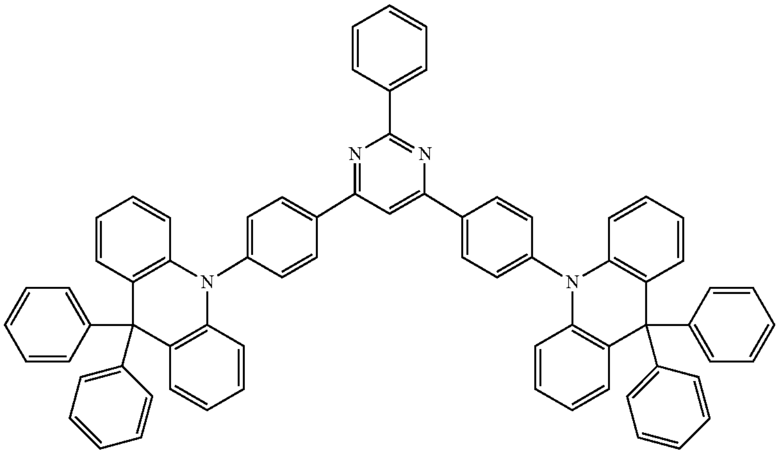
62
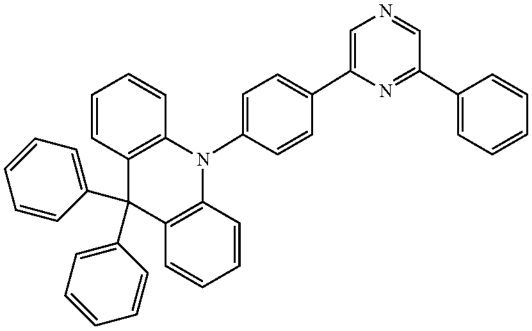
63
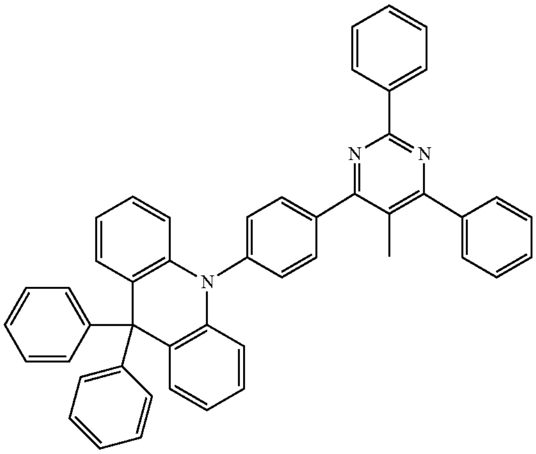

-continued
64
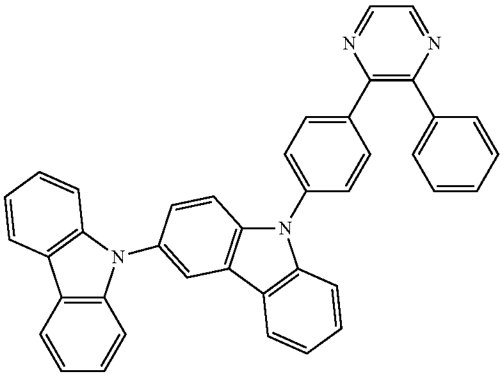
65
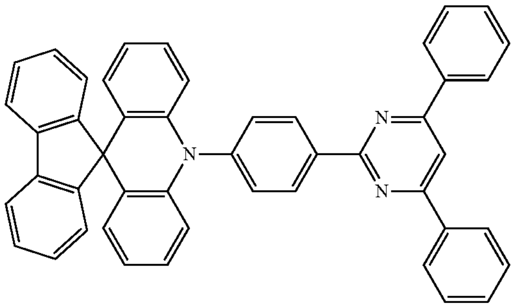
66
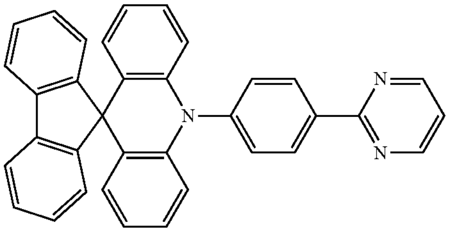
67
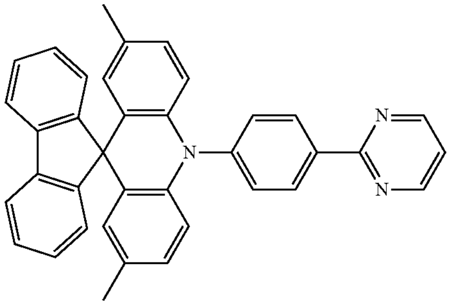
68
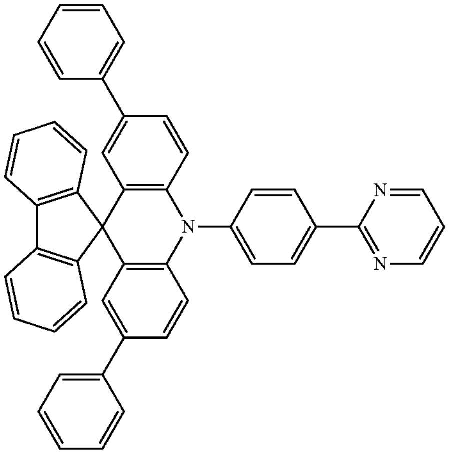
69
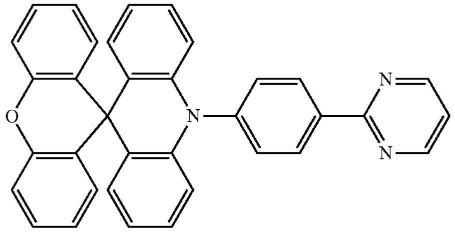
70
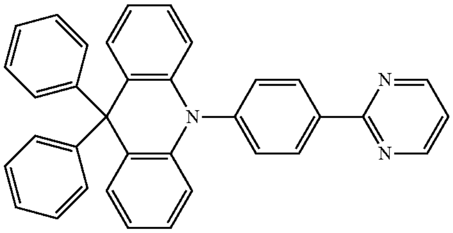
71
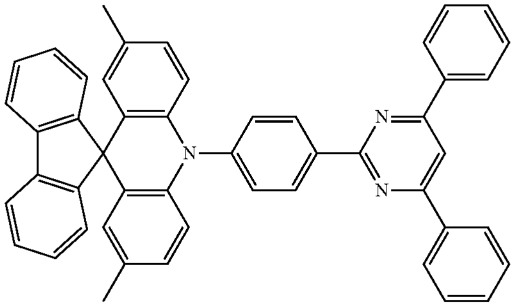

-continued
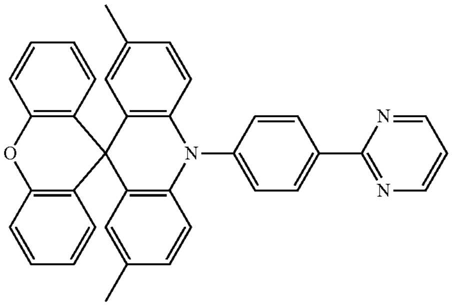
72
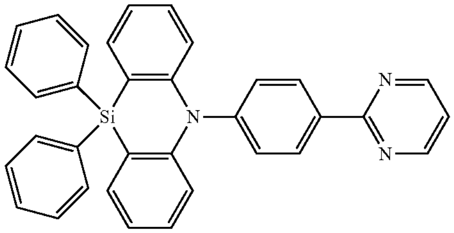
73
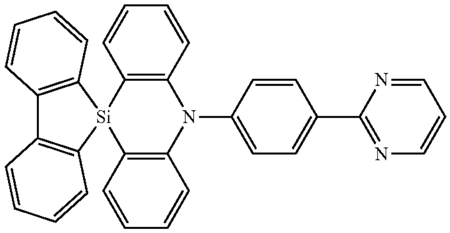
74
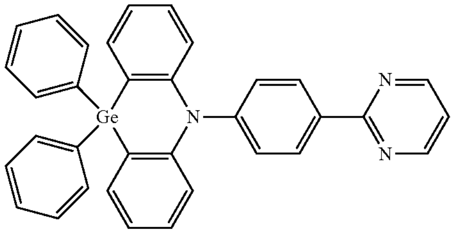
75
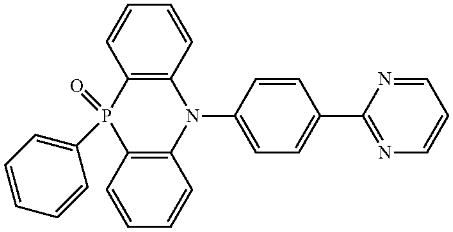
76
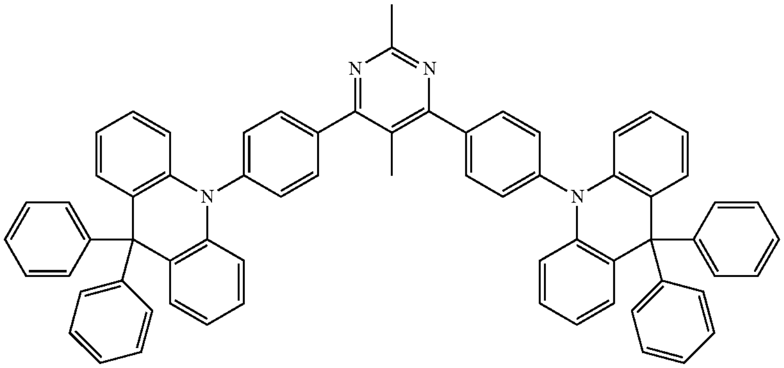
77
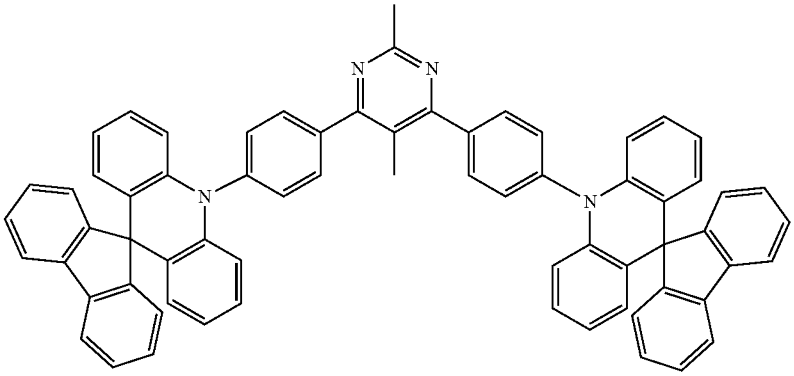
78

-continued
79
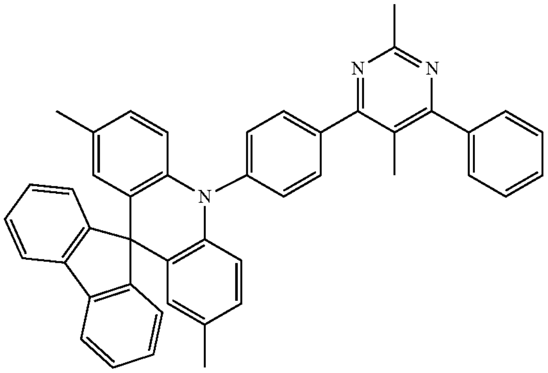
80
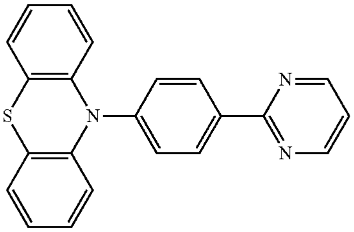
81
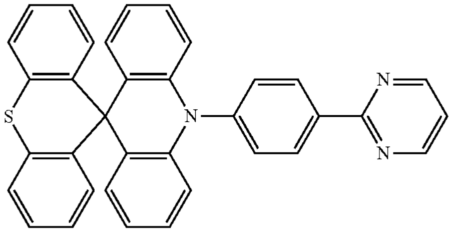
82
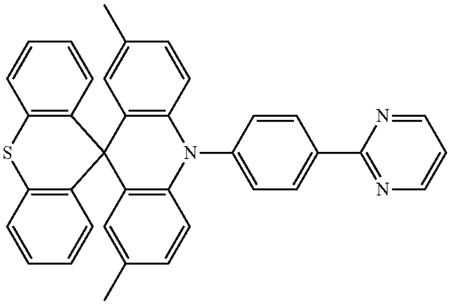
83
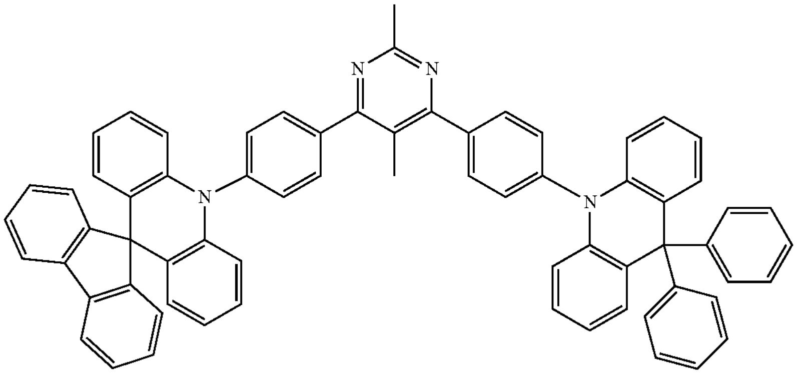
84
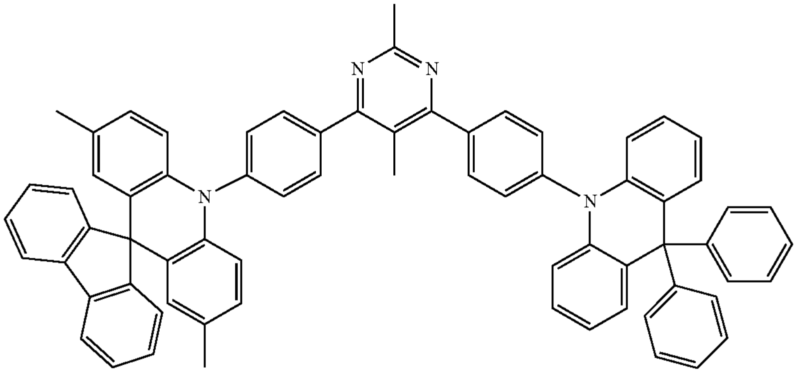

-continued
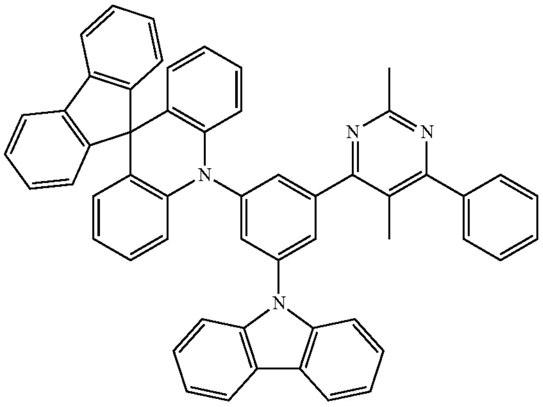
85
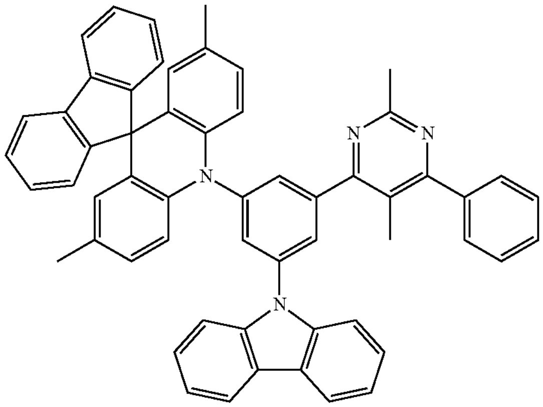
86
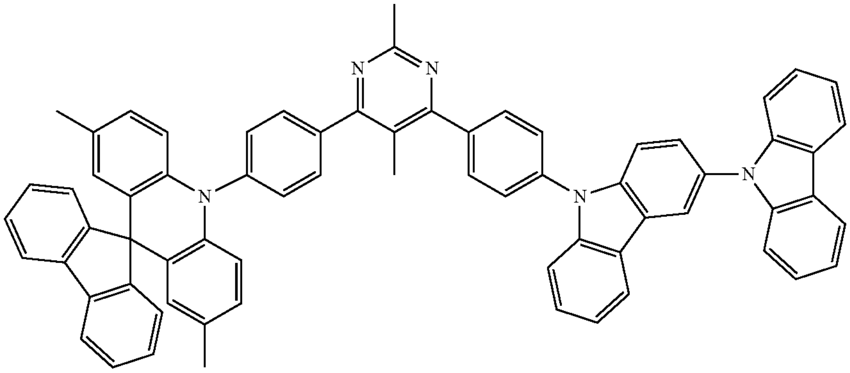
87
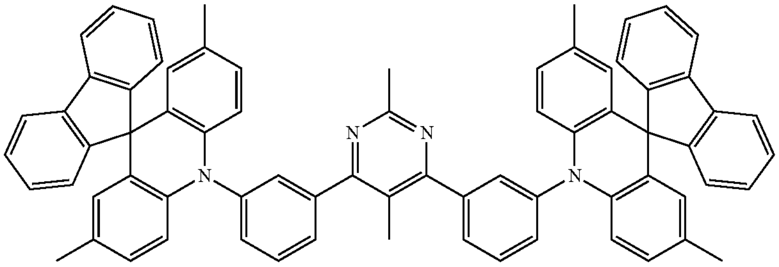
88
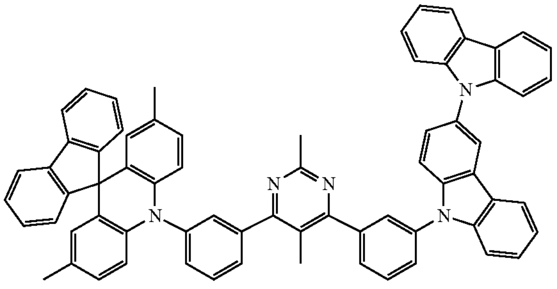
89

-continued
90
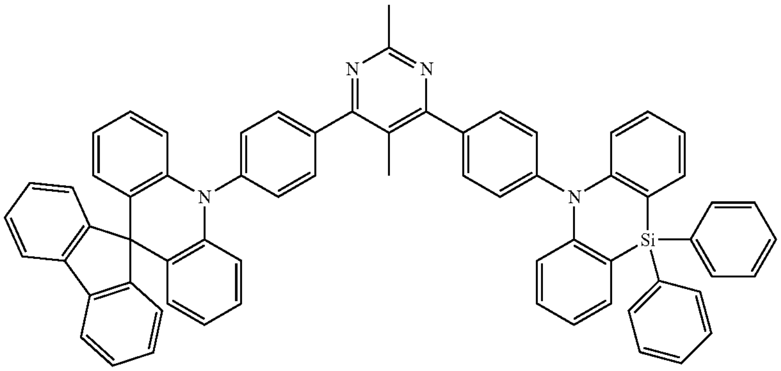
91
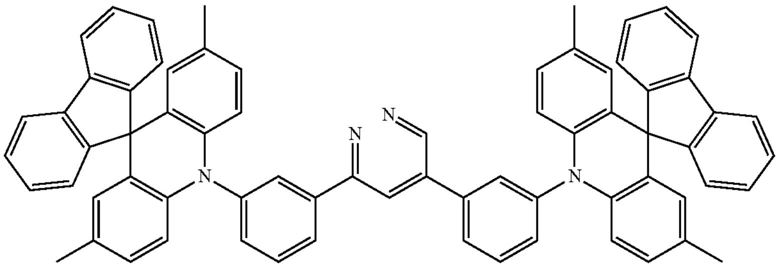
92
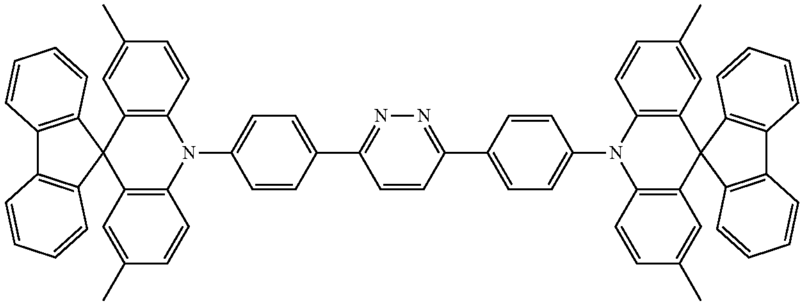
93
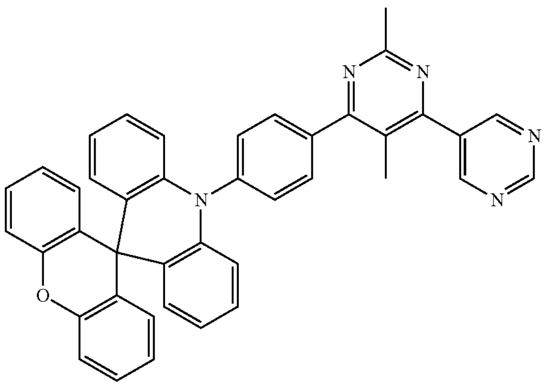
94
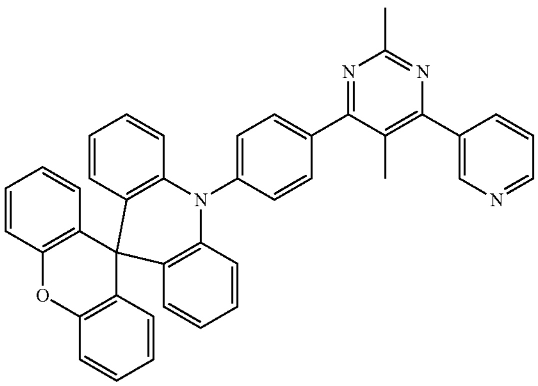

-continued
95
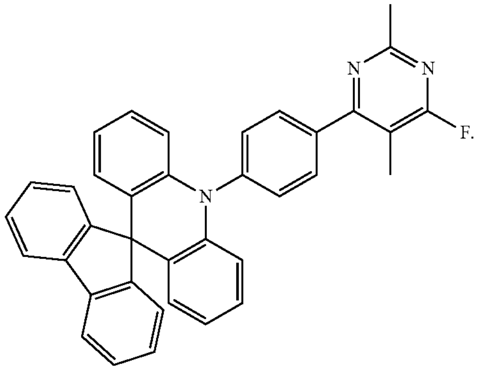
14. The organic electroluminescence device as claimed in claim 7, wherein:
the hole transport region includes a hole injection layer and a hole transport layer, and
the electron transport region includes an electron injection layer and an electron transport layer.
15. A nitrogen-containing compound represented by one of the following Compounds 53, 55, 61, 66, 67, 69, 70, or 71:
53
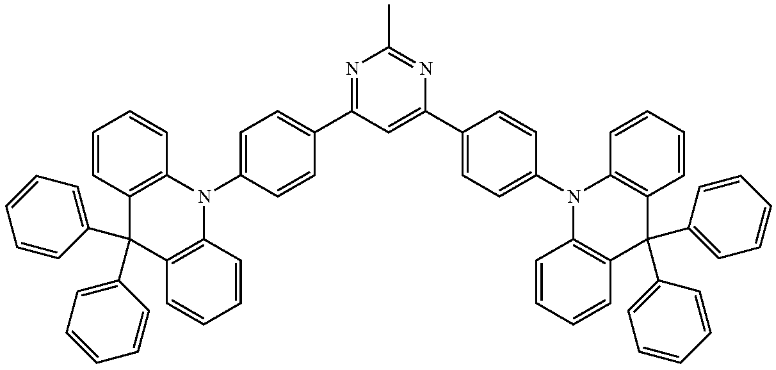
55
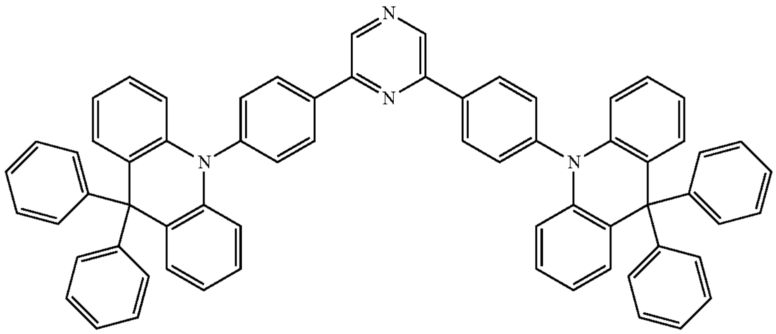

-continued

61

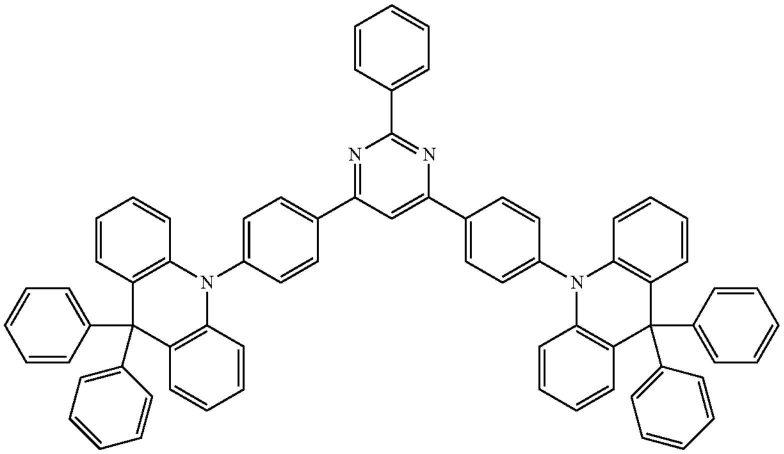

66

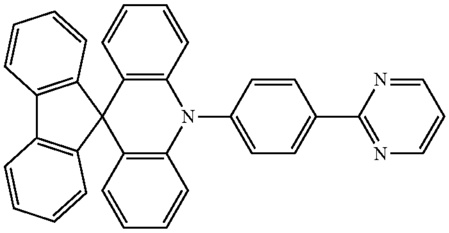

67

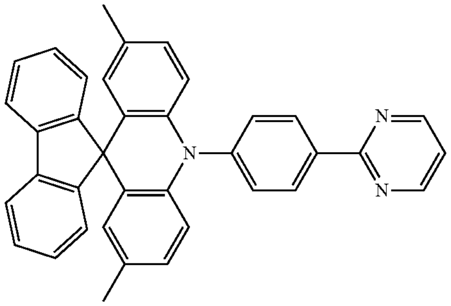

69

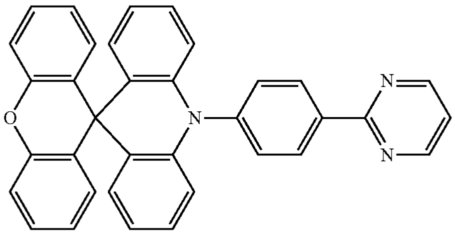

70

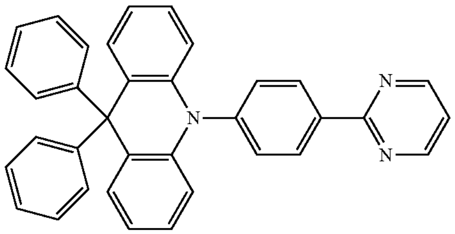

71

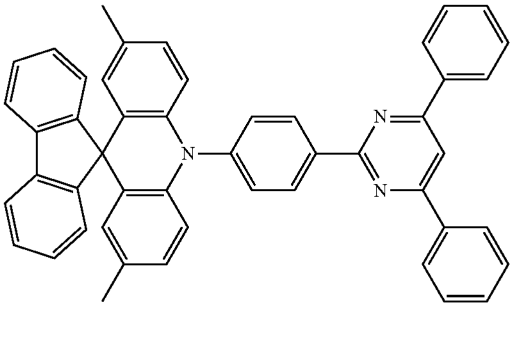

16. An organic electroluminescence device, comprising:

a first electrode;

a hole transport region on the first electrode;

an emission layer on the hole transport region;

an electron transport region on the emission layer; and a second electrode on the electron transport region, wherein the emission layer includes the nitrogen-containing compound as claimed in claim 15.

17. The organic electroluminescence device as claimed in claim 16, wherein an absolute value of a difference between a singlet energy level and a triplet energy level of the nitrogen-containing compound is about 0.2 eV or less.

18. The organic electroluminescence device as claimed in claim 16, wherein the nitrogen containing compound is a dopant in the emission layer.

* * * * *

UNITED STATES PATENT AND TRADEMARK OFFICE

CERTIFICATE OF CORRECTION

PATENT NO. : 10,686,139 B2
APPLICATION NO. : 15/378084
DATED : June 16, 2020
INVENTOR(S) : Hiromi Nakano et al.

It is certified that error appears in the above-identified patent and that said Letters Patent is hereby corrected as shown below:

In the Claims

Column 130, Line 40 (approx.), Claim 1, Formula 16 delete "." and insert -- , --

Column 149, Line 49 (approx.), Claim 7, Formula 16 delete "." and insert -- , --

Column 177, Lines 51-54 (approx.), Claim 15, After Compound 71 insert -- . --

Signed and Sealed this
Twenty-eighth Day of June, 2022

Katherine Kelly Vidal

Katherine Kelly Vidal
*Director of the United States Patent and Trademark Office*